US006878557B1

(12) United States Patent
Zambias et al.

(10) Patent No.: US 6,878,557 B1
(45) Date of Patent: Apr. 12, 2005

(54) LOGICALLY ORDERED ARRAYS OF COMPOUNDS AND METHODS OF MAKING AND USING THE SAME

(75) Inventors: Robert Zambias, Lexington, MA (US); David A. Bolten, Tinton Falls, NJ (US); Joseph C. Hogan, Belmont, MA (US); Paul Furth, Waltham, MA (US); David Casebier, Hudson, MA (US); Cheng Tu, Cambridge, MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 09/009,846

(22) Filed: Jan. 20, 1998

(Under 37 CFR 1.47)

Related U.S. Application Data

(63) Continuation of application No. 08/375,838, filed on Jan. 20, 1995, now Pat. No. 5,712,171.

(51) Int. Cl.[7] ...................... G01N 33/543; A61K 38/00; C07H 21/02; C12Q 1/68

(52) U.S. Cl. ..................... 436/518; 435/6; 435/DIG. 1; 435/DIG. 48; 530/338; 536/25.3

(58) Field of Search ......................... 436/518; 530/338; 536/25.3; 435/DIG. 1, DIG. 48, 6

(56) References Cited

U.S. PATENT DOCUMENTS

| | | | |
|---|---|---|---|
| 3,410,880 | A | 11/1966 | Brockenhurst |
| 3,450,673 | A | 6/1969 | McKillip |
| 3,485,806 | A | 12/1969 | Bloomquist et al. |
| 3,488,327 | A | 1/1970 | Kollinsky et al. |
| 3,488,389 | A | 1/1970 | McKillip |
| 3,499,032 | A | 3/1970 | Clemens et al. |
| 3,511,894 | A | 5/1970 | Markert |
| 3,527,802 | A | 9/1970 | Slagel |
| 3,555,095 | A | 1/1971 | Slagel |
| 3,565,868 | A | 2/1971 | Sedor et al. |
| 3,567,725 | A | 3/1971 | Grabowski et al. |
| 3,583,950 | A | 6/1971 | Kollinsky et al. |
| 3,598,790 | A | 8/1971 | Kollinsky et al. |
| 3,641,145 | A | 2/1972 | Culbertson |
| 3,664,990 | A | 5/1972 | Slagel |
| 3,671,473 | A | 6/1972 | Sedor et al. |
| 3,676,453 | A | 7/1972 | Pines et al. |
| 3,704,128 | A | 11/1972 | Koda et al. |
| 3,706,797 | A | 12/1972 | McKillip et al. |
| 3,706,800 | A | 12/1972 | Hartlage et al. |
| 3,715,343 | A | 2/1973 | Slagel et al. |
| 3,728,387 | A | 4/1973 | Freis et al. |
| 3,756,994 | A | 9/1973 | Culbertson |
| 3,781,319 | A | 12/1973 | Wawzonek et al. |
| 3,803,220 | A | 4/1974 | Gasman |
| 3,811,887 | A | 5/1974 | Ishihara et al. |
| 3,818,065 | A | 6/1974 | Schoellkopf et al. |
| 3,828,007 | A | 8/1974 | Throckmorton |
| 3,850,969 | A | 11/1974 | Grimm et al. |
| 3,794,495 | A | 12/1974 | Ishihara et al. |
| 3,893,974 | A | 7/1975 | Niino et al. |
| 3,898,087 | A | 8/1975 | Brutchen et al. |
| 3,904,749 | A | 9/1975 | McKillip |
| 3,925,284 | A | 12/1975 | Carleton et al. |
| 3,934,029 | A | 1/1976 | Kabara |
| 3,934,031 | A | 1/1976 | Kabara |
| 3,934,035 | A | 1/1976 | Kabara |
| 3,946,131 | A | 3/1976 | Biefeld et al. |
| 3,948,866 | A | 4/1976 | Pennewiss et al. |
| 3,963,703 | A | 6/1976 | Culbertson |
| 3,963,776 | A | 6/1976 | Middleton |
| 3,968,065 | A | 7/1976 | Morris et al. |
| 3,969,298 | A | 7/1976 | Gasman |
| 3,983,166 | A | 9/1976 | Samour |
| 3,985,807 | A | 10/1976 | Grimm et al. |
| 4,005,055 | A | 1/1977 | Miron et al. |
| 4,016,340 | A | 4/1977 | Kolesinski et al. |
| 4,022,623 | A | 5/1977 | Fitzgerald et al. |
| 4,046,658 | A | 9/1977 | Brown |
| 4,067,830 | A | 1/1978 | Kresta |
| 4,070,348 | A | 1/1978 | Kraemer et al. |
| 4,078,901 | A | 3/1978 | Sung et al. |
| 4,080,206 | A | 3/1978 | Kolesinski et al. |
| 4,097,444 | A | 6/1978 | Teige et al. |

(Continued)

FOREIGN PATENT DOCUMENTS

| | | |
|---|---|---|
| EP | 0 185 493 | 6/1986 |
| EP | 0 212 617 | 4/1987 |

(Continued)

OTHER PUBLICATIONS

Pending U.S. patent application No. 08/177,497, filed Jan. 5, 1994, entitled "Method of Identifying Chemical Compounds Having Selected Properties for a Particular Application"(As Amended) by Joseph C. Hogan, Jr.

Baldwin et al., 1995, "Synthesis of a Small Molecule Combinatorial Library Encoded with Molecular Tags," *J. Am. Chem. Soc. 117*:5588–5589.

Barbas et al., 1993, "Direct selection of antibodies that coordinate metals from semisynthetic combinatorial libraries, " *Proc. Natl. Acad. Sci. U.S.A. 90*:6385–6389.

(Continued)

*Primary Examiner*—Padmashri Ponnaluri
(74) *Attorney, Agent, or Firm*—Arnold & Porter LLP

(57) ABSTRACT

A method for constructing an array of synthetic molecular constructs, by forming a plurality of molecular constructs having a scaffold backbone of a chemical molecule comprising a linear, branched or cyclic organic compound having at least atoms of carbon, nitrogen, sulfur, phosphorus, or combinations thereof, and at least one location on the molecule capable of undergoing reaction with other molecules for attachment of at least one structural diversity element; laying out an array possessing a logical ordering of sub-arrays of the molecular constructs; providing each sub-array with molecular constructs having the scaffold backbone and at least one structural diversity element which is different from the others; and relating each sub-array within the array to all other sub arrays by the difference in the structural diversity elements.

10 Claims, 2 Drawing Sheets

U.S. PATENT DOCUMENTS

| | | | |
|---|---|---|---|
| 4,102,916 | A | 7/1978 | Falk |
| 4,122,159 | A | 10/1978 | Madrange et al. |
| 4,140,680 | A | 2/1979 | Sullivan |
| 4,162,355 | A | 7/1979 | Tsibris |
| 4,189,481 | A | 2/1980 | Kabara |
| 4,212,905 | A | 7/1980 | Tsibris |
| 4,213,860 | A | 7/1980 | Tsibris |
| 4,217,364 | A | 8/1980 | Kabara |
| 4,260,705 | A | 4/1981 | Tsibris |
| 4,280,008 | A | 7/1981 | Schoellkopf et al. |
| 4,304,705 | A | 12/1981 | Heilmann et al. |
| 4,378,411 | A | 3/1983 | Heilmann et al. |
| 4,424,272 | A | 1/1984 | Taylor |
| 4,451,619 | A | 5/1984 | Heilmann et al. |
| 4,485,236 | A | 11/1984 | Rasmussen et al. |
| 4,548,981 | A | 10/1985 | Kolesinski et al. |
| 4,563,467 | A | 1/1986 | Soler |
| 4,617,253 | A | 10/1986 | Taylor et al. |
| 4,624,995 | A | 11/1986 | Katritzky et al. |
| 4,631,211 | A | 12/1986 | Houghten |
| 4,645,711 | A | 2/1987 | Winslow |
| 4,667,012 | A | 5/1987 | Rasmussen et al. |
| 4,670,528 | A | 6/1987 | Taylor et al. |
| 4,695,608 | A | 9/1987 | Engler et al. |
| 4,705,824 | A | 11/1987 | Lin |
| 4,737,560 | A | 4/1988 | Heilmann et al. |
| 4,740,568 | A | 4/1988 | Katritzky et al. |
| 4,777,217 | A | 10/1988 | Rasmussen et al. |
| 4,777,276 | A | 10/1988 | Rasmussen et al. |
| 4,785,070 | A | 11/1988 | Rasmussen et al. |
| 4,816,554 | A | 3/1989 | Katritzksy et al. |
| 4,841,021 | A | 6/1989 | Katritzky et al. |
| 4,852,969 | A | 8/1989 | Babirad et al. |
| 4,871,824 | A | 10/1989 | Heilmann et al. |
| 4,874,822 | A | 10/1989 | Rasmussen et al. |
| 4,898,923 | A | 2/1990 | Katritzky et al. |
| 4,948,715 | A | 8/1990 | Hulme-Lowe et al. |
| 4,981,933 | A | 1/1991 | Fazio et al. |
| 5,010,175 | A | 4/1991 | Rutter et al. |
| 5,013,795 | A | 5/1991 | Coleman et al. |
| 5,039,813 | A | 8/1991 | Fazio et al. |
| 5,053,454 | A | 10/1991 | Judd |
| 5,066,559 | A | 11/1991 | Elmasry et al. |
| 5,075,352 | A | 12/1991 | Elmasry |
| 5,081,197 | A | 1/1992 | Heilmann et al. |
| 5,091,489 | A | 2/1992 | Heilmann et al. |
| 5,094,766 | A | 3/1992 | Kapuscinski et al. |
| 5,138,071 | A | 8/1992 | Schoellkopf et al. |
| 5,143,854 | A | 9/1992 | Pirrung et al. |
| 5,147,957 | A | 9/1992 | Kumar |
| 5,149,806 | A | 9/1992 | Moren et al. |
| 5,157,108 | A | 10/1992 | Krepski et al. |
| 5,157,145 | A | 10/1992 | Schoellkopf et al. |
| 5,175,081 | A | 12/1992 | Krepski et al. |
| 5,182,366 | A | 1/1993 | Huebner et al. |
| 5,185,102 | A | 2/1993 | Harelstad et al. |
| 5,194,623 | A | 3/1993 | Krepski et al. |
| 5,200,471 | A | 4/1993 | Coleman et al. |
| 5,202,418 | A | 4/1993 | Lebl et al. |
| 5,223,409 | A | 6/1993 | Ladner et al. |
| 5,225,533 | A | 7/1993 | Rutter et al. |
| 5,288,514 | A | 2/1994 | Ellman |
| 5,300,425 | A | 4/1994 | Kauvar |
| 5,324,483 | A | 6/1994 | Cody et al. ................. 422/131 |
| 5,340,474 | A | 8/1994 | Kauvar |
| 5,359,115 | A | 10/1994 | Campbell et al. |
| 5,367,053 | A | 11/1994 | Dooley et al. |
| 5,424,186 | A | 6/1995 | Fodor et al. |
| 5,449,754 | A | 9/1995 | Nishioka |
| 5,463,564 | A | 10/1995 | Agrafiotis et al. |
| 5,464,759 | A | 11/1995 | Coolidge et al. |
| 5,470,753 | A | 11/1995 | Sepetov et al. |
| 5,503,805 | A | 4/1996 | Sugarman et al. |
| 5,506,337 | A | 4/1996 | Summerton et al. |
| 5,525,734 | A | 6/1996 | Gallop et al. |
| 5,525,735 | A | 6/1996 | Gallop et al. |
| 5,545,568 | A | 8/1996 | Ellman |
| 5,565,173 | A | 10/1996 | DeWitt et al. .............. 422/131 |
| 5,567,391 | A | 10/1996 | DeWitt et al. .............. 422/131 |
| 5,571,698 | A | 11/1996 | Ladner et al. |
| 5,574,656 | A | 11/1996 | Agrafiotis et al. |
| 5,582,801 | A | 12/1996 | DeWitt et al. .............. 422/131 |
| 5,593,642 | A | 1/1997 | DeWitt et al. .............. 422/131 |
| 5,609,826 | A | 3/1997 | Cargill et al. |
| 5,612,002 | A | 3/1997 | Cody et al. ................. 422/131 |
| 5,614,608 | A | 3/1997 | Krchnak et al. |
| 5,639,866 | A | 6/1997 | Kahne |
| 5,646,285 | A | 7/1997 | Baindur et al. |
| 5,651,943 | A | 7/1997 | Lam et al. |
| 5,663,046 | A | 9/1997 | Baldwin et al. |
| 5,670,326 | A | 9/1997 | Beutel |
| 5,684,711 | A | 11/1997 | Agrafiotis et al. |
| 5,702,672 | A | 12/1997 | DeWitt et al. .............. 422/131 |
| 5,712,171 | A | 1/1998 | Zambias et al. ............ 436/518 |
| 5,714,127 | A | 2/1998 | DeWitt et al. .............. 422/131 |
| 5,736,412 | A | 4/1998 | Zambias et al. ............ 436/518 |
| 5,738,996 | A | 4/1998 | Hodges et al. |
| 5,744,305 | A | 4/1998 | Fodor et al. |
| 5,766,556 | A | 6/1998 | DeWitt et al. .............. 422/131 |
| 5,770,455 | A | 6/1998 | Cargill et al. |
| 5,792,431 | A | 8/1998 | Moore et al. |
| 5,807,683 | A | 9/1998 | Brenner |
| 5,831,014 | A | 11/1998 | Cook et al. |
| 5,846,841 | A | 12/1998 | Sepetov et al. |
| 5,864,010 | A | 1/1999 | Cook et al. |
| 5,877,030 | A | 3/1999 | Rebek, Jr. et al. .......... 436/518 |
| 5,877,278 | A | 3/1999 | Zuckermann et al. |
| 5,958,702 | A | 9/1999 | Benner |
| 5,962,736 | A | 10/1999 | Zambias et al. ............ 564/152 |
| 5,968,736 | A | 10/1999 | Still et al. |
| 5,985,356 | A | 11/1999 | Schultz et al. |
| 5,985,551 | A | 11/1999 | Brennan |
| 6,001,579 | A | 12/1999 | Still et al. |
| 6,060,596 | A | 5/2000 | Lerner et al. |
| 6,096,276 | A | 8/2000 | Laursen |
| 6,121,048 | A | 9/2000 | Zaffaroni et al. |
| 6,245,937 | B1 | 6/2001 | Cheng et al. |
| 6,319,668 | B1 | 11/2001 | Nova et al. |

FOREIGN PATENT DOCUMENTS

| | | | |
|---|---|---|---|
| EP | 0 604 552 | B1 | 2/1997 |
| EP | 0 734 530 | B1 | 11/1997 |
| EP | 0 643 778 | B1 | 5/2000 |
| GB | 1128382 | | 9/1968 |
| GB | 1 181 218 | | 2/1970 |
| GB | 1 265 163 | | 3/1972 |
| GB | 1284304 | | 8/1972 |
| JP | 63 17933 | | 4/1988 |
| WO | WO 90/15070 | | 12/1990 |
| WO | WO 91/17271 | | 11/1991 |
| WO | WO 91/19735 | | 12/1991 |
| WO | WO 91/19818 | | 12/1991 |
| WO | 92/00091 | | 1/1992 |
| WO | WO 92/10092 | | 6/1992 |
| WO | 93/08278 | | 4/1993 |
| WO | WO 93/09668 | | 5/1993 |
| WO | WO 93/20242 | | 10/1993 |
| WO | 93/20935 | | 10/1993 |
| WO | WO 93/22684 | | 11/1993 |
| WO | WO 94/00509 | | 1/1994 |
| WO | WO 94/01102 | | 1/1994 |

| | | |
|---|---|---|
| WO | 94/05394 | 3/1994 |
| WO | WO 94/08051 | 4/1994 |
| WO | WO 94/08711 | 4/1994 |
| WO | 94/11388 | 5/1994 |
| WO | 94/26775 | 11/1994 |
| WO | WO 95/02566 | 1/1995 |
| WO | 95/04277 | 2/1995 |
| WO | 95/12608 | 5/1995 |
| WO | 95/13538 | 5/1995 |
| WO | WO 95/16209 | 6/1995 |
| WO | 95/16712 | 6/1995 |
| WO | 95/16918 | 6/1995 |
| WO | 95/17413 | 6/1995 |
| WO | WO 95/17903 | 7/1995 |
| WO | WO 95/18186 | 7/1995 |
| WO | WO 95/18627 | 7/1995 |
| WO | WO 95/18972 | 7/1995 |
| WO | 95/24186 | 9/1995 |
| WO | 95/30642 | 11/1995 |
| WO | WO 95/32184 | 11/1995 |
| WO | WO 95/32425 | 11/1995 |
| WO | 95/35278 | 12/1995 |
| WO | WO 96/21859 | 7/1996 |
| WO | WO 96/23749 | 8/1996 |

OTHER PUBLICATIONS

Boyce et al., 1994, "Peptidosteroidal Receptors for Opioid Peptides. Sequence–Selective Binding Using a Synthetic Receptor Library," *J. Am. Chem. Soc. 116*:7955–7956.

Brenner and Lerner, 1992, "Encoded combinatorial chemistry," *Proc. Natl. Acad. Sci. U.S.A. 89*:5381–5383.

Bunin and Ellman, 1992, "A General and Expedient Method for the Solid–Phase Synthesis of 1,4–Benzodiazepine Derivatives," *J. Am. Chem. Soc. 114*:10997–10998.

Bunin et al., 1994, "The combinatorial synthesis and chemical and biological evaluation of a 1,4–benzodiazepine library," *Proc. Natl. Acad. Sci. U.S.A. 91*:4708–4712.

Burbaum et al., 1995, "A paradigm for drug discovery employing encoded combinatorial libraries," *Proc. Natl. Acad. Sci. U.S.A. 92*:6027–6031.

Campbell et al., 1995, "A Transition State Analogue Inhibitor Combinatorial Library," *J. Am. Chem. Soc. 117*:5381–5382.

Carell et al., 1995, "New promise in combinatorial chemistry: synthesis, characterization, and screening of small–molecule librari s in solution," *Chemistry and Biology 2*:171–183.

Chabala, 1995, "Solid–phase combinat rial chemistry and novel tagging methods for identifying leads," *Current Opinion in Biotechnology 6*:632–639.

Chen et al., 1994, "'Analogous' Organic Synthesis of Small–Compound Libraries: Validation of Combinatorial Chemistry in Small–Molecule Synthesis," *J. Am. Chem. Soc. 116*:2661–2662.

Cho et al., 1993, "An Unnatural Biopolymer," *Science 261*:1303–1305.

Christian et al., 1992, "Simplified Methods for Construction, Assessment and Rapid Screening of Peptide Libraries in Bacteriophage," *J. Mol. Biol. 227*:2711–718.

Cwurla et al., 1990, "Peptides on phage: A vast library of peptides for identifying ligands," *Proc. Natl. Acad. Sci. U.S.A. 87*:6378–6382.

Desai et al., 1994, "Recent Advances in the Generation of Chemical Diversity Libraries," *Drug Development Research 33*:174–188.

Devlin et al., 1990, "Random Peptide Libraries: A Source of Specific Protein Binding Molecules,"*Science 249*:404–406.

DeWitt et al., 1993, "'Diversomers': An Approach to non–peptide, nonoligomeric chemical diversity," *Proc. Natl. Acad. Sci. U.S.A. 90*:6909–6913.

Ecker et al., 1993, "Rational screening of oligonucleotide combinatorial libraries for drug discovery," *Nucleic Acids Res. 21*:1853–1856.

Eichler et al., 1994, "Cyclic Peptide Template Combinatorial Libraries: Synthesis and Identification of Chymotrypsin Inhibitors," *Peptide Research 7*:300–307.

Ellman, 1996, "Design, Synthesis and Evaluation of Small–Molecule Libraries," *Acc. Chem. Res. 29*:132–143.

Erb et al., 1994, "Recursive deconvolution of combinatorial chemical libraries," *Proc. Natl. Acad. Sci. U.S.A. 91*:11422–11426.

Fodor et al., 1991, "Light–Directed, Spatially Addressable Parallel Chemical Synthesis," *Science 251*:767–773.

Freier et al., "Deconvolution of Combinatorial Libraries for Drug Discovery: A Model System," *J. Med. Chem. 38*:344–352.

Furka et al., 1991, "General method for rapid synthesis of multicomponent peptide mixtures," *Int. J. Peptide Protein Res. 37*:487–493.

Gallop et al., 1994, "Applications of Combinatorial Technologies to Drug Discovery. 1. Background and Peptide Combinatorial Libraries," *J. Med. Chem. 37*:1233–1251.

Geysen and Mason, 1993, "Screening chemically synthesized peptide libraries for biologically–relevant molecules," *Bioorganic & Medicinal Chemistry Letters 3*:397–404.

Geysen et al., 1987, "Strategies for epitope analysis using peptide synthesis," *Journal of Immunological Methods 102*:259–274.

Gordon et al., 1994, "Applications of Combinatorial Technologies to Drug Discovery. 2. Combinatorial Organic Synthesis, Library Screening Strategies, and Future Directions," *J. Med. Chem. 37*:1386–1401.

Han et al., 1995, "Liquid–phase combinatorial synthesis," *Proc. Natl. Acad. Sci. U.S.A. 92*:6419–6423.

Houghten, 1985, "General method for the rapid solid–phase synthesis of large numbers of peptides: Specificity of antigen–antibody interaction at the level of individual amino acids," *Proc. Natl. Acad. Sci. U.S.A. 82*: 5131–5135.

Houghten et al., 1991, "Generation and use of synthetic peptide combinatorial libraries for basic research and drug discovery," *Nature 354*:84–86.

Jacobs and Fodor, 1994, "Combinatorial chemistry — applications of light–directed chemical synthesis," *TIBTECH 12*:19–26.

Jung and Beck–Sickinger, 1992, "Multiple Peptide Synthesis Methods and Their Applications," *Angew. Chem. Int. Ed. Engl. 31*:367–383.

Kerr et al., 1993, "Encoded Combinatorial Peptide Libraries Containing Non–Natural Amino Acids," *J. Am. Chem. Soc. 115*:2529–2531.

Kick and Ellman, 1995, "Expedient Method for the Solid–Phase Synthesis of Aspartic Acid Protease Inhibitors Directed toward the Generation of Libraries," *J. Med. Chem. 38*:1427–1430.

Krchňák and Lebl, 1995, "Synthetic library techniques: Subjective (biased and generic) thoughs and views," *Molecular Diversity 1*:192–216.

Lam et al., 1991, "A new type of synthetic peptide library for identifying ligand–binding activity," *Nature 354*:82–84.

Latham et al., 1994, "The application of a modified nucleotide in aptamer selection: novel thrombin aptamers containing 5-(1-pentynyl)-2'-deoxyuridine," *Nucleic Acids Res. 22*:2817–2822.

Martin et al., 1995, "Measuring Diversity: Experimental Design of Combinatorial Libraries for Drug Discovery," *J. Med. Chem. 38*:1431–1436.

Moran et al., 1995, "Radio Frequency Tag Encoded Combinatorial Library Method for the Discovery of Tripetide-Substituted Cinnamic Acid Inhibitors of the Protein Tyrosine Phosphatase PTP1B," *J. Am. Chem. Soc. 117*:10787–10788.

Murphy et al., 1995, "Combinatorial Organic Synthesis of Highly Functionalized Pyrrolidines: Identification of Potent Angiotensin Converting Enzyme Inhibitor from a Mercaptoacyl Proline Library," *J. Am. Chem. Soc. 117*:7029–7030.

Needels et al., 1993, "Generation and Screening of an oligonucleotide-encoded sythetic peptide library," *Proc. Natl. Acad. Sci. U.S.A. 90*:10700–10704.

Nielson et al., 1993, "Synthetic Methods for the Implementation of Encoded Combinatorial Chemistry," *J. Am. Chem. Soc. 115*:9812–9813.

Nikolaiev et al., 1993, "Peptide-Encoding for Structure Determination of Nonsequenceable Polymers Within Libraries Synthesized and Tested on Solid-Phase Supports," *Peptide Research 6*:161–170.

Ohlmeyer et al., 1993, "Complex synthetic chemical libraries indexed with molecular tags," *Proc. Natl. Acad. Sci. U.S.A. 90*:10922–10926.

Ostresh et al., 1994, "'Libraries from libraries': Chemical transformation of combinatorial libraries to extend the range and repertoire of chemical diversity," *Proc. Natl. Acad. Sci. U.S.A. 91*:11138–11142.

Pease et al., 1994, "Light-generated oligonucleotide arrays for rapid DNA sequence analysis," *Proc. Natl. Acad. Sci. U.S.A. 91*:5022–5026.

Pinilla et al., 1994, "Investigation of antigen-antibody interactions using a soluble, non-support-bound synthetic decapeptide library composed of four trillion ($4 \times 10^{12}$) sequences," *Biochem. J. 301*:847–853.

Posner et al., 1994, "Catalytic antibodies: perusing combinatorial libraries," *TIBS 19*:145–150.

Scott, 1992, "Discovering peptide ligands using epitope libraries," *TIBS 17*:241–245.

Scott and Smith, 1990, "Searching for Peptide Ligands with an Epitope Library," *Science 249*:386–390.

Sepetov et al., 1995, "Library of libraries: Approach to synthetic combinatorial library design and screening of 'pharmacophore' motifs," *Proc. Natl. Acad. Sci. U.S.A. 92*:5426–5430.

Simon et al., 1992, "Peptoids: A modular approach to drug discovery," *Proc. Natl. Acad. Sci. U.S.A. 89*:9367–9371.

Staňkov àet al., 1994, "Application of One-Bead One-Structure Approach to Identification of Nonpeptidic Ligands," *Drug Development Research 33*:146–156.

Stephen and Lane, 1992, "Mutant Conformation of p53: Precise Epitope Mapping Using a Filamentous Phage Epitope Library,".

Wallace et al., 1994, "A Multimeric Synthetic Peptide Combinatorial Library," *Peptide Research 7*:27–31.

Wu et al., 1994, "Identifying Substrate Motifs of Protein Kinases by a Random Library Approach," *Biochemistry 33*:14825–14833.

Zuckermann et al., 1994, "Discovery of Nanomolar Ligands for 7-Transmembrane G-Protein-Coupled Receptors from a Diverse *N*-(Substituted)glycine Peptoid Library," *J. Med. Chem. 37*:2678–2685.

Tetrahedron Letters, 27:6319 (1986) Jean-Pierre Senet.

Kardiologisisa, "Bioeletrical Mechanism", 31(7):52–55 (1991).

Kardiologisisa, 30(8):69–72 (1990).

Aelony et al. *J. Hetegel Chem.*, "Aminimides IX(1). A general Synthesis of 1-Substituted-2-imidazolidinones(2)", 9:687–690 (1972).

Asscher, M., "Acyl Migration in 2-Hydroxylalkyl Aminimides", *J. Org. Chem.*, 41(4):715–716 (1976).

Aubry et al. "Experimental Conformational Study of Two Peptides Containing a-Aminoisobutyric Acid. Crystal Structure of N-Acetyl-a-aminoisobutyric Acid Methylamide", *Biopolymers*, 17:1693–1711 (1978).

Bapat et al., "Pyridines as Leaving Groups in Synthetic Transformations Nucleophilic Displacements of Amino Groups, and Novel Preparations of Nitriles and Isocyanates", *Tetrahedron Letters*, 31:2691–2694 (1976).

Barker, C. C., "The Dehydration and Racemisation of N-Acyl-L-aspartic Acids by Acetic Anhydride", University College, Hull, pp. 453–456 (1952).

Barta-Szalai et al., "Electron Deficient Heteroaromatic Ammonioamidates XVII. N-(3-Quinazolinio)amindates. VI. The Photochemistry of N-(30Quinazolinio)amidates in the Presence of βToluenethiol", *Acta Chem. Scand.* B 33(2) (1979).

Barta-Szalai et al., "Electron Deficient Heteroaromatic Ammonioamidates. Part 24. [1]N-(Quinazolin-3-io)amindates. Part 11.[2] The Photochemistry of N-(6, 7-Methylenedioxyquinazolin-3-io)amidates in Acetone", *J. Chem. Soc. Perkin Trans.* 1 (1983).

Batori et al. "Novel Synthesis of Pyrido[2,1-fl]-as-Triazinium System and its Zwitterionic Derivatives . . . ", *J. Heterocyclic Chem.* 23:375 (1986).

Batori et al. "Regioselectivity in Methylation and Phenylation of the Zwitterionic Pyrido[2,1-f]-as-triazinium-1-and 3-olates and thiolates[1]", *J. Heterocyclic Chem.* 25:437 (1988).

Batori et al., "Synthesis and Regiospecificity in Methylation of Pyrido[1,2-a]pyrazinium-1-and 3-olates and Pyrido[1, 2-b]pyridazinium-2-and 4-olates [1]", *J. Heterocyclic Chem.*, 27:1673 (1990).

Beck, William H., "The Basicities of Substituted N-Trimethylammoniophenylacetamidates and N-Trimethylammoniocinnamamidates. The Hammett Correlations and the Thermodynamics of Protonation", *J.C.S. Perkin II*, 1173 (1978).

Beck et al., "The Bacicities of Substituted N-Trimethylammoniophenylacetamidates and N-Trimethylammoniocinnamamidates. The Hammett Correlation and the Thermodynamics of Protonation", *J.C.S. Perkin II* (1976).

Benecke et al., "The Curtius Rearrangement in Aminimides", *Tetrahedron Letters*, 4:289–292 (1972).

Benedetti, Ettore, "Solid-State and Solution Conformation of Homo Oligo-β-aminoisobutyric acids) from Tripeptide to Pentapeptide: Evidence for a 310 Helix[1a]", *J. Am. Chem. Soc.* 104:2473–2444 (1982).

Benedetti et al., Folded and Extended Structures of Homooligopeptides from β,β-Dialkylated Glycines. A Conformational Energy Computation and X-ray Diffraction Study, *J. Am. Chem. Soc.* 106:8146–8152 (1984).

Benedetti et al., "First Crystal Structure Analysis of a Complete Homo–Oligopeptide Series", pp. 619–624.

Bettinetti et al., "Reazione dei diarildiazoalcani–Nota IV, Difenildiazometano e azoici carbonilici", *Gaza Chem. Ital.* 95 (1965).

Bobek et al., "Synthesis of N–Aminopyrazinium Analogs of Cytidine and 2'–Deoxycytidine", *Nucleotides & Nucleotides*, 10(8):1657–1665 (1991).

Bonora, Gian Maria, "Folded and Extended Structures of Homooligopeptides from α,α–Dialkylated α–Amino Acids. An Infrared Absorption and H Nuclear Magnetic Resonance Study", *J. Am. Chem. Soc.*, 106:8152–8156 (1984).

Bonora et al., "Synthesis of a Homologous Series of Protected Oligopeptides Derived From L–Norvaline", *Bull. Soc. Chim. Belg.*, 84(4):299–304 (1975).

Bosch et al., "(–)–Isovaline: Confirmation of its D–(= R)–Configuration by X–Ray Analysis of Its N–Chloroacetyl Derivative", *Tetrahedron* 38(24):3579–3583 (1982).

Boulton et al., "Allylic and Benzylic Deamination By Thermal Cleavage of 1–substituted 1,2–Dihydro–2, 4, 6–Triphenylpyridines", *Tetrahedron Letters* 31:2689–2690 (1976).

Boutis et al., "Observations on the Antineoplastic Activity of Aminimides", *Current Chemotherapy*, 11:1213–1216.

Bratchley et al., "Kinetics of Reaction Between Gaseous Oxygen and Cobalt(II) Amines", *Chemistry and Industry*, (1970).

Bregant and Poje, "New Cyclic Aminimides Containing Pyrazolone Skeleton", *Tetrahedron Letters*, 21:5059–5060 (1980).

Brown, Melancthon S., "Preparation of Some New Aminimides", *Journal of Chemical and Engineering Data*, 12(4).

Burgess et al., "An Obligatory a–Helical Amino Acid Residue", *Biopolymer*, 12:2599–2605 (1973).

Cameron, A.F., "Structural Investigations of Ylides. Part I. Crystal and and Molecular Structures of Trimethylammoniobenzamidate and Trimethylammonionitramidate: Two Stabilised Nitrogen–Nitrogen Ylides", *J. Chem. Soc.*, 1071–1076 (1972).

Cameron, A.F., "Crystal and Molecular Structures of Two N–Ammonio–amidates", *Chemical Communications*, 14:725–726 (1971).

Cates, Lindley, A., "2,2'–Phthaloyl–, 2,2'–Isophthaloyl–, and 2,2'–Terephthaloylbis[1,1,1–trimethylhydrazinium] Dihydroxie, Bis(Inner Salts): Synthesis, Partition Coefficients, Troxicity and Effect on Ganglionic Transmission", *Journal of Pharmaceutical Sciences*, 75(4):407–409 (1986).

Clarke et al., "Mosquito Larvicidal and Pupicidal Activity of Aminimides", *Chemical Abstracts*, 89:250 (1978).

Cleaver et al., "Synthesis of 2,2'–Bis–[5(4H)–oxazolones]", 77:1544–1546 (1954).

Colombo et al., "Pharmacological Properties of Besulpamide, a New Diruetic, in Rats and Dogs", *Meth and Final Exptl Clin Pharmacol*, 9(2):101–110 (1987).

The Crystal and Molecular Structure of the Amino Terminal Tetrapeptide of Alamethicin. A Novel $3_{10}$ Helical Conformation, *Biochemical and Biophysical Research Communications*, 79(1) (1977).

Corkill et al., "Light Scattering by Polydisperse Cylindrical Micelles", *Newcastle Technical Centre*, pp. 1274–1280 (1969).

Cuadro et al., "2–Alkoxycarbonylcycloimmonium Ylides, Efficient 1,4–Dipole Equivalents in the Synthesis of New Conjugated Betaines", *Tetrahedron*, 49(15):3185–3192 (1993).

Culbertson, B.M., "Aminimides. VI. Homo–and Copolymerization Studies on Trimethylamine Methacrylimide", *Journal of Polymer Science, Part A–1*, 6:363–373 (1968).

Culbertson, B.M., "Aminimides. IV. Homo–and copolymerizations Studies on 1,1–Dimethyl–1–(2–hyroxypropyl)amine–Methacrylimide . . . ", *Macromolecules*, 1:254 (1968).

Culbertson et al., "Aminimides. VIII Synthesis and Homo–and Copolymerization Studies of 1,11–Trimethylactrylylhydrazinium Chloride and 1,1,1–Trimethylactrylylhdrazinium chloride and 1,1,1–Trimethylmethacrylylhydrazinium Chloride", *Aminimides*, 3(6):715–722 (1970).

Culbertson et al., "Aminimides V. Preparation and Polymerization Studies of Trimethylamine–4–Vinylbenzimide", *Journal of Polymer Science*: Part A–1, 6:2197–2207 (1968).

Culbertson et al., "Synthesis and Polymerization Studies of aminimide Monomers containing Acetoxyl or Carboxylic Acid Residues", *Applied Polymer Symposium*, 26:399–410 (1975).

"Aminimides Cyclic", *J. Org. Chem*, USSR 2 (1966).

Delaney et al., "Sterically–Hindered Amino Acids, Directors of Peptide Conformation", *Proceedings of the Seventh American Peptide Symposium, Peptides–Synthesis–Structure–Function*, pp. 303–306.

Demestre et al., "Acute, Subacute and Subchronic Toxicity of Besulpamide", *Meth and Find Exptl Clin Pharmacol*, 9(2):111–119 (1987).

Dharanipraganda et al., "Asymmetric Synthesis of Unusual Amino Acids: An Efficient Synthesis of Optically Pure Isomers of β–Methylphenylalanine", *Tetrahedron*, 48(23):4733–4748 (1992).

Dias et al., "Ortho–Metallation Reactions with 1–Benzoyliminopyridinium Betaine", *Inorg. Nucl. Chem. Letters*, 10:233–235 (1974).

Dias et al., "Metal–Ylide Complexes. Part 1. Metallation Reactions . . . ", *J. Chem. Soc.*, 162 (1975).

Eiichi et al., "Synthesis of 1–alkyl–1, 1–dimethylhydrazinium salts and N–alkyldimethylaminoacetimides and Their Properties", *Chemical Abstracts*, 70:264 (1969).

Esteve, J., "Pharmacokinetics of Besulpamide in Rats and Dogs", *Meth and Find Exptl Clin Pharmacol*, 9(2):121–126 (1987).

Meerson et al., "Eliminations of Disturbances of the Heart Electric Stability and Arrhythmias with a Synthetic Analog of Acetylcholine", *Chemical Abstracts*, 115:44(1991).

Fazio et al., "Synthesis and Reactivity of Highly Versatile VDMO–VBC Copolymers", *Polymer Bulletin* 22, pp. 449–454 (1989).

Fetter, J., "N–(6,7–Methylenedioxy–3–Quinazolinio)Amidates–I Synthesis Spectra and Some Dark Reactions", *Tetrahedron*, 31:2559–2569 (1975).

Francis, A.K., "The Crystal Structure of a 310 Helical Decapeptide Containing α–Aminoisobutryic Acid", *FEBS Letters*, 155(2).

Francis, Athappilly K., "The Crystal Structure of the Amino–Terminal Pentapeptide of Suzukacillin. Occurrence of a Four–fold Peptide Helix", *J. Chem. Soc. Perkin Trans.* 11, 1235–1239 (1982).

Francis et al., "Crystal Structure of Boc–Ala–Aib–Ala–Aib–Aib–Methyl Ester, A Pentapeptide Fragment of the Channel–Forming Inonophore Suzukacillin", *Biopolymers*, 22:1499–1505 (1983).

Freeman et al., "Photochemistry of Trialkylammonio–N–benzoylimides: Rearrangement and Amide Formation", *J. Chem. Research* (S), 192–193 (1988).

Freeman et al., "Base–induced Rearrangement of 1,1,1, 2–Tetraethyl–2–benzoylhydrazinium Iodide to N–(Dimethylaminomethyl)–N–methylbenzamide", *J. Chem. Research* (S), 354–355 (1989).

Freis et al., "Aminimides XIII Long Chain aminimides and Isocyanates", *Journal of the American Oil Chemists' Society*, vol. 49.

Frigola et al., "Study of the Structure of Besulpamide, 1–[–Chloro–3–sulfamoylbenzoyl)amino]2,4,6–trimethylpyridinium Hydroxide Inner Salt, and Related Compounds, Using X–Ray Crystallography and 'H and $^{13}$C Nuclear Magnetic Resonance Spectroscopy", *J. Heterocyclic Chem.*, 26:1373–1382 (1989).

Fritchie et al., "The Crystal Structure of a Novel Heterocycle Containing an Intramolecular Carbon–Nitrogen Hydrogen Bond", *Chemical Communications*, 917–918 (1968).

Gal et al., "Basicity of the Carbonyl Group Part 6, Calorimetric and Spectro–metric Study of Complexation of para–substituted N–Ammoniobenz–amidates by Boron Trifluoride", *J.C.S. Perkins II*, p. 431 (1978).

Garland, "Studies on the Biologically–Active Conformations of Angiotensin", *Intra–Science Chemistry Reports*, 5(4):305–316 (1971).

Gibson et al., "Thermolysis of Trimethylamine–benzimide and Related Compounds: Identification of By–Products and their Probable Mechanism of Formation", *J. Chem. Soc* (C), pp. 2577–2580 (1967).

Godtfredsen et al., "The Reaction of Hydrazine with Cinnamic Acid Derivatives", *Acta Chem. Scand.* 9(9):1498–1509 (1955).

Haas et al., "Thermally Reversible Homopolymer Gel Systems", *Polymer Letters*, 2:1095–1096 (1964).

Hafner et al., "Beaktionen von Benzol–Derivaten Mit Nitrenen", *Tetrahedron Letters*, 26:1733–1737 (1964).

Hall, Iris H., "Hypolipidemic Activity of the Surfactants Aminimides, and Their Effects on Lipid Metabolism of Rodents", *Lipids*, 20(10):685–692 (1985).

Hardy et al., "Peptides Containing Dipropyglycine", *Int. J. Peptide Protein Res.*, 21:392–405 (1983).

Hart, R., "Syntheses des isocyanates de vinyle et d'isopropenyle", *Bull. Soc. Chim. Belg.*, 65:291–296 (1956).

Haywood et al., "Amine(polyfluoroalkoxyacyl)imide Surfactants[1]", *Journal of Fluorine Chemistry*, 51:419–431 (1991).

Heilmann et al., "The Chemistry of 2–Alkenyl–2–Oxazolin–5–Ones".

Heilmann et al., "Chemistry of Alkenyl Azlactones. IV. Preparation and Properties of Telechelic Acrylamides Derived from Amine–terminated Oligomers", *Journal of Polymer Science*, 22:3149–3160.

"Solid State and Solution Conformation of Homo Oligo (α–aminoisobutyric acids) from Tripeptide to Pentapeptide: Evidence for a $3_{10}$ Helix[1a]", *J. Am. Chem. Soc.*, 104:2437–2444 (1982).

Hinds, Mark G., "Synthesis, Conformational Properties, and Antibody Recognition of Peptides Containing β–Turn Mimetics Based on α–Alkylproline Derivatives", *J. Med. Chem.*, 34:1777–1789 (1991).

Howard et al., "Alkyl–(alkoxyalkyl–)hydrazones", *J. Org. Chem.*, 24(28):1825 (1959).

Hruby, Victor J., "Design of Drugs Acting at Peptidergic Receptors", *University of Arizona*, pp. 797–804.

Hruby et al., "Conformational and Dynamic Considerations in the Design of Peptide Hormone Analogs", *Biopolymers*, 22:517–530 (1983).

Hubner et al., "Syntheses und Reaktionen von 2–Alkenyloxazolonen", *Die Angewandte Makromolekulare Chemie* 11:109–124 (1970).

Huisgen et al., "Additionen mit Chinolinium–, Isochinolinium–und Phenanthridinium–N–imid", *Liebigs Ann. Chem.*, 506–527 (1977).

Ikeda et al., "Properties of 2–Hydroxyethylamine Acylimide Aqueous solution–Unusual Clouding Phenomenon", *Journalof the American Oil Chemists' Society*, vol. 55 (1978).

Ikeda et al., "Synthesis of 1,1,1–Tris(2–hydroxyethyl)-amine–2–acylimide", *Journal of the American Oil Chemists' Society*, vol. 53 (1976).

Ikeda et al., "The Mass Spectra of N–Acyliminopyridinium and Isoquinolinium Betaines", *Organic Mass Spectrometry*, 5:61–71 (1971).

Inokuma et al., "Synthesis, Surfactant Properties and Catalytic Action of Crown Ethers Bearing Aminimide Group", *The Chemical Society of Japan*, No. 3 (1982).

Inubushi et al., "Thermal Decomposition Behavior of Bis–aminimides and Their Application to Polymerization of Epoxide", *Journal of Polymer Science: Part A: Polymer Chemistry*, 25:1363–1382 (1987).

Inubushi et al., "Thermal Decomposition Behavior of Mono–aminimides and Their Application to Polymerization of Epoxide", *Journal of Polymer Science: Part A: Polymer Chemistry*, 25:137–150 (1987).

Inubushi et al., "Tough Epoxy Resins Cured with Aminimides", *Journal of Polymer Science, Part A: Polymer Chemistry*, 26:1779–1789 (1988).

Ip et al., "New Route to Cyclic Azomethine Imines", *Can. J. Chem.*, 52:3671–3675 (1974).

Iwakura et al., "Synthesis of N–[1–(1–Substituted 2–oxo-propyl)]acrylamides and –methacrylamides. Isolation and Some Reactions of Intermediates of the Dakin–West Reaction", *The Journal of Organic Chemistry*, (1966).

Jazwinski, J., "A multinuclear NMR Study on some Cyclic Aminimides and Related Compounds", *Journal of Molecular Structure*, 243:365–368 (1991).

Jung, G., "Stabilizing Effects of 2–Methylalaline Residues on β–Turns and α–Helixes", *Biopolymers*, 22:241–246 (1983).

Jung, Gunther, "Properties of the Membrane Modifying Polypeptide Antibiotics Alamethicin and Trichotoxin–40", Copyright 1981 by Walter de Gruyter Berlin, Structure and Activity of Natural Peptides.

Kabara et al., "Aminimides: II. Antimicrobial Effect of Short Chain Fatty Acid Derivatives", *Journal of the American Oil Chemists'Society*, 52 (1975).

Kakehi et al., "Synthesis and Characterization of 1–Imidoyliminopyridinium N–Ylides", *Chemistry Letters*, pp. 413–414 (1976).

Kameyama et al., "Reactive Surfactants. II. Synthesis of 2–acyl–1,1,1–trimethylhydrazinium Hydroxide Inner Salts and Their Properties", *Chemical Abstracts*, 72:45292–45293 (1970).
Kameyama et al., "Preparation and Some Properties of (2–Hydroxyalkyl)–dimethylammonium–N–acylimine", *Nippon*, 9:1789 (1974).
Kato et al., "Studies on Ketene and Its Derivatives. LXVIII Reaction of Kiketene with N–Imino–pyridinium,–quinolinium, and–isoquinolium Ylides", *Chem. Phar. Bull.*, 23:452–455 (1975).
Katritzky, Alan R., "The Structure of the Pyridine 1–Benzimide Mono Cation", *Gazzetta Chimica Italiana*, 117:509–511 (1987).
Katritzky, Alan R., "Conversions of Primary Amino Groups Into Other Functionality Mediated by Pyrylium Cations", *Tetrahedron*, 36:679–699 (1979).
Katritzky et al., "Heterocycles in Organic Synthesis. Part 17. Conversion of Primary Amines into Bromides and Chlorides", *J.C.S. Perkin I* (1979).
Katritzky et al., "Heterocycles in Organic Synthesis. Part 19, Thermolysis of Pyridinium N–Acylimines: a New Preparation of Isocyanates", *J.C.S. Perkin I* (1979).
Katritzky et al., "Heterocycles in Organic Synthesis. Part 16, The Conversion of Aliphatic, Aromatic, and Heteroaromatic Primary Amines into Iodides", *J.C.S. Perkin I* (1979).
Katritzky et al., "Heterocycles in Organic Synthesis. Part 24. A New Synthesis of NN'–Diarylcarbodi–imides", *J.C.S. Perkin I* (1979).
Katritzky et al., "Pyrylium Mediated Transformations of Primary Amino Groups into Other Functional Groups", *Angrew: Chem. Int. Ed. Engl.*, 23:420–429 (1984).
Katritzky et al., "Reactions of Pyryliums with Mono–and asym–Di–substituted Hydrazines", *J.C.S. Perkin I* 1495–1500 (1981).
Katritzky et al., "Pyrazolo(1,5–c)Pyrimidines from Pyrylium Salts and Amidrazones and Pyridine Imidoyl–N–Imides from Imidoyl Chlorides", *Heterocycles*, vol. 18 (1982).
Kazmierski et al., "Topographic Design of Peptide Neurotransmitters and Hormones on Stable Backbone Templates: Relation of Conformation and Dynamics to Bioactivity", *J. Am. Chem. Soc.*, 113:2275–2283 (1991).
Knapp, Spencer, "Relative Reactivity and Structures of Benozoyltrimethylhydrazine and 1–Benzoyl–2–methylpyrazolidine", *J. Org. Chem.*, 46:2490–2497 (1981).
Kondo et al., "Synthesis of Polymers Containing Pyridinium Ylide and Iminopyridinium Ylide Structure", *Journal of Polymer Science: Polymer Chemistry Edition*, 21:3597–3600 (1983).
Konig et al., Umlagerung von quartaren Allyl–, Benzyl–und Propargyl–hydraziniumsalzen *Chem. Berg.* 103:2052–2061 (1970).
Leibfritz, Dieter, "Syntheses von 2–Methylalanin–Peptiden, die pH–Abhangigkeit Ihrer $^{13}$C–NMR–Spektren und Eine Neue Methode Zur Auswertung uber CS–Diagramme", *Tetrahedron*, 38(14):2165–2181 (1982).
Lempert–Sreter et al., "Electron Deficient Heteroaromatic ammonioamides, $20^1$, N–(3–Quinazolinio)amidates, $8^1$", *Chemico scripta.*, 13:195–196 (1978–79).
Lempert–Sreter et al., "Electron Deficient Heteroaromatic Ammonioamides., etc.", *J. Chem. Soc. Perkin Trans.*, I (1983).
Leplawy et al., "Synthesis of Peptides Derived from Alpha–Methylalanine", *Tetrahedron*, 11:39–51 (1960).
Leueberger, Christian von, "18. Azimine. VI. [12]) 1–Alkoxycarbonyl–2,3–dialkyl–und–2,3–diaryl–azimine", *Helvetica Chimica Acta*, 65(18): Fasc. 1(1982).
Liebscher, Jurgen, "1–Amino–2–hydrazinopyrimidin–N–ylides. Unusual Tautomers of 1–Aminopyrimidin–2–hydrazones", Monatsche fur Chemie, 120:749–758 (1989).
Liler, Milica, "Mono–and Di–protonation Sites in N–Ammonio–amidates: a Spectroscopic Study", *J.C.S. Perkin, Trans* 2, 909–914 (1977).
Liler et al., "The Kinetics of Hydrolysis of N–Trimethylammonioacetamide and of substituted N–Trimethylammoniobenzamides in Concentrated Sulphuric Acid", *J.C.S. Perkins II*, 380(1980).
Liler et al., "Methylation and Protonation Sites in Some N–ammonioamidates", *J.C.S. Chem. Comm.*, 93–94 (1975).
Lockley, J.S., "A Convenient Thermal Route to N,N–Dialkylaminoisocyanates", *Tetrahedron Letters*, 30:2621–2624 (1974).
Lockley, J.S., "Cyclic Aminimides Containing the Pyrazolone Skeleton", *Tetrahedron Letters*, 48:4263–4266 (1974).
Lown et al., "Reaction of Diphenylcyclopropenethione with Pyridinium Imines", *Canadian Journal of Chemistry*, vol. 50 (1972).
Lwowski et al., "Cycloadditions of Aminoisocyanates to Heterocumulenes", *Tetrahedron Letters*, 5:425–428 (1971).
Marshall et al., "Angiotensin II –Studies on the Biologically Active Conformation", *Supplement II to Circulation Research*, vois. XXX and XXXI:143–150 (1972).
Matsueda et al., "Amine imides", *Plastics Manufacturing*vol. 83 (1975).
Mayr et al., "Die Kristallstruktur von α(tert–Butyloxycarbonylamino)–isobuttersaure", *Liebigs Ann. Chem.*, 715–724 (1980).
McKillip, William J., "Aminimides. I. A General Synthesis of Aminimides from Acyl Hydrazides and Their Pyrolysis", *Canadian Journal of Chemistry*, vol. 45 (1967).
McKillip, William J., "Aminimides. II. A One–Step Synthesis of Aminimides from Carboxylic Acid Esters", *Canadian Journal of Chemistry*, 45:2619–2622 (1967).
McKillip et al., "The Chemistry of Aminimides", *Chemical Reviews*, 73(3):255–281 (1973).
Meerson, F.Z., "Antiarrhythmic Effect of Adaptive Activation of the Vagal System and a New Synthetic Acetylcholine Analog", *Chemical Abstracts*, 114:40 (1991).
Mehta et al., "Synthesis of Aminimide Monomers and Polymers", *Journal of Polymer Science: Polymer Chemistry Edition*, 21:1159–1164 (1983).
Mierke et al., "Peptidomimetics in the Study of Opiate Peptides", *Structural Biology*, pp. 348–350.
Muthiah et al., "Copolymers of 2–Vinyl–4,4–Dimethylazlactone with Styrene and Ethyl α–Hydroxymethyacrylate", *Journal of Polymer Science: Part A: Polymer Chemistry*, 29:29–37 (1991).
Nagaraj et al., "Alamethicin, a Transmembrane Channel", *Ace. Chem. Res.*, 14:356–362 (1981).
Nagaraj et al., "Stereochemically Constrained Linear Peptides. Conformations of Peptides Containing α–Aminoisobutyric Acid", *J. Am. Chem. Soc.*, 101:1 (1979).
Nair et al., "Structure of a Peptide Oxazolone: 2–(1'–Benzyloxycarbonylamino–1'–methylethyl)–4, 4–dimethyl–5–oxazolone", *Acta Cryst.*, B36:1498–1500 (1980).

Nicolas, Ernesto, "Asymmetric Synthesis of Unusual Amino Acids: Synthesis of Optically Pure Isomers of α–methyltyrosine", *Tetrahedron Letters*, 30(49):6845–6848 (1989).

Niino et al., "Aminimide as Hardener/Curing Promoter for One Part Epoxy Resin Composition", *J. Applied Polymer Science*, 27:2361–2368 (1982).

Nitta, Yoshiro, "Pyridazine Derivatives IV. The Structures of Aminopyridazines", *Chem. Pharm. Bull.* 11:774–748 (1963).

Okamoto et al., "Reaction of N–Aminopyridinium Derivatives. II. The Reactions of 1–(N–Acylalkylamino)pyridinium Salt Derivatives with Cyanide Ion. (A New Synthesis of Primary Amines)", *Chem. Pharm. Bull.*, vol. 11 (1963).

Okamoto et al., "Reaction of N–Aminopyridinium Derivatives. V. Syntheses of 1–(N–Methylacetamido)alkylpyridinium Salts and their Reaction with Cyanide Ion", *Chem. Pharm. Bull.*, 14(5):518–523 (1966).

Ollis, W. David, "Heterocyclic Mesomeric Betaines", *Tetrahedron*, 41(12):2239–2329 (1985).

Paterson et al., "Sensitivity of Polypeptide Conformation to Geometry. Theoretical Conformational Analysis of Oligomers of–Aminoisobutyric Acid", *J. Am. Chem. Soc.*, 103(11):2948–2955 (1981).

Pellacani et al., "Degradation of Aminimides Obtained from Enamines and (Ehoxycarbonyl)nitrene", *J. Organic Chem.*, 47:5023–5025 (1982).

Peters et al., "Quantum Theory of the Structure and Bonding in Proteins", *J. Molecular Structure*, 86:341–347 (1982).

Pizzotti, Maddalena, "Reactions of 2–Azidopyridine and 1–Pyridinio Ylides with Transition–metal Complexes", *J.C.S. Dalton I*, p. 1155 (1978).

Potts et al., "Bridgehead Nitrogen Heterocycles. I. A Convenient Synthesis of Pyrazolo[1,5–a]pyridines", *J. Organic Chem.*, vol. 33, No. 10 (1968).

Prasad et al., "Molecular Structure of Boc–Aib–Aib–Phe–Met–$NH_2$ DMSO. A Fragment of a Biologically Active Enkephalin Analogue", *J. Chem. Soc. Perkin Trans*, 1:417–421 (1983).

Ramakrishnan, V.T., "Cyclic Aminimides Containing the 3–oxo–5–Thioxo–1,2,4–Triazolidine Skeleton: Rearrangements of 5–Thiourazole Derivatives", *Tetrahedron Letters*, 37:3249–3252 (1974).

Rao et al., "Hydrophobic Channels in Crystals of an χ–Aminoisobutyric Acid Pentapeptide", *Biochem. & Biophys. Res. Comm.*, 103(3):898–904 (1981).

Rao et al., "Molecular Structure of t–Butyloxycarbonyl–Leu–Aib–Pro–Val–Aib–Methyl Ester, a Fragment of Alamethicin and Suzukacillin: a $3_{10}$–Helical Pentapeptide", *Biopolymers*, 21:2461–2472 (1982).

Rasmussen et al., "Multiazlactones—Potential Alternatives to Isocyanate and Epoxy Resins", pp. 33–34.

Rasmussen et al., "Chemistry of Alkenylazlactones,2[a)] Reaction with thiols", *Makromol. Chem. Rapid Comm.*, 5:67–70 (1984).

Redda, Kinfe K., "Synthesis of Some N–[Pyridyl(phenyl) carbonylamino]–alkyl–1,2,3,6–tetrahydropyridines", *J. Heterocyclic Chem.*, 27:1041 (1990).

Redda et al., "Syntheses of N–Substituted 2(3,4)–Pyridylcarboxylic Acid Hydrazides with Analgesic and Antiinflammatory Activity", *J. Med. Chem.*, 22(9):1079 (1979).

Redda et al., "Synthesis and Pharmacological Evaluation of Some N–[Pyridyl(phenyl)carbonylamino]methyl–1,2,3,6–tetrahydropyridines", *J. Pharmaceutical Sciences*, vol. 81, No. 5 (1992).

Redda et al., "Synthesis and Anti–inflammatory Activities of Some N–[Pyridyl(penyl)carbonylamino]–tert–butyl/phenyl–1,2,3,6–tetrahydropyridines", *Chem. Pharm. Bull.*, 39(3):786–791 (1991).

Fox, Jr., et al., "A voltage–gated ion channel model inferred from the crystal structure of alamethicin at 1.5–A resolution", *Nature*, 300:325–330 (1982).

Riemer et al., "Electrophilic Amination of Pyrimidine–2–thiones–Synthesis of Zwitterionic 2–Aminothiopyrimidinium–N–ylides, Pyrimidine–2–ones and Bicyclic Pyrimidinium Compounds", *Tetrahedron*, 49(18):3767–3780 (1993).

Van Roey et al., "Crystal and molecular structure of tert.–butyloxycarbonyl–L–hydroxy–prolyl–α–aminoisobutyryl–α–aminoisobutryl–L–phenylalaninol", *Int. J. Peptide Protein Res.*, 19:499–505 (1982).

Roques, Bernard P., "Peptidomimetics as Receptors Agonists or Peptidase Inhibitors: A Structural Approach in the Field of Enkephalins, ANP and CCK", *Biopolymers*, 32:407–410 (1992).

Jacques et al., "Regiospecific Versus Non–Regiospecific Photoinduced Ring–Enlargement of 3–Substituted 1–Iminopyridinium Ylides", *Tetrahedron Letters*, 52:4859–4862 (1976).

Salazar et al., "Synthesis and Spectroscopic Studies of 2–(1,1–Dimethylhydrazono)propyl Phosphonates", *M.R. Chemistry*, 20:471–474 (1988).

Sasaki et al., "The Chemistry of Diazepines. The Photochemical Intramolecular 1,3–Dipolar Cycloaddition of Substituted 1–Ethoxycarbonyliminopyridinium Ylides", *J. Organic Chem.*, vol. 35, No. 2 (1970).

Schiessl et al., "A Novel Synthesis of 1,5–Diphenylpyrazolone–3", *J. Chemistry*, 31:3851–3852 (1966).

Schmidbaur et al., "Polyspirocyclische Komplexe des Palladiums mit Phosphor–Yliden", *J. Prakt. Chem.*, 2(110):204 (1925).

Schmitt, Heribert, "The α–Helical Conformation of the Undecapeptide Boc–L–Ala–[Aib–Ala]$_2$–Glu(OBzl)–Ala–[Aib–Ala]$_2$–OMe: Synthesis, X–Ray Crystal Structure, and Conformation in Solution", *Liebigs Ann. Chem*, pp. 1304–1321 (1982).

Schollkopf, Ulrich, "Asymmetric Synthesis of Boc–L–Val–(R)–α–MePro–OMe, Boc–L–Val–(R)–Proome, and of Boc–L–Val–(R)–α–MePhe–OMe, Ac–L–Val–(R)–α–MePhe–OMe and Their Analogues. A New Strategy for the Synthesis of Non–Proteinogenic Dipeptides", *Liebigs Ann. Chem.*, pp. 1025–1031 (1988).

Schollkopf, Ulrich, "Asymmetric Syntheses via Heterocyclic Intermediates; VIII. Enantioselective Synthesis of (R)–α–Methyl–α–amino Acids using L–Valine as Chiral Auxiliary Reagent", *Communications*, pp. 969–971 (1981).

Schollkopf et al., "Asymmetrische Syntheses von x–Alkyl–x–aminocarbon–sauren durch Alkylierung von 1–chiral–substituierten 2–Imidazonin–5–onen", *Angew. Chem.*, 90(2):136–138 (1978).

Schollkopf et al., "Enantioselective Synthesis of α–Methyl–α–aminocarboxylic Acids by Alkylation of the Lactim Ether of Cyclo–(I–ala–I–Ala)", *Angew. Chem. Int. Ed. Engl.*, vol. 18, No. 11 (1979).

Schulten, H. R., "Applications of Field Desorption Mass Spectrometry in Inorganic Chemistry: Salts", *Angew. Chem. Int. Ed.*, vol. 14, No. 8 (1975).

Semenov et al., "Reaction of Acyl Nitrenes with Unsaturated Compounds", *J. Org. Chem. USSR*, 13:885 (1977).

Senet, Jean–Pierre, "Cyclic Carbalkoxy Aminimides. Synthesis and Thermal Decomposition To Give N,N–Dimethylamino Isocyanate", *Tetrahedron Letters*, 27(52):6319 (1986).

Seoh, Sang–Ah, "The permeation properties of small organic cations in gramicidin A channels", *Biophy. J.*, 64:1017–1028 (1993).

Shamala et al., "The $3_{10}$ Helical Conformation of a Pentapeptide Containing a–Aminoisobutyric Acid (Aib): X–Ray Crystal Structure of Tos–$(Aib)_5$–OMe", *J.C.S. Chem. Comm.*, pp. 996–997 (1978).

Shamala et al., "The Crystal Molecular Structure of the Amino Terminal Tetrapeptide of Alamethicin. A Novel 310 Helical Conformation", *Biochem. & Biophys. Res. Comm.*, vol. 79, No. 1 (1977).

Shutenko et al., "Regulation of carnitive–dependent metabolism of fatty acids in myocardium under the influence of 3–(2,2,2–tri–methylhydrazinium)propionate", *I–Pharmacology*, 108:31589 (1988).

Shutenko et al., "Regulation of the carnitive–dependent metabolism of fatty acids in the rat myocardium", *Chemical Abstract*, 115:45 (1991).

Slagel, R.C., "Aminimides. VI. Synthesis of Aminimides from Carboxylic Acid Esters, Unsymmetrically Disubstituted Hydrazines, and Epoxides", *J. Organic Chem.*, vol. 33, No. 4 (1968).

Slagel et al., "Aminimides. III. A convenient synthesis of isopropenyl isocyanate", *Canadian Journal of Chemistry*, 45:2625 (1967).

Small, Robert J., "Preparation of 2–Hydroxyethyldimethylamine Acylimides", *Organic Preparations and Procedures Int.*, 13(1):55–58 (1981).

Smith, Richard F., "Reactions of Hydrazines with Esters and Carboxylic Acids", *J. Organic Chem. –Notes*, pp. 851–855.

Smith, Richard F., "Reaction of 1,1–Dibenzoyl–2,2–dimethylhydrazine with Methyl p–Toluenesulfonate", *J. Organic Chem.*, 41(9):1555–1556 (1976).

Smith, G. David, "Crystal Structures and Conformational Calculations of Fragments of Alamethicin Containing Aminoisobutyric", *J. Am. Chem. Cos.*, 103:1493–1501 (1981).

Smith, Richard F., "The Pyrolysis and Photolysis of Trimethylamine Benzimide", *Chemical Communications*, p. 120 (1965).

Smith et al., "Stevens Rearrangement of Carbamoylaminimides", *J. Organic Chem.*, vol. 59, No. 14 (1974).

Smith et al., "Nitroative Cleavage of N,N–Dialkyhydrazides and Tertiary Amines", Chemistry Department of the University of Michigan, vol. 24, pp. 1325–1332 (1959).

Streith et al., "No. 382 –Syntheses Photochimique de (1–H)–Diazepines–1,2", *Bull. Soc. Chem., France* 6:2175–2179 (1969).

Sucrow et al., "Pyrazolium–Betaine aus 1, 1–Dialkylhydrazinen und Acetylencarbonsaureestern", *Chem. Ber. III*, pp. 780–790 (1978).

Takeuchi et al., "Novel–Heterocyclic Syntheses from Azomethine Imides. 2–Unsubstituted Diazetidinones", *J. Am. Chem. Soc.*, 90:19 (1968).

Tamura et al., "1,3–dipolar Cycloaddition Reaction of 1–Methylperimidine 3–Ylides with Dimethyl Acetylenedierboxylate", *Chem. Pharm. Bull.*, 31:1378–1381 (1983).

Tamura et al., "Synthesis of 3–substituted N–Aminopyridinium Salts(1)", *J. Heterocyclic Chem.*, 9:865 (1972).

Tamura et al., "Synthesis and Thermal Reaction of 2,2–Diacyl–N–(1–pyridinio)vinyl–aminides: Formation of Pyrazolo[1,5–a]pyridines and Isoxazoles", *J.C.S. Perkin I*, pp. 2580–2583 (1973).

Tamura et al., "The Photo Arrangement and Thermolysis of N–Benzoylimino–isoquinolinium and Quinolinium Betaines", *Chem. Pharm. Bull.*, 19(6):1285–1286 (1971).

Taylor et al., "A convenient synthesis of 5–oxazolones. 2–phenyl–5–oxazolone", *Organic Preparations and Procedures*, 1(3):217–219 (1969).

Taylor et al., "The Synthesis of Vinyl Peptide Monomers", *Polymer Letters*, 7:597–603 (1969).

Taylor et al., "A Polymer whose Aqueous Solutions Show the Properties of Negative Thixotropy and Thermoreversible Gelation: (Poly–(Trimethylamine p–Vinylbenzimide)", *J. Polymer Science: Part C: Polymer Letters*, 24:287–289 (1986).

Taylor et al., "A convenient Synthesis of 5–oxazolones. 2–Phenyl–5–oxazolone", *Organic Preparations and Procedures*, 1(3):217–219 (1969).

Taylor et al., "Synthesis of Poly(4,4–dimethyl–2–vinyl–5–oxazolone) an Interesting Material for Preparing Polymeric Agents", *Makromol Chem. Rapid Commun.*, 3:779–782 (1982).

Taylor et al., "Synthesis and Polymerization of 2–vinyl–4, 4–Dimethyl–5–Oxazolone", *Polymer Letters*, 9:187–190 (1971).

Throckmorton et al., "Halogen–containing Aminimide Compounds as Tire Cord Adhesives", *Rubber Chem. Technology*, p. 53 (1980).

Tichniouin et al., "Aminimides ethyleniques a action vasodilatatrice peripherique", *Eur. J. Med. Chem. Chem. Ther.*, 17(3):265–270 (1982).

Tikdari et al., "Reactions of Some 1,3–Diaminonucleophiles with Azlactones", *J. Chem. Soc. Perkin Trans.*, (1988).

Toniolo et al., "Bioorganic stereochemistry", *Int. J. Peptide Protein Res.*, 22:603–610 (1983).

Toniolo et al., "Preferred Conformations of Peptides Containing α, α–Disubstituted α–Amino Acids", *Biopolymers*, 22:205–215 (1983).

Tshuchida et al., "Reaction of Ethyl Aziodoformate with Morpholines", *Bull. Chem. Soc. Japan*, 53:1149 (1980).

Shinji, "Evidence for Amide Resonance observed in Cyclic N–Ammonio–imitates by X–Ray Photoelectron Spectroscopy", *J. Chem. Soc. Chem. Commun.*, pp. 875–876 (1982).

Tsuchiya, Shinji, "On the Nature of Nitrogen–Nitrogen Bonding in Cyclic Aminimides", *J. Chem. Soc. Perkin Trans.*, p. 11 (1993).

Tsuchiya et al., "Thermal Rearrangements of cyclic Amine Ylides. III. Intramolecular Cyclization of 2–Ethynylpyridine N–Imides to 3–Azaindolizine Derivatives", *Chem. Pharm. Bull.* 31(12):4568–4572 (1983).

Tsuchiya et al., "On the Bond Character of N–Containing Ylides", *J. Organic Chem.*, 44(16):2850–2855 (1979).

Tsuchiya et al., "Studies on Diazepines. XVIII. Photochemical Synthesis of 3H–1,3–Benzodiazepines from Quinoline N–Acylimides Diels–Alder Cycloaddition Reactions", *Bull. Chem. Soc. Japan.*, p. 2073 (1983).

Tsuge et al., "Double Cycloaddition Reaction of Imidazolium Methylides. Intermolecular 1,3–Dipolar and Intramolecular Diels–Alder Cycloaddition Reactions", *Bull. Chem. Soc. Japan*, p. 2073 (1983).

Venkatachalapathi et al., "X–Pro Peptides: Solution and Solid–State Conformation of Benzyloxycarbonyl–(Aib–Pro)$_2$–methyl Ester, a Type 1 β–Turn", *Biopolymers*, 20: 1123–1136.

Wadsworth, Jr., William S., "Cyclic Aminimides", *J. Chemistry*, 31:1704–1707 (1966).

Wawzonek, S., "The Rearrangement of 1,1–Dimethyl–1–p–nitrobenzylamine–2–acetamide", *J. Am. Chem. Soc.*, 82:5718–5721 (1960).

Wawzonek et al., "The Resolution of 1–Ethyl–1–methyl–1–p–nitrobenzylamine–2–acetamide", *J. Chemistry*, 28:2376–2377 (1963).

Wawzonek et al., "The Rearrangement of 1–Methyl–1–acetylimide–2–phenylpyrrolidine", *J. Organic Chem.*, pp. 3031–3033 (1965).

Wawzonek et al., "Electrolytic Preparation of bis–Dimethyl–2–Hydroxypropylamineazobenzimides", *Organic Preparations and Procedures Int.*, 8(5):215–217 (1976).

Wright et al., "Central Nervous System Depressants. I. 1–Aminoalkyl–3–aryl Derivatives of 2–Imidazolidinone, 2–Imidazolidinethione, and Tetrahydro–2(1H)–pyrimidinone", *J. Med. Chem.*, 9:852–857.

Yeung, Jupita M., "Synthesis of N–[[(Substituted–phenyl) carbonyl]amino]–1,2,3,6–tetrahydropyridines with Analgesic and Hyperglycemic Activity", *J. Med. Chem.*, 25:720–723 (1982).

Yeung et al., "Synthesis of N–(3,6–Dihydro–1(2H)–pyridinyl)benzamides with Hyperglycemic–Hypoglycemic Activity", *J. Med. Chem.*, 30:104–108 (1987).

Yeung et al., "Synthesis of N–(Carbonylamino)–1,2,3,6–tetrahydropyridines with Analgesic, Antiinflammatory, and Hyperglycemic Activity", *J. Med. Chem.*, 25:191–195 (1982).

U.S. Appl. No. 08/092,862, Armstrong, filed Jul. 1993.

Armstrong et al., "Acetylenic beta–linked C–oligosaccharides as distance spacers and probes of biopolymer interactions", Abstracts of Papers American Chemical Society, (1993) vol. 206, No. 1–2, pp. ORGN 102, 206$^{th}$ ACS (American Chemical Society) National Meeting (Aug. 22–27, 1993).

Armstrong et al., "Analogs of the azinomycins: Selective acetylation via orthoacetate hydrolysis", Abstracts of Papers American Chemical Society, (1993) vol. 206, No. 1–2, pp. ORGN 366, 206$^{th}$ ACS (American Chemical Society) National Meeting (Aug. 22–27, 1993).

Armstrong et al., "Synthesis of the azinomycin A framework", Abstracts of Papers American Chemical Society, (1993) vol. 206, No. 1–2, pp. ORGN 101, 206$^{th}$ ACS (American Chemical Society) National Meeting (Aug. 22–27, 1993).

Bray, Andrew M., et al., "The Simultaneous Multiple Production of Solution Phase Peptides; Assessment of the Geysen Method of Simultaneous Peptide Synthesis.", Tetr. Lett. 31(40): 5811–5814 (1990).

Combs et al., "Highly convergent synthesis of azinomycin analogs via Passerini reactions of vinylaziridine isocyanides", Abstracts of Papers American Chemical Society, (1993) vol. 206, No. 1–2, pp. ORGN 367, 206$^{th}$ ACS (American Chemical Society) National Meeting (Aug. 22–27, 1993).

Combs, Andrew Paul, Abstract of thesis entitled "Syntheses and structure–activity relationship analyses of dehydroamino acid derivatives related to the azinomycins", University of California, Los Angeles (1994).

Combs, Andrew Paul, Thesis entitled "Syntheses and structure–activity relationship analyses of dehydroamino acid derivatives related to the azinomycins", University of California, Los Angeles (1994).

Blondelle et al., Abstract of "Development of New Antimicrobial Peptides Using Synthetic Peptide Combinatorial Libraries Containing Unnatural Amino Acids".

Conference: "Exploiting Molecular Diversity Combinatorial Libraries for Drug Discovery", San Diego, CA, Cambridge Healthtech Institute (Jan. 12–14, 1994), including presentation by Robert Armstrong.

Dooley et al., Abstract of "New, Potent N–Acetylated L–and D–Amino Acid Opioid Peptides".

Eichler et al., Abstract of "Identification of Trypsin–Inhibiting All D–Amino Acid Peptides Through the Screening of a Synthetic D–Amino Acid Peptide Library".

Garr et al., Abstract of "Current Technology Applied to Established Chemical Knowledge: A Novel Approach to Small Molecule Chemical Libraries" (Dec. 13, 1993).

Harn et al., Abstract of "Thiomethylene Arg–Gly–Asp Pseudotripeptides for Solid Phase Synthesis".

Houghten, Richard A., "The broad utility of soluble peptide libraries for drug discovery", Gene 137:7–11 (1993).

Ohlmeyer et al., Abstract of "Combinatorial Libraries Encoded with Molecular Tags".

Pavia, Michael R., et al. "The generation of molecular diversity", Bioorg. Med. Chem. Lett., 3(3) 387–396 (1993).

Pinilla et al., Abstract of "A Soluble Synthetic Decapeptide Library Composed to Four Trillion Sequences for the Study of Antigen–Antibody Interactions".

Romanovskis, Peteris et al., Abstract of "Cyclic Peptide Libraries: Recent Developments".

Shikhman et al., Abstract of "Cytokeratin peptides mimic N–acetyl–β–D–glucosamine in reactions with antibodies and lectins".

Sprague, P. W., Abstract of "Analysis of Structure Activity Data with Catalyst".

Zuckermann, Ronald N., "The chemical synthesis of peptidomimetic libraries", Curr. Opin. Str. Bio., 3:580–84 (1993).

Supplementary European Search Report issued by the European Patent Office, May 24, 2004.

Conference: "Exploiting Molecular Diversity: Small Molecule Libraries for Drug Discovery," Cambridge Healthtech Institute (Jan. 23–25, 1995).

Culbertson et al., "Aminimides. XII. Synthesis, Homo–and Copolymerication Studies of Trialkylamine N–Acryloyl or N–Methacryloyl Glycinimides and β–Aminopropanimides," *Polymer Science: Part A*–1, 9:3453–3470 (1971).

Liler and Morris, "Mono–and Di–protonation Sites in N–Ammonio–amidates: a Spectroscopic Study," *J. Chem. Soc., Perkin II*, pp. 909–914 (1977).

Garr, Cheryl D., "Solution Phase Synthesis of Chemical Libraries for Lead Discovery," *Journal of Biomolecular Screening*, 1 (4): 179–186 (1996).

Smith, Paul W., "Synthesis and Biological Evaluation of a Library Containing Potentially 1600 Amides/Esters. A Strategy for Rapid Compound Generation and Screening," *Bioorganic & Medicinal Chemistry Letters*, 4 (24): 2821–2824 (1994).

LOGICALLY ORDERED ARRAYS OF COMPOUNDS AND METHODS OF MAKING AND USING THE SAME

CROSS-REFERENCE TO RELATED APPLICATIONS

This application is a continuation of U.S. application Ser. No. 08/375,838, filed Jan. 20, 1995, now U.S. Pat. No. 5,712,171, the content of which is incorporated herein in its entirety by reference.

BACKGROUND OF THE INVENTION

The discovery of new molecules has traditionally focused in two broad areas, biologically active molecules, which are used as drugs for the treatment of life-threatening diseases, and new materials, which are used in commercial, especially high technological applications. In both areas, the strategy used to discover new molecules has involved two basic operations: (i) a more or less random choice of a molecular candidate, prepared either via chemical synthesis or isolated from natural sources, and (ii) the testing of the molecular candidate for the property or properties of interest. This discovery cycle is repeated indefinitely until a molecule possessing the desirable properties is located. In the majority of cases, the molecular types chosen for testing have belonged to rather narrowly defined chemical classes. For example, the discovery of new peptide hormones has involved work with peptides; the discovery of new therapeutic steroids has involved work with the steroid nucleus; the discovery of new surfaces to be used in the construction of computer chips or sensors has involved work with inorganic materials, etc. (for example, see R. Hirschmann, *Angew. Chem., Int. Ed. in Engl.* 1991, 30, 1278–1301). As a result, the discovery of new functional molecules, being, ad hoc in nature and relying predominantly on serendipity, has been an extremely time-consuming, laborious, unpredictable, and costly enterprise.

A brief account of the strategies and tactics used in the discovery of new molecules is described below. The emphasis is on biologically interesting molecules. However, as discussed below, there are technical problems encountered in the discovery of molecules and in the development of fabricated materials which can serve as new materials for high technological applications.

Modern theories of biological activity state that biological activities, and therefore physiological states, are the result of molecular recognition events. For example, nucleotides can form complementary base pairs so that complementary single-stranded molecules hybridize resulting in double- or triple-helical structures that appear to be involved in regulation of gene expression. In another example, a biologically active molecule, referred to as a ligand, binds with another molecule, usually a macromolecule referred to as ligand-acceptor (e.g. a receptor or an enzyme), and this binding elicits a chain of molecular events which ultimately gives rise to a physiological state, e.g. normal cell growth and differentiation, abnormal cell growth leading to carcinogenesis, blood-pressure regulation, nerve-impulse-generation and -propagation, etc. The binding between ligand and ligand-acceptor is geometrically characteristic and extraordinarily specific, involving appropriate three-dimensional structural arrangements and chemical interactions.

Design and Synthesis of Mimetics of Biological Ligands

A currently favored strategy for development of agents which can be used to treat diseases involves the discovery of forms of ligands of biological receptors, enzymes, or related macromolecules, which mimic such ligands and either boost (i.e., agonize) or suppress (i.e., antagonize) the activity of the ligand. The discovery of such desirable ligand forms has traditionally been carried out either by random screening of molecules (produced through chemical synthesis or isolated from natural source's, for example, see K. Nakanishi, *Acta Pharm. Nord.*, 1992, 4, 319–328.), or by using a so-called "rational" approach involving identification of a lead-structure, usually the structure of the native ligand, and optimization of its properties through numerous cycles of structural redesign and biological testing (for example see Testa, B. & Kier, L. B. *Med. Res. Rev.* 1991, 11, 35–48 and Rotstein, S. H. & Murcko, M. A. *J. Med. Chem.* 1993, 36, 1700–1710.). Since most useful drugs have been discovered not through the "rational" approach but through the screening of randomly chosen compounds, a hybrid approach to drug discovery has recently emerged which is based on the use of combinatorial chemistry to construct huge libraries of randomly-built chemical structures which are screened for specific biological activities. (Brenner, S. & Lerner, R. A. *Proc. Natl. Acad. Sci. USA* 1992, 89, 5381)

Most lead-structures which have been used in "rational" drug design are native polypeptide ligands of receptors or enzymes. The majority of polypeptide ligands, especially the small ones, are relatively unstable in physiological fluids, due to the tendency of the peptide bond to undergo facile hydrolysis in acidic media or in the presence of peptidases. Thus, such ligands are decisively inferior in a pharmacokinetic sense to nonpeptidic compounds, and are not favored as drugs. An additional limitation of small peptides as drugs is their low affinity for ligand acceptors. This phenomenon is in sharp contrast to the affinity demonstrated by large, folded polypeptides, e.g., proteins, for specific acceptors, e.g., receptors or enzymes, which can be in the subnanomolar range. For peptides to become effective drugs, they must be transformed into nonpeptidic organic structures, i.e., peptide mimetics, which bind tightly, preferably in the nanomolar range, and can withstand the chemical and biochemical rigors of coexistence with biological fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign-synthesis-screening cycles, peptidic ligands belonging to a certain biochemical class have been converted by groups of organic chests and pharmacologists to specific peptidomimetics; however, in the majority of cases the results in one biochemical area, e.g., peptidase inhibitor design using the enzyme substrate as a lead, cannot be transferred for use in another area, e.g., tyrosine-kinase inhibitor design using the kinase substrate as a lead.

In many cases, the peptidomimetics that result from a peptide structural lead using the "rational" approach comprise unnatural amino acids. Many of these mimetics exhibit several of the troublesome features of native peptides (which also comprise alpha-amino acids) and are, thus, not favored for use as drugs. Recently, fundamental research on the use of nonpeptide scaffolds, such as steroidal or sugar structures, to anchor specific receptor-binding groups in fixed geometric relationships have been described (see for example Hirschmann, R. et al. *J. Am. Chem. Soc.* 1992, 114, 9699–9701; Hirschmann, R. et al., *J. Am. Chem. Soc.*, 1992, 114, 9217–9218); however, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, called "peptoids", which are screened for a desirable biological activity (see Gordon, E. M. et al. *J. Med. Chem.* 1994, 37, 1385–1401). For example, the method of H. M. Geysen, (*Bioorg. Med. Chem. Letters*, 1993, 3, 397–404*; Proc. Natl. Acad. Sci. USA* 1984, 81, 3998) employs a modification of Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. Houghton, (*Proc. Natl. Acad. Sci. USA* 1985, 82, 5131; Eichler, J. & Houghton, R. A. *Biochemistry*, 1993, 32, 11035–11041, and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. S. P. A. Fodor et al., (Science 1991, 251, 767) described light-directed, spatially addressable parallel-peptide synthesis on a silicon wafer to generate large arrays of addressable peptides that can be directly tested for binding to biological targets. These workers have also developed recombinant DNA/genetic engineering methods for expressing huge peptide libraries on the surface of phages (Cwirla et al. *Proc. Natl. Acad. Sci. USA* 1990, 87, 6378; Barbas, et al. *Proc. Natl. Acad. Sci. USA* 1991, 881, 7978–7982).

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing numbers of peptides were produced in uniform amounts which were then separately screened for a biological activity of interest.

Zuckermann and coworkers (For examples, see Zuckermann, et al. *J. Med. Chem.* 1994, 37, 2678–2685 & Zuckermann, et al. *Int. J. Peptide Protein Res.* 1992, 91, 1) also have developed similar methods for the synthesis of peptide libraries and applied these methods to the automation of a modular synthetic chemistry for the production of libraries of N-alkyl glycine peptide derivatives, called "peptoids", which are screened for activity against a variety of biochemical targets. (See also, Symon et al., *Proc. Natl. Acad. Sci. USA*, 1992, 89, 9367). Encoded combinatorial chemical syntheses have been described recently (Brenner, S. & Lerner, R. A. *Proc. Natl. Acad. Sci. USA* 1992, 89, 5381; Barbas, C. F. et al. *Proc. Natl. Acad. Sci. USA* 1992, 89, 4457–4461; see also Borchardt, A. & Still, W. C. *J. Am. Chem. Soc.* 1994, 116, 373–374; Kerr, J. et al. *J. Am. Chem. Soc.* 1993, 115, 2529–2531).

M. J. Kurth and his group (Chen, C. et al. *J. Am. Chem. Soc.* 1994, 116, 2661–2662.) have applied organic synthetic strategies to develop non-peptide libraries synthesized using multi-step processes on a polymer support. Although the method demonstrates the utility of standard organic synthesis in the application and development of chemical libraries, the synthetic conditions are limited by compatibility with the solid support.

The development of substrates or supports to be used in separations has involved either the polymerization/crosslinking of monomeric molecules under various conditions to produce fabricated materials such as beads, gels, or films, or the chemical modification of various commercially available fabricated materials e.g., sulfonation of polystyrene beads, to produce the desired new materials. In the majority of cases, prior art support materials have been developed to perform specific separations or types of separations and are thus of limited utility. Many of these materials are incompatible with biological macromolecules, e.g., reverse-phase silica frequently used to perform high pressure liquid chromatography can denature hydrophobic proteins and other polypeptides. Furthermore, many supports are used under conditions which are not compatible with sensitive biomolecules, such as proteins, enzymes, glycoproteins, etc., which are readily denaturable and sensitive to extreme pH's. An additional difficulty with separations carried out using these supports is that the separation results are often support-batch dependent, i.e. they are irreproducible.

Recently a variety of coatings and composite-forming materials have been used to modify commercially available fabricated materials into articles with improved properties; however the success of this approach remains to be seen.

If a chromatographic support is equipped with molecules which bind specifically with a component of a complex mixture, that component will be separated from the mixture and may be released subsequently by changing the experimental conditions (e.g., buffers, stringency, etc.) This type of separation is appropriately called "affinity chromatography" and remains an extremely effective and widely used separation technique (see Perry, E. S. in *Techniques of Chemistry*, Vol. 12 (J. Wiley) & May, S. W. in *Separations and Purification* 1978, 3rd ed.). It is certainly much more selective than traditional chromatographic techniques, e.g chromatography on silica, alumina, silica or alumina coated with long-chain hydrocarbons, polysaccharide and other types of beads or gels which in order to attain their maximum separating efficiency need to be used under conditions that are damaging to biomolecules, e.g., conditions involving high pressure, use of organic solvents and other denaturing agents, etc. (for example see Stewart, D. J., et al. *J. Biotechnology* 1989, 11, 253–266; Brown, E., et al. *Int. Symp. Affinity. Chromatography* & *Molecular Interactions* 1979, 86, 37–50).

The development of more powerful separation technologies depends significantly on breakthroughs in the field of materials science, specifically in the design and construct-on of materials that have the power to recognize specific molecular shapes under experimental conditions resembling those found in physiological media, i.e. , these experimental conditions must involve an aqueous medium whose temperature and pH are close to the physiological levels and which contains none of the agents known to damage or denature biomolecules. The construction of these "intelligent" materials frequently involves the introduction of small molecules capable of specifically recognizing others into existing materials, e.g. surfaces, films, gels, beads, etc., by a wide variety of chemical modifications; alternatively molecules capable of recognition are converted to monomers and used to create the "intelligent" materials through polymerization reactions.

Advances in the ability to synthesize large numbers of peptides have made it possible to create a vast array of combinations of microenvironments within which different proteins may interact in equally. Kauvar (U.S. Pat, No.

5,340,474) has developed a chromatographic method to obtain ligands which have the required affinity specific for a selected member of an array of analytes by providing maximal diversity in the choice of these ligands. A key to this technology is the use of a flow-through 96-well plate compatible for assaying large numbers of parallel samples. Their short peptide-based ligands as paratope analogs (or "paralogs") contain an N-terminal amino acid spacer used for coupling to the sorbent. The C-terminal is capped with an amide group. Diversity is then created with the use of hydrophobic amino acids, enantiomeric amino acids, positively charged, negatively charged, and neutral (hydrophilic) residues, as well as intra-chain cyclization via the formation of disulfide bonds between cysteine residues. Protein is then loaded onto each column in the sorbent plate, and the proteins that are bound to the chromatographic sorbents are eluted, then collected into a second pretreated microplate (Benedek, K. et al. *J. Chromatography* 1992, 627, 51–61). Sets of paralogs are constructed by systematically varying five independent parameters drawn from protein structure literature: 1. a hydrophobic index; 2. an isoelectric point derived from overall charge by averaging the pKa values of the ionizable side chains in solution at pH 7; 3. a hydrophobic moment; 4. an analogous lateral dipole moment; 5. a corrugation factor, defined as the measure of the scattering in the distribution of bulky side chains along the helical backbone (see Villar, H. O. & Kauvar, L. M. *FEBS Letters* 1994, 349, 125–130) and to defined reproducible patterns of cross-reaction which represent distinctive spectra of the primary antigen and its analogs using an immunoassay of molecular analogs against panels of antibodies (Cheung, P. Y. K., et al. *Analytica Chimica Acta* 1993, 283, 181–192).

DEFINITIONS

This invention discloses a system for the design, synthesis and use of logically arranged collections of synthetic product molecules called "molecular constructs" from structural elements in such a manner that the collection of molecular constructs possesses a constant structural element and a variable structural element. The definitions are shown below.

A "construct" is a molecule which is a member of a collection of molecules containing a common constant structural element and a common variable structural element.

An "array" is a logical positional ordering of molecular constructs in Cartesian coordinates.

A "bond" or "chemical bond" is used to describe a group of electrons that is shared between two atoms. This term also denotes an ionic, covalent or other attractive force between two atoms.

A "building block" is any molecule useful in the assembly of a molecular construct.

The terms "fragment" or "structural diversity element" refer to the common variable structural element of a molecular construct.

The "molecular core" is the common constant structural element of a molecular construct.

A "spatial address" is a position in the array defined by unique Cartesian coordinates.

A "sub-array" is a set of spatial addresses within a given array containing those molecular constructs having a common molecular core and differ from each other by 0 (zero) or 1 (one) change in a fragment.

A "relative address" refers to a location within the array or sub array comparable to any selected address, and differing by 0 (zero) or only 1 (one) change in the common variable structural element.

An "operator" is a simultaneous and/or concurrent change in the condition of at least two spatial addresses in individual cells residing in an array or a sub-array that results in a structural change in at least one molecular construct in the array. In particular, an operator in terms of this invention can be the reaction of at least one site on the molecular core capable of becoming or providing attachment for a structural diversity element, to add or change a structural motif thereon. Other operators which can be performed according to the patent include but are not limited to: addition of reagents or solvents; quality control protocols such as gas chromatography, high performance liquid chromatography, mass spectrometry, infrared spectroscopy, ultraviolet spectroscopy, nuclear magnetic resonance spectroscopy, fluorescence spectroscopy, melting point, mass balance, combustion analysis and thin layer chromatography; biological and enzymological assays such as ELISA, spectroscopic inhibition assays, disc assays and binding affinity assays; mechanical motions or manipulations; passage of time which includes resting & evaporation; heating and cooling; iteration of previous steps in a synthesis; dilution and dispensation of products in a form suitable for the design purpose.

SUMMARY OF THE INVENTION

This invention is directed to an m×n array of different chemical compounds wherein each of said compounds has at least one structural diversity elements chosen from the group consisting of:

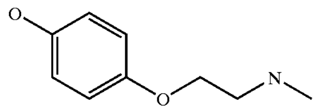
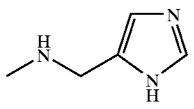
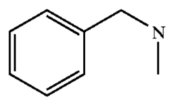
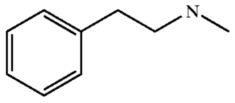
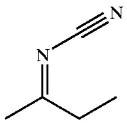
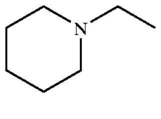
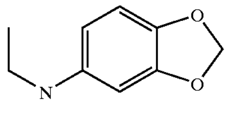
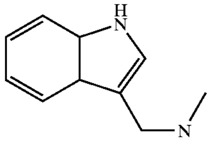
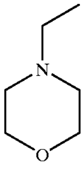
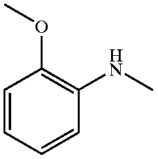
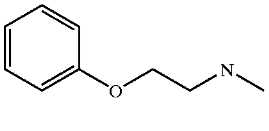
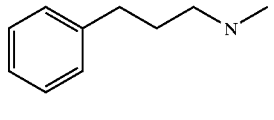

-continued

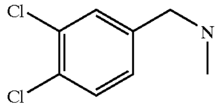
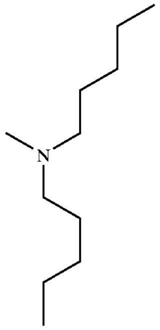
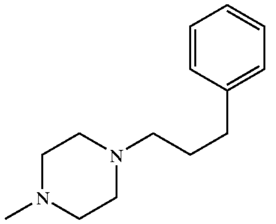
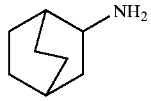
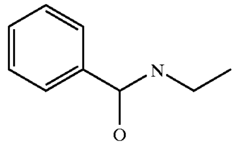
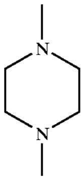
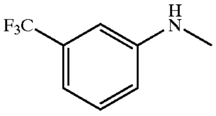
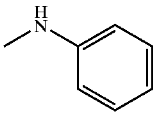
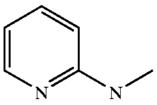
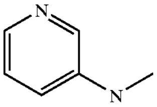
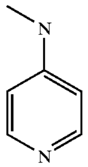
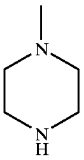
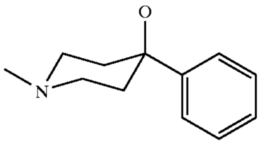
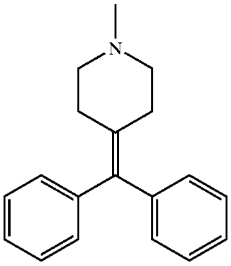
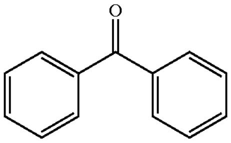
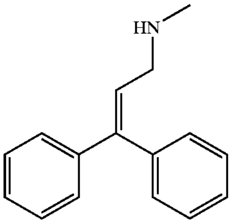

-continued

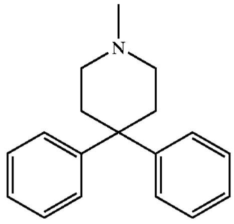
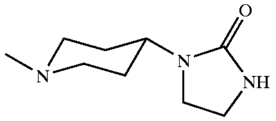

and wherein the scaffold structure is selected from the group consisting of:

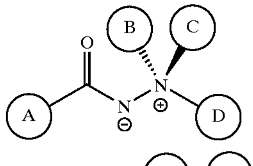
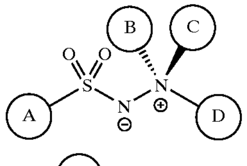
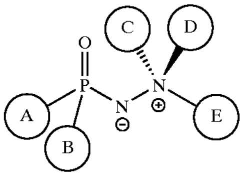
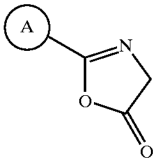

This invention is still further directed to an m×n array of different chemical compounds wherein each of said compounds has at least one of the structural diversity elements defined herein and wherein the scaffold structure may be a chemical molecule having at least three atoms of carbon, nitrogen, sulfur, phosphorus, or combinations thereof, and at least two sites on the molecule capable of undergoing a reaction to change the structure, usually by the addition of other molecules to a site capable of reacting to form or attach a structural diversity element.

This invention is still yet further directed to an n×m array of chemical compounds called molecular constructs possessing a logical ordering of molecular constructs comprising at least one k×l sub array within the array wherein each sub array is comprised of a) at least k.l molecular constructs having a common molecular core and differing from the other k.l molecular constructs in the sub array by at least one change in the structural diversity element attached to the molecular core; and b) each sub array within the array is related to all other sub arrays in that all corresponding molecular constructs within each sub array has at least one change in the structural diversity elements.

Also, the array of chemical compounds above encompasses those circumstances wherein n, m, k and l are all integers greater than 1.

The above array of chemical compounds can also be directed to those circumstances wherein n>5 and m>1, or n>10 and m>1, or even wherein n>5 and m>5. The specific integers used for m and n are not critical and any can be selected depending upon the desired form of the array.

The above defined array of chemical compounds is also directed to arrays wherein m multiplied by n is greater than 10, greater than 20, greater than 100, greater than 200, greater than 500, greater than 1000 or even greater than 5000. Again, the final number can be any multiple of the selected m and n values.

Still yet further the present invention is directed to an n×m array of chemical compounds called molecular constructs possessing a logical ordering of molecular constructs comprising at least one k×l sub array within the array the wherein each sub array is comprised of a) at least k.l molecular constructs having a common molecular core and differing from other k.l molecular constructs in the sub array by at least one change in the structural diversity element attached to the molecular core;

b) each sub array within the array is related to all other sub arrays in that all corresponding molecular constructs with each sub array has at least one change in the structural diversity elements; and c) and wherein each molecular construct is equidistant from at least two of its neighboring molecular constructs.

A preferred array is that defined immediately above wherein when n and m are greater than 3 and the chemical compounds are surrounded on four sides by four equidistant neighboring other chemical compounds.

Also the present invention covers n×m arrays of chemical compounds called molecular constructs possessing a logical ordering of molecular constructs comprising at least one k×l sub array within the array wherein each sub array is comprised of a) at least k.l molecular constructs having a common molecular core and differing from the other k.l molecular constructs in the sub array by at least one change in the structural diversity element attached to the molecular core;

b) each sub array within the array is related to all other sub arrays in that all corresponding molecular constructs within each sub array has at least one change in the structural diversity elements; and c) and wherein each molecular construct is separated from all other molecular constructs by a container material.

The contained materials for the above cited array may employ glass, polymers, silicon, or any other material known by those of ordinary skill in the art.

Further, the present invention is directed to an n×m×q array of chemical compounds called molecular constructs possessing a logical ordering of molecular constructs comprising at least one k×l sub array within the array wherein each sub array is comprised of a) at least k.l molecular constructs having a common molecular core and differing from the other k.l molecular constructs in the sub array by at least one change in the structural diversity element attached to the molecular core;

b) each sub array within the array is related to all other sub arrays in that all corresponding molecular constructs within each sub array has at least one change in the structural diversity elements; and c) and wherein q is an integer >1 and each array designated $q_1 \ldots q_s$ where s is an integer >than 1, differs from the other q arrays by at least one function.

In addition, the present invention is directed to an n×m×q array wherein the function is the addition of an organic structure selected from the group consisting of an amine, an aldehyde, an alcohol, a ketone, a carboxylic acids, an ether and an epoxy, and wherein the function may or may not be an analytic technique.

The reactions which are the subject of this invention may be performed simultaneously by using a mechanical apparatus such as multiple pipettes attached to an apparatus and other methods known to the skilled artisan.

DETAILED DESCRIPTION OF THE INVENTION

Figure 1:
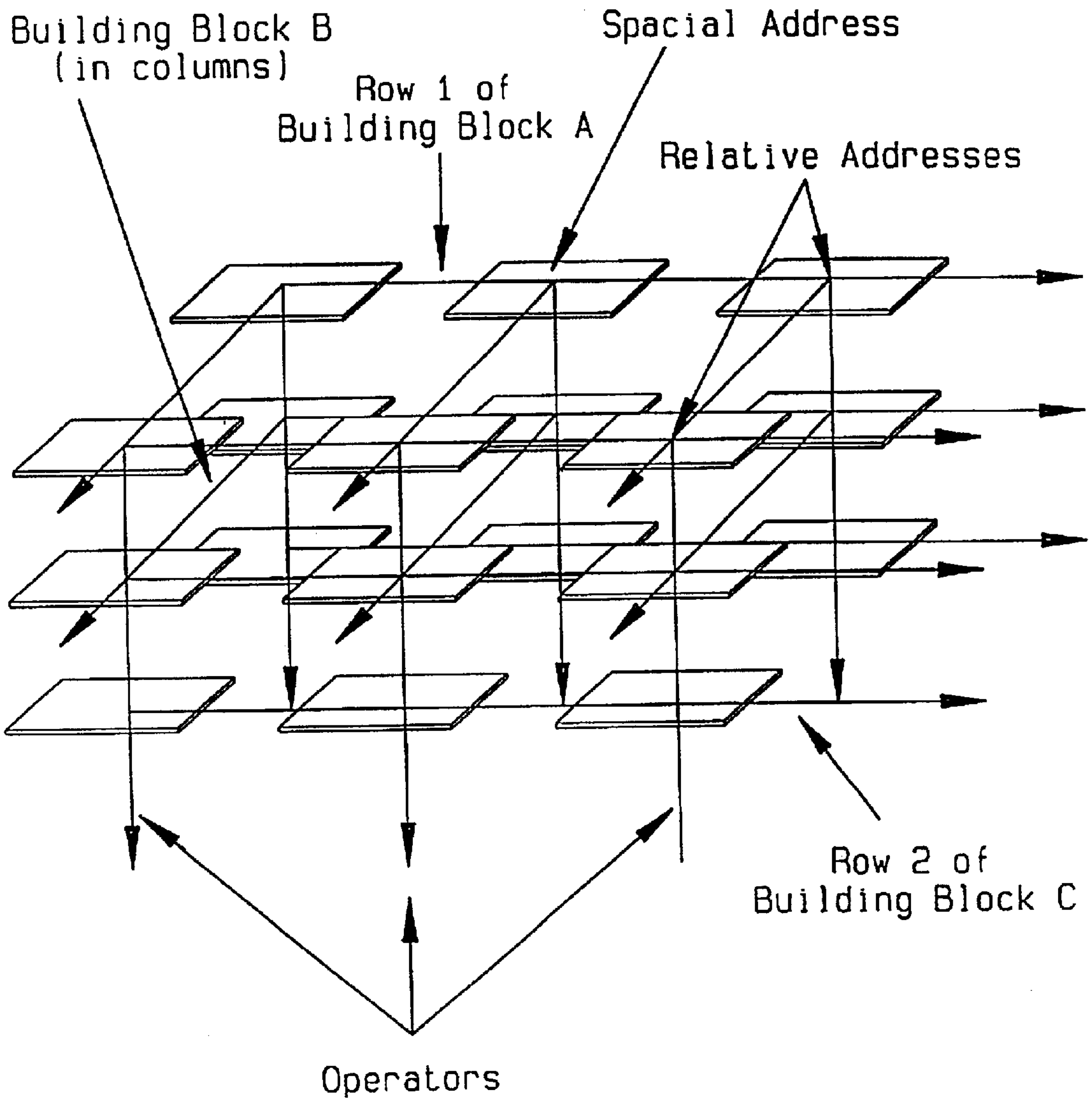
FIG. 1 is a graphic presentation of the steps followed for combining the building blocks to form the AN-1001 array.

This invention pertains to the logical layout, construction and testing of arrays of chemical compound for one of a variety of applications, in which the desired properties of the compound can be measured and correlated to specific ordered changes in the fragments use to construct them. The array is ordered in such a fashion as to expedite assembly, to maximize the informational content derived from the testing and to facilitate the rapid extraction of that data from the testing process. This method has great utility in accelerating the development of compounds have the optimal properties for the desired application.

The arrays are constructed from logically ordered and arranged sub-arrays of compounds. Each sub-array consists of spatially addressable sets of structurally related individual chemical compounds, ranging in number from one to $10^{12}$ and possessing the following properties: (1) a common structural scaffold element referred to as a "molecular core" and (2) a variable structural diversity element referred to as a fragment, in such a manner that the variation between any two compounds within a given sub-array consists only of either zero (0) or one (1) change in a fragment. These arrays may in turn be arranged in such a manner to form higher order arrays consisting of sets of arrays and tested to provide information regarding the optimum structural features available for the application.

The sub-arrays are arranged in such a manner that the direct comparisons of compounds automatically yields information regarding the effect known fragments have on a desired application, as well as on the effect on changes in physical and reactive properties. As provided by simple set theory for any number of independently variable structural diversity elements n, there exists n logical higher order array arrangements, such that relational information on the effect of variation of each of the n structural diversity elements can be obtained in a similar manner by comparison of testing data from the relative addresses in appropriately arranged sub-arrays.

An application of this invention is the rapid determination and optimization of desired biological or physical activity. An array is screened and the optimum candidate is chosen. This process can be continued in n dimensions to provide an absolute structure activity relationship ("SAR") picture of the candidate and selection in speeded by the rapid modular synthesis of arrays for use in testing. Thus in one light the invention is the most powerful tool to date for the rapid synthesis, screening and testing of compounds for investigational new drug ("IND") candidacy. This method is facilitated by virtue of selecting fragments based solely upon their ability to react and participate in the process of assembly.

These arrays may be assembled to form a "super array" for exhaustive testing. This approach provides a large scale view over different structures, functionalities and spatial arrangements for exploring biological activity.

The physical construction of the array also permits the logical and rapid analysis of synthetic results for the assurance of purity and quality. By testing a series of loci within any given sub-array, it becomes possible to determine the efficacy of construction of that core, and eliminate those fragments (i.e., process development within the assembly) which do not provide satisfactory results. This system, therefore possesses the ability to learn the utility of given reagents from previous results, and either delete them from further use or alter general conditions for their efficient incorporation into the array. Thus, both positive and negative results are of value in the ultimate construction of the array, and there is no ambiguity in regards to the inclusion or exclusion of fragments.

A further application of this invention is the facilitation of the optimal analyte or epitope binding ligand for attachment to a chromatographic support for separation or purification applications. A further application of this invention pertains to the ability to construct materials in a modular fashion, so as to facilitate their selection for such properties as strength, stability, reactivity or any other desired physical property. Whereas many methods rely upon logical choice for fragment candidates in such efforts, this method provides for the construction and testing of all candidates, thereby eliminating any compromises which traditional methods make based on the limits of time, manpower, and cost. By the screening of all possible synthetic variations the selection of the optimal candidate is a matter of data and not chemical intuition. The desired affinity can be rapidly optimized and directly correlated and attributed to the singular change made within a given sub-array. Therefore the selection of a ligand is no longer a random, intuitive process, but one of complete confidence providing exhaustive data (cf. Kauvar, L. M. U.S. Pat. No. 5,340,474).

Furthermore the invention provides for the development of seamless technology between planning, logistical development, execution of assembly in either an arrayed or subarrayed manner, quality analysis, packaging, distribution, testing, interpretation and iteration. The invention provides for the integrated design and delivery of a unified chemical discovery system, which by application of logic and implementation of information management, has been heretofore unknown. The invention provides for the occupation of all possible spatial addresses and therefore allows for complete analysis of desired properties. This concept can be extended toward the design and manufacture of appropriate hardware and software to support the integrated aspect of this modular construction.

The logically arranged arrays of the present invention are fundamentally different from all known prior art. Testing of these arrays automatically results in the generation of complete relational structural information such that a positive result provides: (1) information on a compound within any given spatial address; (2) simultaneous juxtaposition of this information upon a set of systematically structural congeners; (3) the ability to extract relational structural information from negative results in the presence of positive results.

All known prior art is universally directed toward the maximization of structural diversity. By definition this has excluded the acquisition of maximal data. In these cases, the relationship between individual structural variations and any resulting changes in a measurable property of the compounds can not be directly obtained from the testing results. The process of obtaining a compound having a desired physical property using methods of the prior art, while guided by intuition, is a random statistical process at best. Thus a positive result is not designed to give any additional information about the relationship between a specific structural modification and the corresponding change in the desired property, and a negative result can not provide any information at all. Methods in the prior art universally require extensive further experimentation to elucidate any relational information in a process which is costly, time consuming and one in which success is difficult to predict.

These arrays may be constructed from a wide variety of molecular cores, several examples of which are shown below. The criteria for core candidates are that the scaffold a) present attachment points for at least two structural diversity elements; b) is able to present these structural diversity elements in controlled, varying spatial arrangements; c) can be constructed in a rapid concerted fashion.

In general the molecular cores are linear, branched or cyclic organic compounds. In particular, the molecular cores comprise a chemical molecule having at least three carbon atoms and at least two sites on the molecule capable of undergoing a reaction to change the structure, usually by the addition of other molecules to a site capable of reacting to form or attach a structural diversity element.

One example of a molecular core is an aminimide molecule. This is a technology which has been previously described.

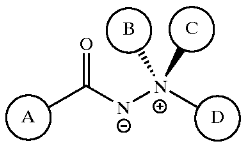

These compounds may be synthesized in a number of ways, from the reaction of an epoxide, an ester, and a hydrazine, as well as alkylation of a hydrazide, as shown below.

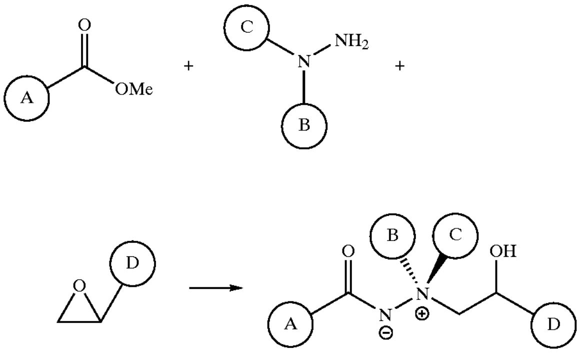

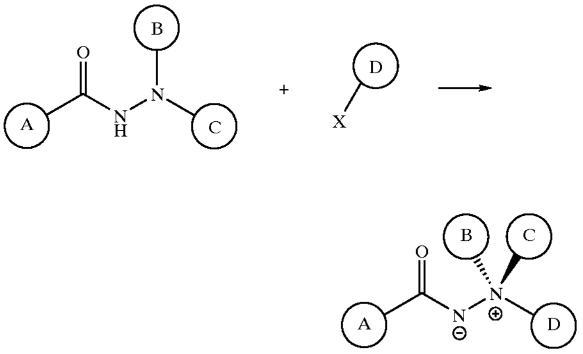

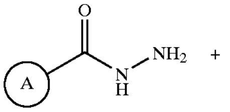

-continued

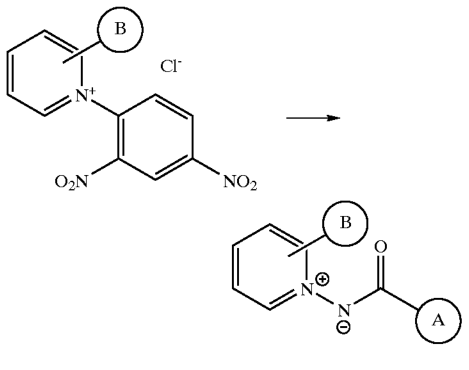

An example of a scaffold capable of forming a molecular core of an oxazolone molecule. Methylidene amides are formed from the sequential reaction of aldehydes, then amines with oxazolones. These compounds and their congeners may be in turn transformed into imidazolones:

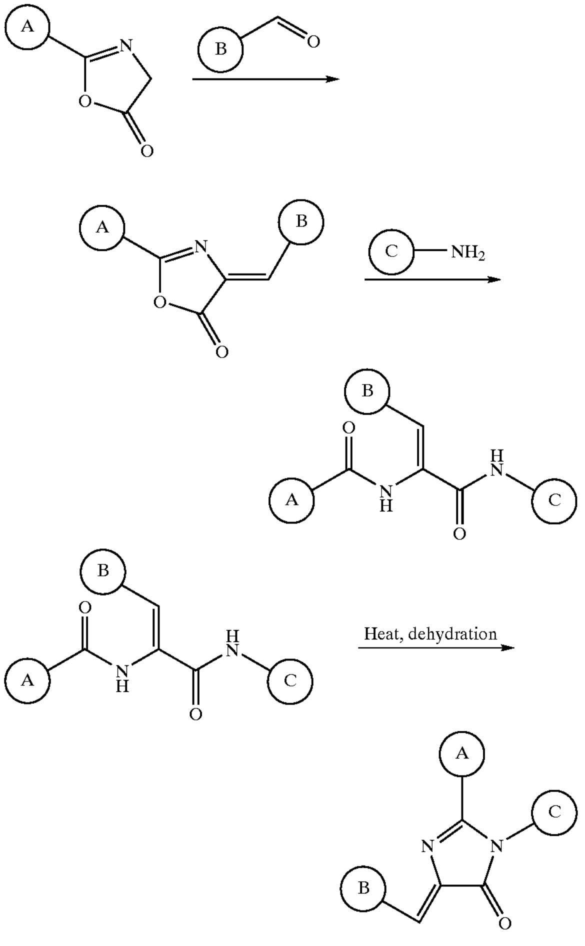

These compounds and their methods of manufacture are described in PCT Patent Appl. PCT/US93/12591.

Sulfonylaminimides and phosphonylaminimides are still further examples of molecular cores which can be constructed in an analogous manner as their carbon-based counterparts, with the exception of sulfonate esters not participating in the reaction of an epoxide and hydrazine in the desired manner.

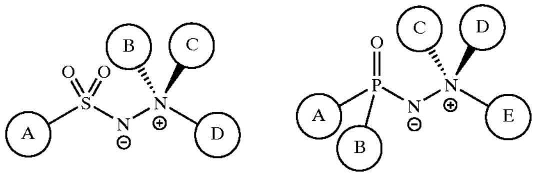

While the aminimide, oxazolone, sulphonylaminimide, and phosphonylaminimide are several examples of the concept of a molecular core, other molecular cores are possible according to the teachings of this invention. Further examples of possible molecular cores include, but are not limited to: alkaloids, quinolines, isoquinolines, benzimidazoles, benzothiazoles, purines, pyrimidines, thiazolidines, imidazopyrazinones, oxazolopyridines, pyrroles, pyrrolidines, imidazolidones, quinolones, amino acids, macrolides, penems, saccharides, xanthins, benzothiadiazine, anthracyclines, dibenzocycloheptadienes, inositols, porphyrins, corrins, and carboskeletons presenting geometric solids (e.g., dodecahedrane).

Diels-Alder reactions, Darzens glycidic ester condensations, Simmons-Smith cyclopropanations, rhodium catalyzed carbene additions, Ugi and Passerini reactions may all be done in such a manner, as to construct these arrays as described above. The application of this technology is facile and the format in which it is constructed is amenable to most organic transformations and reaction sequences.

The structural diversity elements may be the same or different, may be of a variety of structures and may differ markedly in their physical or functional properties, or may be the same; they may also be chiral or symmetric or from a compound which is chiral or symmetric. The structural diversity elements are preferably selected from:

1) amino acid derivatives of the form $(AA)_n$, which would include, for example, natural and synthetic amino acid residues (n=1) including all of the naturally occurring alpha amino acids, especially alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine; the naturally occurring disubstituted amino acids, such as amino isobutyric acid, and isovaline, etc.; a variety of synthetic amino acid residues, including alpha-disubstituted variants, species with olefinic substitution at the alpha position, species having derivatives, variants or mimetics of the naturally occurring side chains; N-substituted glycine residues; natural and synthetic species known to functionally mimic amino acid residues, such as statine, bestatin, etc. Peptides (n=2–30) constructed from the amino acids listed above, such as angiotensinogen and its family of physiologically important angiotensin hydrolysis products, as well as derivatives, variants and mimetics made from various combinations and permutations of all the natural and synthetic residues listed above. Polypeptides (n=31–70), such as big endothelin, pancreastatin, human growth hormone releasing factor and human pancreatic polypeptide. Proteins (n>70) including structural proteins such as collagen, functional proteins such as hemoglobin, regulatory proteins such as the dopamine and thrombin receptors.

2) a nucleotide derivative of the form $(NUCL)_n$, which includes natural and synthetic nucleotides (n=1), such as adenosine, thymine, guanidine, uridine, cytosine, derivatives of these and a variety of variants and mimetics of the purine ring, the sugar ring, the phosphate linkage and combinations of some or all of these. Nucleotide probes (n=2–25) and oligonucleotides (n>25) including all of the various possible; homo and hetero-synthetic combinations and permutations of the naturally occurring nucleotides; derivatives and variants containing synthetic purine or pyrimidine species, or mimics of these; various sugar ring mimetics; and a wide variety of alternate backbone analogs, including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogs.

3) a carbohydrate derivative of the form $(CH)_n$, which would include natural physiologically active carbohydrates; related compounds, such as glucose, galactose, sialic acids, β-D-glucosylamine and nojorimycin, which are both inhibitors of glucosidase; pseudo sugars, such as 5a-carba-2-D-galactopyranose, which is known to inhibit the growth of Klebsiella pneumonia (n=1); synthetic carbohydrate residues and derivatives of these (n=1) and all of the complex oligomeric permutations of these as found in nature, including high mannose oligosaccharides, the known antibiotic streptomycin (n>1).

4) a naturally occurring or synthetic organic structural motif. The term "motif" is defined as an organic molecule having or containing a specific structure that has biological activity, such as a molecule having a complementary structure to an enzyme active site, for example. This term includes any of the well known basic structures of pharmaceutical compounds including pharmacophores, or metabolites thereof. These basic structures include beta-lactams, such as penicillin, known to inhibit bacterial cell wall biosynthesis; dibenzazepines, known to bind to CNS receptors and used as antidepressants; polyketide macrolides, known to bind to bacterial ribosymes, etc. These structural motifs are generally known to have specific desirable binding properties to ligand acceptors.

5) a reporter element, such as a natural or synthetic dye or a residue capable of photographic amplification which possesses reactive groups that may be synthetically incorporated into the sulfaminimide structure or reaction scheme, and may be attached through the groups without adversely interfering or affecting with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) an organic moiety containing a polymerizable group such as a double bond, or other functionalities capable of undergoing condensation polymerization or copolymerization. Suitable groups include vinyl groups, oxirane groups, carboxylic acids, acid chlorides, esters, amides, azlactones, lactones and lactams. Other organic moiety such as those defined for R and R' may also be used.

7) a macromolecular component, such as a macromolecular surface or structures which may be attached to the sulfaminimide modules via the various reactive groups outlined above, in a manner where the binding of the attached species to a ligand-receptor molecule is not adversely affected and the interactive activity of the attached functionality is determined or limited by the macromolecule. Examples of macromolecular components include porous and non-porous inorganic components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrenedivinyl benzene beads, various methacrylate beads, PVA beads, and the like, commonly used for protein purification, water softening; and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range from about 1000 Daltons to as high as possible. They may take the form of nano-particles (dp=1000–5000 Angstroms), latex particles (dp=1000–5000 Angstroms), porous or non-porous beads (dp=0.5–1000 microns), membranes, gels, macroscopic surfaces or functionalized or coated versions or composites.

Structural diversity elements may also be a chemical bond to a suitable organic moiety, a hydrogen atom, an organic moiety which contains a suitable electrophilic group, such as an aldehyde, ester, alkyl halide, ketone, nitrile, epoxide or the like; a suitable nucleophilic group, such as a hydroxyl, amino, carboxylate, amide, carbanion, urea or the like; or one of the other structural diversity elements defined below. In addition, structural diversity elements may join to form a ring, bi-cyclic or tri-cyclic ring system; or structure which connects to the ends of the repeating unit of the compound defined by the preceding formula; or may be separately connected to other moieties.

Structural diversity elements on a scaffold may be the same or different and each may be one or more atoms of carbon, nitrogen, sulfur, oxygen, any other inorganic elements or combinations thereof. The structural diversity elements may be cyano, nitro, halogen, oxygen, hydroxy, alkoxy, thio, straight or branched chain alkyl, carbocyclic aryl and substituted or heterocyclic derivatives thereof. Structural diversity elements may be different in adjacent molecular cores and have a selected stereochemical arrangement about the carbon atom to which they are attached.

As used herein, the phrase linear chain or branched chained alkyl groups means any substituted or unsubstituted acyclic carbon-containing compounds, including alkanes, alkenes and alkynes. Alkyl groups having up to 30 carbon atoms are preferred. Examples of alkyl groups include lower alkyl, for example, methyl, ethyl, n-propyl, isopropyl, n-butyl, isobutyl or tert-butyl; upper alkyl, for example, octyl, nonyl, decyl, and the like; lower alkylene, for example, ethylene, propylene, propyldiene, butylene, butyldiene; upper alkenyl such as 1-decene, 1-nonene, 2,6-dimethyl-5-octenyl, 6-ethyl-5-octenyl or beptenyl, and the like; alkynyl such as 1-ethynyl, 2-butynyl, 1-pentynyl and the like. The ordinary skilled artisan is familiar with numerous linear and branched alkyl groups, which are within the scope of the present invention.

In addition, such alkyl group may also contain various substituents in which one or more hydrogen atoms has been replaced by a functional group. Functional groups include but are not limited to hydroxyl, amino, carboxyl, amide, ester, ether, and halogen (fluorine, chlorine, bromine and iodine), to mention but a few. Specific substituted alkyl groups can be, for example, alkoxy such as methoxy, ethoxy, butoxy, pentoxy and the like, polyhydroxy such as 1,2-dihydroxypropyl, 1,4-dihydroxy-1-butyl, and the like; methylamino, ethylamino, dimethylamino, diethylamino, triethylamino, cyclopentylamino, benzylamino, dibenzylamino, and the like; propionic, butanoic or pentanoic acid groups, and the like; formamido, acetamido, butanamido, and the like, methoxycarbonyl, ethoxycarbonyl or the like, chloroformyl, bromoformyl, 1,1-chloroethyl, bromoethyl, and the like, or dimethyl or diethyl ether groups or the like.

As used herein, substituted and unsubstituted carbocyclic groups of up to about 20 carbon atoms means cyclic carbon-containing compounds, including but not limited to cyclopentyl, cyclohexyl, cycloheptyl, adamantyl, and the like. Such cyclic groups may also contain various substituents in which one or more hydrogen atoms has been replaced by a functional group. Such functional groups include those described above, and lower alkyl groups as described above. The cyclic groups of the invention may further comprise a heteroatom. For example, in a specific embodiment, structural diversity element A is cyclohexanol.

As used herein, substituted and unsubstituted aryl groups means a hydrocarbon ring bearing a system of conjugated double bonds, usually comprising (4p−2) pi bond electrons, where p is an integer equal to or greater than 1. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g., pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocyclic groups, functional groups on the aryl groups can be nitro groups.

As mentioned above, structural diversity elements can also represent any combination of alkyl, carbocyclic or aryl groups; for example, 1-cyclohexylpropyl, benzylcyclohexylmethyl, 2-cyclohexyl-propyl, 2,2-methylcyclohexylpropyl, 2,2methylphenylpropyl, 2,2-methylphenylbutyl, and the like.

The structural diversity element may also be a connecting group that includes a terminal carbon atom for attachment to the quaternary nitrogen and may be different in adjacent n units.

In one embodiment of the invention, at least one of the structural diversity elements represents an organic or inorganic macromolecular surface. Examples of preferred macromolecular surfaces include ceramics such as silica and alumina, porous and non-porous beads, polymers such as a latex in the form of beads, membranes, gels, macroscopic surfaces or coated versions or composites or hybrids thereof.

All publications, patents, and patent applications are herein specifically incorporated by reference to their relevant portions (cf. The Merck Index, 11th Ed., Budavari, S. Ed., Merck & Co., Rahway, N.J., 1989; Physicians Desk Reference, 44th Ed., Barnhart, E. D. Publ., Medical Economics Company Inc., Oradell, N.J., 1990.

The following experimentals are meant to exemplify but one embodiment of the present invention and are not intended to limit the invention thereto.

EXAMPLES

A 10,240-component array is synthesized according to the teaching of the invention, from eight oxazolones (Building Block A), 32 aldehydes (Building Block B), and 40 amines (Building Block C). These compounds are illustrated in Tables 1–3.

AN 1001 Protocol: Tetrahydrofuran (THF) solutions of the building blocks are prepared according to the protocols generated on the spread sheets entitled "AN 1001 SOLUTION PROTOCOLS. CALCULATIONS, AND BUILDING BLOCK SELECTION". The Building Block solutions are 250 mM in "A", 250 mM in "B", and 500 mM in "C". Sufficient volumes of each solution are prepared to allow for the production of one row of reaction plates (Px, where x=1–128 for AN 1001). A reaction plate contains 80 spatial addresses each (8×10) and a row contains 16 reaction plates. The entire array consists of 8 rows of these reaction plates which are recycled 16 at a time to complete production of the array. The initial cycle's first operator is spatial delivery of 200 μl (1 eq., 50 μmoles) of the "A" building block solution according to the spread sheet entitled "AN 1001 SPATIAL LAYOUT, "A" BUILDING BLOCKS" starting at P1 and ending at P16. The second operator is spatial delivery of 200 μl (1 eq., 50 μmoles) of the "B" Building Blocks to the same reaction plates according to the spread sheet entitled "AN 1001 SPATIAL LAYOUT, "B" BUILDING BLOCKS." The third operator is addition to the same reaction plates of 50 μL of a I M (1 eq., 50 μmoles) solution of triethylamine in THF to all the spatial addresses that "A" and "B" building Blocks were added. The fourth operator is placement of the reaction blocks on an agitator at 60 degrees centigrade for 1.5 hrs. The fifth operator is spatial addition of 100 μl (1 eq., 50 μmoles) of the "C" building, block solutions according to the spread sheet entitled "AN 1001 SPATIAL LAYOUT, "C" BUILDING BLOCKS." The sixth operator is addition of 200 μL of THF to all the spatial addresses in the row or cycle. The seventh operator allows the reaction plates to stand at 25 degrees centigrade for 16 hrs. enabling evaporation of THF and completion of the synthesis of the molecular constructs. The following operators are then applied to distribute and reformat the molecular constructs for delivery and quality control. Heat the reaction plates to 60 degrees centigrade for 10 minutes and add 400 μl of dimethylsulfoxide (DMSO) to dissolve the molecular constructs (operator 8). Remove the solution from the reaction plates and place in a plastic microtiter plates in a spatial manner (operator 9). Spatially wash the reaction plates (each address) with 4 times 325 μL of DMSO and place in the same microtiter plates (operator 10). This affords 29.4 mM solutions of the molecular constructs in DMSO ready for further spacial distribution. Remove a 10 μL aliquot following a unique address pattern layout from each microtiter plate for quality control (operator 11). Spatially reformat these aliquots, dilute with 300 μL of acetonitrile and subject these samples to analysis by High Performance Liquid Chromatography and Mass Spectrometry for quality control of the molecular constructs in the each microtiter plate (operator 12). The above cycles and operators are repeated 7 more times to finish production and quality controlled validation of the array, AN 1001.

Figure 2:
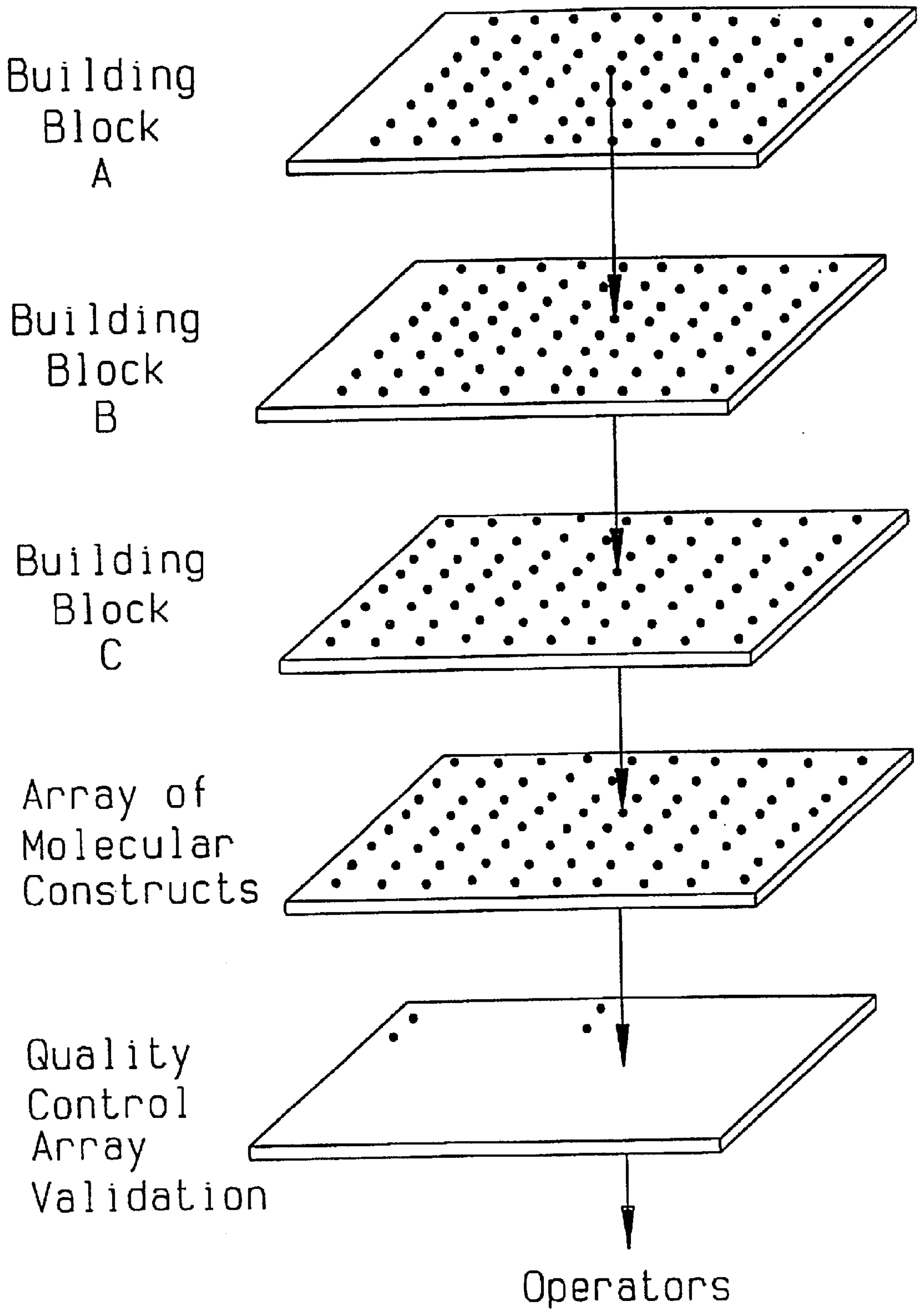
FIG. 2 is a scematic diagram of the process sequence used to form the compounds in the array.

FIG. 1 is a graphic representation of the array vertex to illustrate how the building blocks are combined to prepare the compounds in the array, while FIG. 2 is a schematic diagram of the process sequence used to form the compounds in the array and to validate their locations. An expanded view of a single reaction plate layout or template for the array is shown in Table 4.

AN 1001 SOLUTION PROTOCOLS, CALCULATIONS AND BUILDING BLOCK SELECTION

AT THEORY, ENTER

| | # | mM | uM/Well | Equiv. |
|---|---|---|---|---|
| "A" BUILDING BLOCKS | 8 | 250 | 50 | 1 |
| "B" BUILDING BLOCKS | 32 | 250 | 50 | 1 |
| "C" BUILDING BLOCKS | 40 | 500 | 50 | 1 |
| # ADDRESSES/REACTION PLATE | 80 | | | |

| | PER ADDRESS | | |
|---|---|---|---|
| CALCULATE, ACTUAL | Um | uL | mM |
| PER "A" | 50 | 200 | 250 |
| PER "B" | 50 | 200 | 250 |
| PER "C" | 50 | 100 | 500 |

| | # ADDRESSES | | | # REACTION PLATES | | |
|---|---|---|---|---|---|---|
| | TOTAL | ROW | COLUMN | TOTAL | ROW | COLUMN |
| PER "A" | 1280 | 1280 | 80 | 16 | 16 | 1 |
| PER "B" | 320 | 40 | 320 | 4 | 0.5 | 4 |
| PER "C" | 256 | 32 | 16 | 3.2 | 0.4 | 0.2 |
| ARRAY | 10240 | 1280 | 640 | 128 | 16 | 8 |

| | ml used | | | mMoles used | | |
|---|---|---|---|---|---|---|
| | TOTAL | ROW | COLUMN | TOTAL | ROW | COLUMN |
| PER "A" | 256 | 256 | 16 | 64 | 64 | 4 |
| PER "B" | 64 | 8 | 64 | 16 | 2 | 16 |
| PER "C" | 25.6 | 3.2 | 1.6 | 12.8 | 1.6 | 0.8 |

ENTER ACTUAL AMOUNTS DESIRED FROM ABOVE CALCULATIONS

| | VOL (ml) | mM | Excess % |
|---|---|---|---|
| PER "A" | 250 | 250 | 20 |
| PER "B" | 10 | 250 | 20 |
| PER "C" | 10 | 500 | 200 |

GENERATE SOLUTION PROTOCOLS

| "A" BUILDING BLOCKS | | | | | | | | VOLUME mL. | | |
|---|---|---|---|---|---|---|---|---|---|---|
| | | | | | | | | | Est. | Est. |
| Name | % | A# | Barcode | MW | d | uL | mg | Final | Liq. | Solid |
| 4-Phenyloxazolone | 95 | A1 | 00137-41 | 161 | | #DIV/01 | 12711 | 300 | #DIV/01 | 287 |
| m-Methoxzyoxazolone | 95 | A2 | 00703-41 | 191 | | #DIV/01 | 15079 | 300 | #DIV/01 | 285 |
| 2-Naphthaloxazolone | 95 | A3 | 00701-41 | 211 | | #DIV/01 | 16658 | 300 | #DIV/01 | 283 |
| Thiopheneoxazlone | 95 | A4 | 00704-41 | 167 | | #DIV/01 | 13184 | 300 | #DIV/01 | 287 |
| Trifluroro-p-tolualoxazolone | 95 | A5 | 00702-41 | 229 | | #DIV/01 | 18079 | 300 | #DIV/01 | 282 |
| 2,4-Dichloro-oxazolone | 95 | A6 | 00776-41 | 229 | | #DIV/01 | 18079 | 300 | #DIV/01 | 282 |
| p-Tolualoxazolone | 95 | A7 | 00700-41 | 175 | | #DIV/01 | 13816 | 300 | #DIV/01 | 286 |
| m-Tolualoxazolone | 95 | A8 | 00775-41 | 175 | | #DIV/01 | 13816 | 300 | #DIV/01 | 266 |

| "B" BUILDING BLOCKS | | | | | | | | VOLUME mL | | |
|---|---|---|---|---|---|---|---|---|---|---|
| | | | | | | | | | Est. | Est. |
| Name | % | B# | BARCODE | MW | d | uL | mg | Final | Liq. | Solid |
| 2,4-Difluorobenzaldehyde | 98 | B1 | 00116-41 | 142.11 | 1.299 | 334.9 | 435.03 | 12 | 11.665 | 12 |
| 2-Fluorobenzaldehyde | 97 | B2 | 00062-41 | 124.11 | 1.178 | 325.84 | 383.85 | 12 | 11.674 | 12 |
| 3-Fluorobenzaldehyde | 97 | B3 | 00007-41 | 124.11 | 1.17 | 328.07 | 383.85 | 12 | 11.672 | 12 |
| 4-Fluorobenzaldehyde | 98 | B4 | 00258-41 | 124.11 | 1.157 | 328.37 | 379.93 | 12 | 11.672 | 12 |
| aaa-Trifluoro-o-tolualdehyde | 98 | B5 | 00073-41 | 174.12 | 1.32 | 403.8 | 533.02 | 12 | 11.596 | 11 |
| aaa-Trifluoro-m-tolualdehyde | 97 | B6 | 00072-41 | 174.12 | 1.301 | 413.92 | 538.52 | 12 | 11.586 | 11 |

-continued

| GENERATE SOLUTION PROTOCOLS | | | | | | | | | | |
|---|---|---|---|---|---|---|---|---|---|---|
| aaa-Trifluoro-p-tolualdehyde | 98 | B7 | 00005-41 | 174.12 | 1.275 | 418.06 | 533.02 | 12 | 11.582 | 11 |
| o-Tolualdehyde | 97 | B8 | 00086-41 | 120.15 | 1.039 | 357.65 | 371.6 | 12 | 11.642 | 12 |
| m-Tolualdehyde | 97 | B9 | 00097-41 | 120.15 | 1.019 | 364.67 | 371.6 | 12 | 11.635 | 12 |
| p-Tolualdehyde | 97 | B10 | 00037-41 | 120.15 | 1.019 | 364.67 | 371.6 | 12 | 11.635 | 12 |
| 4-Ethylbenzaldehyde | 98 | B11 | 00108-41 | 134.18 | 0.979 | 419.57 | 410.76 | 12 | 11.58 | 12 |
| Benzaldehyde | 99 | B12 | 00260-41 | 106.12 | 1.044 | 308.82 | 321.58 | 12 | 11.692 | 12 |
| 2-Chlorobenzaldehyde | 99 | B13 | 00029-41 | 140.57 | 1.248 | 341.32 | 425.97 | 12 | 11.659 | 12 |
| 3-Chlorobenzaldehyde | 97 | B14 | 00069-41 | 140.57 | 1.241 | 350.32 | 434.75 | 12 | 11.65 | 12 |
| 2,4-Dichlorabenzaldehyde | 99 | B15 | 00646-41 | 175.01 | Solid | #VALUE | 530.33 | 12 | #VALUE | 11 |
| M-Anisaldehyde | 97 | B16 | 00094-41 | 136.15 | 1.119 | 376.3 | 421.08 | 12 | 11.624 | 12 |
| 4-(Methylithio)-benzaldehyde | 95 | B17 | 00173-41 | 152.22 | 1.144 | 420.19 | 480.69 | 12 | 11.68 | 12 |
| 4-Biphenylcarboxaldehyde | 95 | B18 | 00256-41 | 182.2 | Solid | #VALUE | 575.37 | 12 | #VALUE | 11 |
| 1-Naphthaldehyde | 98 | B19 | 00113-41 | 156.18 | 1.15 | 415.74 | 478.1 | 12 | 11.684 | 12 |
| 4-(Trifluoromethoxy)-benzaldehyde | 96 | B20 | 00171-41 | 190.12 | 1.331 | 446.37 | 594.13 | 12 | 11.654 | 11 |
| 3-Phenoxybenzaldehyde | 95 | B21 | 00125-42 | 198.22 | 1.147 | 545.73 | 625.96 | 12 | 11.454 | 11 |
| 2-Thiophenecarboxaldehyde | 98 | B22 | 00170-41 | 112.15 | 1.2 | 286.1 | 343.32 | 12 | 11.714 | 12 |
| 3-Thiophenecarboxaldehyde | 98 | B23 | 00643-41 | 112.15 | 1.28 | 268.22 | 343.32 | 12 | 11.732 | 12 |
| 3,5-Difluorobenzaldehyde | 98 | B24 | 00121-41 | 142.11 | | #DIV/01 | 435.03 | 12 | #DIV/01 | 12 |
| 3-Pyridinecarboxaldehyde | 99 | B25 | 00174-41 | 107.11 | 1.135 | 285.97 | 324.68 | 12 | 11.714 | 12 |
| 4-Pyridinecarboxaldehyde | 98 | B26 | 00172.41 | 107.11 | 1.122 | 292.24 | 327.89 | 12 | 11.708 | 12 |
| 4-Chlorobenzaldehyde | 97 | B27 | 00057-41 | 140.57 | solid | #VALUE | 434.75 | 12 | #VALUE | 12 |
| 3-Quinolinecarboxaldehyde | 98 | B28 | 00691-41 | 157.17 | solid | #VALUE | 481.13 | 12 | #VALUE | 12 |
| 4-Quinolinecarboxaldehyde | 97 | B29 | 00693-41 | 157.17 | solid | #VALUE | 486.09 | 12 | #VALUE | 12 |
| 2-Furaldehyde | 99 | B30 | 00650-41 | 96.09 | 1.16 | 251.02 | 291.18 | 12 | 11.749 | 12 |
| 3-Furaldehyde | 99 | B31 | 00641-41 | 98.09 | 1.111 | 262.09 | 291.18 | 12 | 11.738 | 12 |
| 5-Methylfurfural | 99 | B32 | 00692-41 | 110.11 | 1.107 | 301.42 | 333.67 | 12 | 11.699 | 12 |

| "C" BUILDING BLOCKS | | | | | | | | VOLUME mL. | | |
|---|---|---|---|---|---|---|---|---|---|---|
| | | | | | | | | | Est. | Est. |
| Name | % | C# | BARCODE | MW | d | uL | mg | Final | Liq. | Solid |
| Tetrahydrofurfurylamine | 97 | C1 | 00042-42 | 101.15 | 0.98 | 1596.1 | 1564.2 | 30 | 28.404 | 28 |
| Isobutylamine | 99 | C2 | 00664-41 | 73.14 | 0.736 | 1505.7 | 1108.2 | 30 | 28.494 | 29 |
| (+−)-sec-Butylamine | 99 | C3 | 00665-41 | 73.14 | 0.72 | 1539.1 | 1108.2 | 30 | 28.461 | 29 |
| Cyclobutylamine | 98 | C4 | 00182-41 | 71.12 | 0.833 | 1306.8 | 1088.6 | 30 | 28.693 | 29 |
| Cyclohexylamine | 99 | C5 | 00034-42 | 99.18 | 0.867 | 1733.2 | 1502.7 | 30 | 28.267 | 28 |
| 1-Ethylpropylamine | 98 | C6 | 00225-41 | 87.17 | 0.748 | 1783.7 | 1334.2 | 30 | 28.216 | 29 |
| Ethanol amine | 99 | C7 | 00071-42 | 61.08 | 1.012 | 914.48 | 925.45 | 30 | 29.086 | 29 |
| (S)-(+)-1-Amino-2-propanol | 99 | C8 | 00120-42 | 75.11 | 0.954 | 1192.9 | 1138 | 30 | 28.807 | 29 |
| 2-Amino-1-phenylethanol | 98 | C9 | 00176-42 | 137.18 | solid | #VALUE | 2099.7 | 30 | #VALUE | 28 |
| (1R, 2S)-(−)-Ephidrine | 99 | C10 | 00667-41 | 165.24 | 1.124 | 2227.4 | 2503.6 | 30 | 27.773 | 27 |
| (R)-(−)-Leucinol | 98 | C11 | 00177-41 | 117.19 | 0.917 | 1956.1 | 1793.7 | 30 | 28.044 | 28 |
| Piperidine | 99 | C12 | 00021-43 | 85.15 | 0.861 | 1498.4 | 1290.2 | 30 | 28.502 | 29 |
| 4-Benzylpiperidine | 99 | C13 | 00222-42 | 175.28 | 0.997 | 2663.7 | 2655.6 | 30 | 27.336 | 27 |
| Morpholine | 99 | C14 | 00031-41 | 87.12 | 0.999 | 1321.3 | 1320 | 30 | 28.679 | 29 |
| 1-Methyl-3-phenylpropyl-amine | 97 | C15 | 00084-41 | 149.24 | 0.922 | 2503.1 | 2307.8 | 30 | 27.497 | 28 |
| 3-Phenyl-1-propylamine | 98 | C16 | 00004-41 | 135.21 | 0.951 | 2176.2 | 2069.5 | 30 | 27.824 | 28 |
| Benzylamine | 99 | C17 | 00020-42 | 107.16 | 0.981 | 1655.1 | 1623.6 | 30 | 28.345 | 28 |
| Phenethylamine | 99 | C18 | 00008-41 | 121.18 | 0.965 | 1902.7 | 1836.1 | 30 | 28.097 | 28 |
| 1,2,3,4-Tetrahydro-1-naphthylamine | 98 | C19 | 00085-41 | 147.22 | 1.026 | 2198.3 | 2253.4 | 30 | 27.804 | 28 |
| 2-(p-Tolyl)ethylamine | 97 | C20 | 00118-42 | 135.21 | 0.93 | 2248.3 | 2090.9 | 30 | 27.752 | 28 |
| Aminodiphenylmethane | 96 | C21 | 00081-41 | 183.25 | 1.063 | 2693.6 | 2863.3 | 30 | 27.306 | 27 |
| 2,2-Diphenethylamine | 96 | C22 | 00024-41 | 197.28 | solid | #VALUE | 3082.5 | 30 | #VALUE | 27 |
| Tetrahydrofurfurylamine | 97 | C1 | 00042-42 | 101.15 | 0.98 | 1596.1 | 1564.2 | 30 | 28.404 | 28 |
| Isobutylamine | 99 | C2 | 00664-41 | 73.14 | 0.736 | 1505.7 | 1108.2 | 30 | 28.494 | 29 |
| (+−)-sec-Butylamine | 99 | C3 | 00665-41 | 73.14 | 0.72 | 1539.1 | 1108.2 | 30 | 28.461 | 29 |
| Cyclobutylamine | 98 | C4 | 00182-41 | 71.12 | 0.833 | 1306.8 | 1088.6 | 30 | 28.693 | 29 |
| Cyclohexylamine | 99 | C5 | 00034-42 | 99.18 | 0.867 | 1733.2 | 1502.7 | 30 | 28.267 | 28 |
| 1-Ethylpropylamine | 98 | C6 | 00225-41 | 87.17 | 0.748 | 1783.7 | 1334.2 | 30 | 28.216 | 29 |
| Ethanol amine | 99 | C7 | 00071-42 | 61.08 | 1.012 | 914.48 | 925.45 | 30 | 29.086 | 29 |
| (S)-(+)-1-Amino-2-propanol | 99 | C8 | 00120-42 | 75.11 | 0.954 | 1192.9 | 1138 | 30 | 28.807 | 29 |
| 2-Amino-1-phenylethanol | 98 | C9 | 00176-42 | 137.18 | solid | #VALUE | 2099.7 | 30 | #VALUE | 28 |
| (1R, 2S)-(−)-Ephidrine | 99 | C10 | 00667-41 | 165.24 | 1.124 | 2227.4 | 2503.6 | 30 | 27.773 | 27 |
| (R)-(−)-Leucinol | 98 | C11 | 00177-41 | 117.19 | 0.917 | 1956.1 | 1793.7 | 30 | 28.044 | 28 |
| Piperidine | 99 | C12 | 00021-43 | 85.15 | 0.861 | 1498.4 | 1290.2 | 30 | 28.502 | 29 |

-continued

| | | | | | | | | | | |
|---|---|---|---|---|---|---|---|---|---|---|
| 4-Benzylpiperidine | 99 | C13 | 00222-42 | 175.28 | 0.997 | 2663.7 | 2655.6 | 30 | 27.336 | 27 |
| Morpholine | 99 | C14 | 00031-41 | 87.12 | 0.999 | 1321.3 | 1320 | 30 | 28.679 | 29 |
| 1-Methyl-3-phenylpropyl-amine | 97 | C15 | 00084-41 | 149.24 | 0.922 | 2503.1 | 2307.8 | 30 | 27.497 | 28 |
| 3-Phenyl-1-propylamine | 98 | C16 | 00004-41 | 135.21 | 0.951 | 2176.2 | 2069.5 | 30 | 27.824 | 28 |
| Benzylamine | 99 | C17 | 00020-42 | 107.16 | 0.981 | 1655.1 | 1623.6 | 30 | 28.345 | 28 |
| Phenethylamine | 99 | C18 | 00008-41 | 121.18 | 0.965 | 1902.7 | 1836.1 | 30 | 28.097 | 28 |
| 1,2,3,4-Tetrahydro-1-naphthylamine | 98 | C19 | 00085-41 | 147.22 | 1.026 | 2198.3 | 2253.4 | 30 | 27.804 | 28 |
| 2-(p-Tolyl)ethylamine | 97 | C20 | 00118-42 | 135.21 | 0.93 | 2248.3 | 2090.9 | 30 | 27.752 | 28 |
| Aminodiphenylmethane | 96 | C21 | 00081-41 | 183.25 | 1.063 | 2693.6 | 2863.3 | 30 | 27.306 | 27 |
| 2,2-Diphenethylamine | 96 | C22 | 00024-41 | 197.28 | solid | #VALUE | 3082.5 | 30 | #VALUE | 27 |

TABLE 1

"A" BUILDING BLOCKS
ARRAY AN 1001

A1

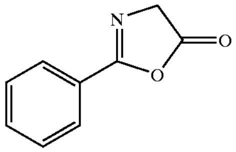

4-Phenyloxazolone

A2

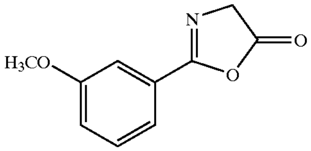

m-Methoxyoxazolone

A3

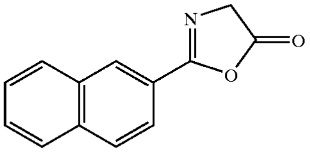

2-Napthaloxazolone

A4

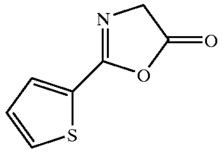

Thiopheneoxazolone

A5

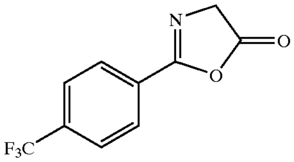

Trifluoro-p-tolualoxazolone

A6

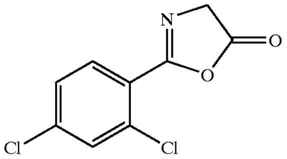

2,4-Dichloroxazolone

TABLE 1-continued

"A" BUILDING BLOCKS
ARRAY AN 1001

A7

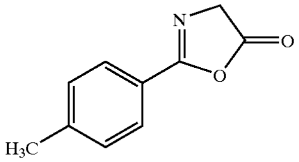

p-Tolualoxazolone

A8

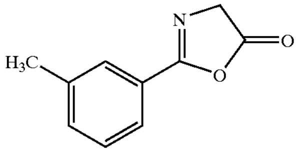

m-Tolualoxazolone

TABLE 2

"B" BUILDING BLOCKS
ARRAY AN 1001

B1

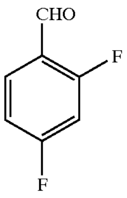

2,4-Difluorobenzaldehyde

B2

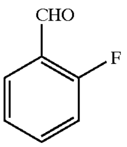

2-Fluorobenzaldehyde

TABLE 2-continued

| "B" BUILDING BLOCKS ARRAY AN 1001 | |
|---|---|
| 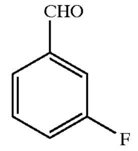 3-Fluorobenzaldehyde | B3 |
| 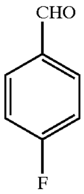 2-Fluorobenzaldehyde | B4 |
| 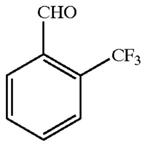 aaa-Trifluoro-o-tolualdehyde | B5 |
| 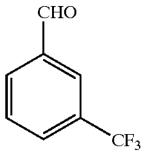 aaa-Trifluoro-m-tolualdehyde | B6 |
| 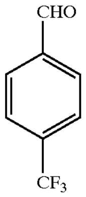 aaa-Trifluoro-p-tolualdehyde | B7 |
| 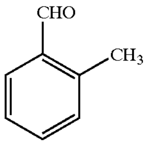 o-Tolualdehyde | B8 |
| 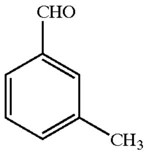 m-Tolualdehyde | B9 |

TABLE 2-continued

| "B" BUILDING BLOCKS ARRAY AN 1001 | |
|---|---|
| 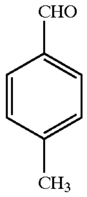 p-Tolualdehyde | B10 |
| 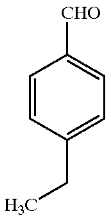 4-Ethylbenzaldehyde | B11 |
| 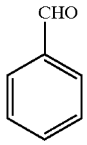 Benzaldehyde | B12 |
| 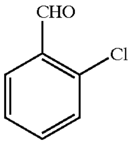 2-Chlorobenzaldehyde | B13 |
| 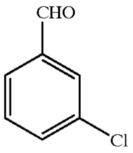 3-Chlorobenzaldehyde | B14 |
| 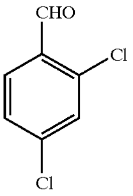 2,4-Dichlorobenzaldehyde | B15 |
| 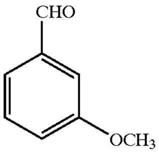 m-Anisaldehyde | B16 |

TABLE 2-continued

"B" BUILDING BLOCKS
ARRAY AN 1001

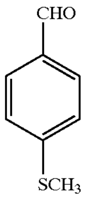
4-(Methylthio)-benzaldehyde
B17

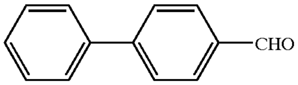
4-Biphenylcarboxaldehyde

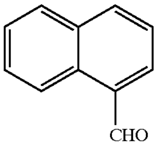
1-Napthaldehyde
B19

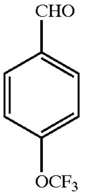
4-(Trifluoromethoxy)-benzaldehyde
B20

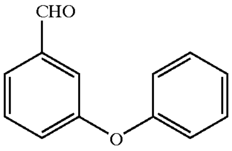
3-Phenoxybenzaldehyde
B21

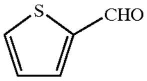
2-Thiophenecarboxaldehyde
B22

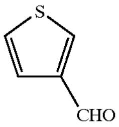
3-Thiophenecarboxaldehyde
B23

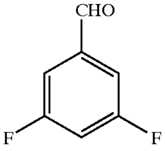
3,5-Difluorobenzaldehyde
B24

TABLE 2-continued

"B" BUILDING BLOCKS
ARRAY AN 1001

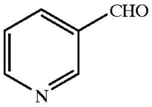
3-Pyridinecarboxaldehyde
B25

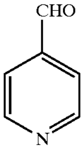
4-Pyridinecarboxaldehyde
B26

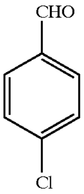
4-Chlorobenzaldehyde
B27

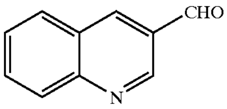
3-Quinolinecarboxaldehyde
B28

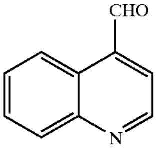
4-Quinolinecarboxaldehyde
B29

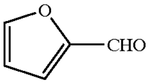
2-Furaldehyde
B30

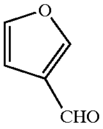
3-Furaldehyde
B31

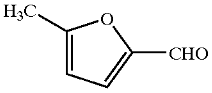
5-Methylfurfural
B32

TABLE 3

| "C" BUILDING BLOCKS ARRAY AN 1001 | |
|---|---|
| 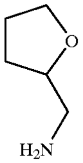 Tetrahydrofurfurylamine | C1 |
| 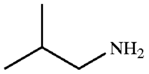 Isobutylamine | C2 |
| 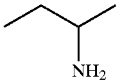 (+)-sec-Butylamine | C3 |
| 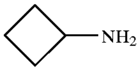 Cyclobutylamine | C4 |
| 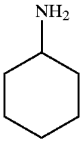 Cyclohexylamine | C5 |
| 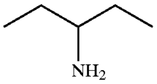 1-Ethylpropylamine | C6 |
| 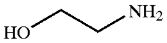 Ethanolamine | C7 |
| 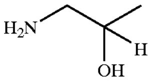 (S)-(+)-1-Amino-2-propanol | C8 |
| 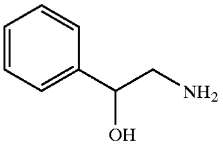 2-Amino-1-phenylethanol | C9 |
| 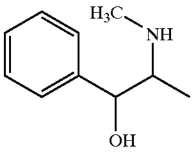 (1R,2S)-(-)-Ephidrine | C10 |

TABLE 3-continued

| "C" BUILDING BLOCKS ARRAY AN 1001 | |
|---|---|
| 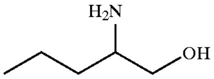 (rR)-(-)-Leucinol | C11 |
| 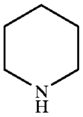 Piperidine | C12 |
| 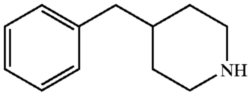 4-Benzylpiperidine | C13 |
| 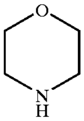 Morpholine | C14 |
| 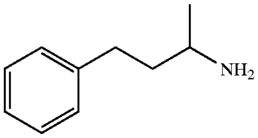 1-Methyl-3-phenylpropylamine | C15 |
| 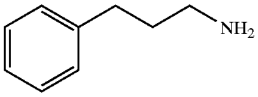 3-Phenyl-1-propylamine | C16 |
| 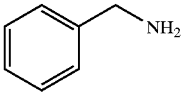 Benzylamine | C17 |
| 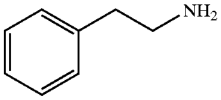 Phenethylamine | C18 |
| 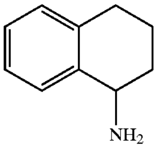 1,2,3,4-Tetrahydro-1-napthylamine | C19 |

TABLE 3-continued

"C" BUILDING BLOCKS
ARRAY AN 1001

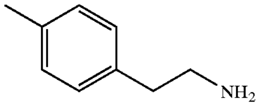
2-(p-Tolyl)ethylamine
C20

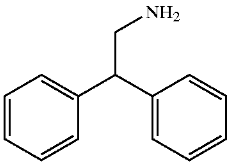
Aminodiphenylmethane
C21

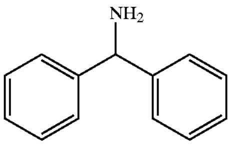
2,2-Diphenethylamine
C22

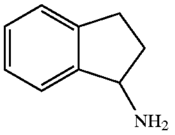
1-Aminodan
C23

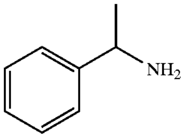
(+-)-a-Methylbenzylamine
C24

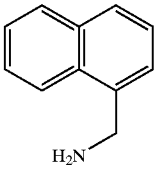
1-Napthalene-methylamine
C25

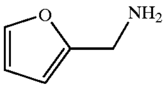
Furfurylamine
C26

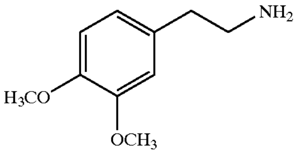
3,4-Dimethoxyphenethylamine
C27

TABLE 3-continued

"C" BUILDING BLOCKS
ARRAY AN 1001

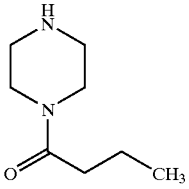
Ethyl 1-piperazine carboxylate
C28

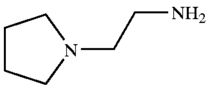
1-(2-Aminoethyl)pyrrolidine
C29

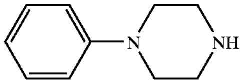
1-Phenylpiperazine
C30

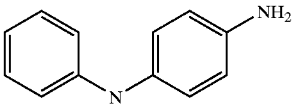
4-Amino-1-benzylpiperidine
C31

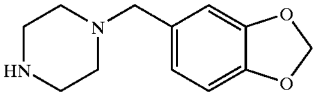
1-Piperionylpiperazine
C32

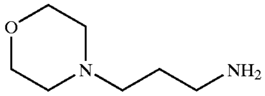
4-(3-Aminopropyl)-morpholine
C33

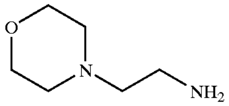
4-(2-Aminoethyl)-morpholine
C34

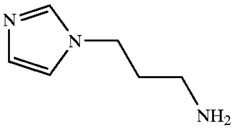
1-(3-Aminopropyl)imidazole
C35

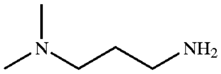
3-Dimethylaminopropylamine
C36

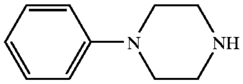
1-(a,a,a-Trifluoro-m-tolyl)-piperazine
C37

TABLE 3-continued

"C" BUILDING BLOCKS
ARRAY AN 1001

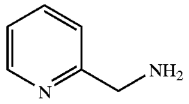

2-(Aminoethyl)pyridine

C38

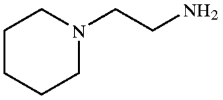

1-(2-Aminoethyl)piperidine

C39

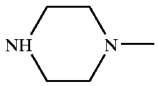

1-Methylpiperazine

C40

TABLE 4

EXPANDED VIEW OF A SINGLE REACTION PLATE
LAYOUT/TEMPLATE ARRAY, AN 1001

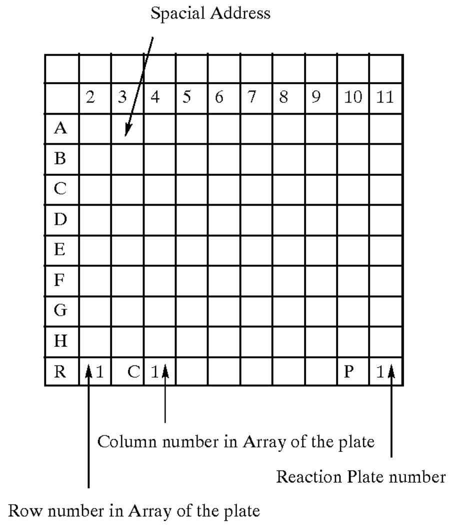

BB1

| | A | 1 | | | | | | | | | | A | 1 | | | | |
|---|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 | 7 |
| A | A1 | A1 | A1 | A1 | A1 | A1 | A1 | A1 | A1 | A1 | A | A1 | A1 | A1 | A1 | A1 | A1 |
| B | A1 | A1 | A1 | A1 | A1 | A1 | A1 | A1 | A1 | A1 | B | A1 | A1 | A1 | A1 | A1 | A1 |
| C | A1 | A1 | A1 | A1 | A1 | A1 | A1 | A1 | A1 | A1 | C | A1 | A1 | A1 | A1 | A1 | A1 |
| D | A1 | A1 | A1 | A1 | A1 | A1 | A1 | A1 | A1 | A1 | D | A1 | A1 | A1 | A1 | A1 | A1 |
| E | A1 | A1 | A1 | A1 | A1 | A1 | A1 | A1 | A1 | A1 | E | A1 | A1 | A1 | A1 | A1 | A1 |
| F | A1 | A1 | A1 | A1 | A1 | A1 | A1 | A1 | A1 | A1 | F | A1 | A1 | A1 | A1 | A1 | A1 |
| G | A1 | A1 | A1 | A1 | A1 | A1 | A1 | A1 | A1 | A1 | G | A1 | A1 | A1 | A1 | A1 | A1 |
| H | A1 | A1 | A1 | A1 | A1 | A1 | A1 | A1 | A1 | A1 | H | A1 | A1 | A1 | A1 | A1 | A1 |
| R | 1 | C | 1 | | | | | | P | 1 | R | 1 | C | 2 | | | |
| | A | 2 | | | | | | | | | | A | 2 | | | | |
| | 2 | 3 | 4 | 5 | 6 | 7 | 8 | 9 | 10 | 11 | | 2 | 3 | 4 | 5 | 6 | 7 |
| A | A2 | A2 | A2 | A2 | A2 | A2 | A2 | A2 | A2 | A2 | A | A2 | A2 | A2 | A2 | A2 | A2 |
| B | A2 | A2 | A2 | A2 | A2 | A2 | A2 | A2 | A2 | A2 | B | A2 | A2 | A2 | A2 | A2 | A2 |
| C | A2 | A2 | A2 | A2 | A2 | A2 | A2 | A2 | A2 | A2 | C | A2 | A2 | A2 | A2 | A2 | A2 |
| D | A2 | A2 | A2 | A2 | A2 | A2 | A2 | A2 | A2 | A2 | D | A2 | A2 | A2 | A2 | A2 | A2 |
| E | A2 | A2 | A2 | A2 | A2 | A2 | A2 | A2 | A2 | A2 | E | A2 | A2 | A2 | A2 | A2 | A2 |
| F | A2 | A2 | A2 | A2 | A2 | A2 | A2 | A2 | A2 | A2 | F | A2 | A2 | A2 | A2 | A2 | A2 |
| G | A2 | A2 | A2 | A2 | A2 | A2 | A2 | A2 | A2 | A2 | G | A2 | A2 | A2 | A2 | A2 | A2 |
| H | A2 | A2 | A2 | A2 | A2 | A2 | A2 | A2 | A2 | A2 | H | A2 | A2 | A2 | A2 | A2 | A2 |
| R | 2 | C | 1 | | | | | | P | 17 | R | 2 | C | 2 | | | |
| | A | 3 | | | | | | | | | | A | 3 | | | | |
| | 2 | 3 | 4 | 5 | 6 | 7 | 8 | 9 | 10 | 11 | | 2 | 3 | 4 | 5 | 6 | 7 |
| A | A3 | A3 | A3 | A3 | A3 | A3 | A3 | A3 | A3 | A3 | A | A3 | A3 | A3 | A3 | A3 | A3 |
| B | A3 | A3 | A3 | A3 | A3 | A3 | A3 | A3 | A3 | A3 | B | A3 | A3 | A3 | A3 | A3 | A3 |
| C | A3 | A3 | A3 | A3 | A3 | A3 | A3 | A3 | A3 | A3 | C | A3 | A3 | A3 | A3 | A3 | A3 |
| D | A3 | A3 | A3 | A3 | A3 | A3 | A3 | A3 | A3 | A3 | D | A3 | A3 | A3 | A3 | A3 | A3 |
| E | A3 | A3 | A3 | A3 | A3 | A3 | A3 | A3 | A3 | A3 | E | A3 | A3 | A3 | A3 | A3 | A3 |
| F | A3 | A3 | A3 | A3 | A3 | A3 | A3 | A3 | A3 | A3 | F | A3 | A3 | A3 | A3 | A3 | A3 |
| G | A3 | A3 | A3 | A3 | A3 | A3 | A3 | A3 | A3 | A3 | G | A3 | A3 | A3 | A3 | A3 | A3 |
| H | A3 | A3 | A3 | A3 | A3 | A3 | A3 | A3 | A3 | A3 | H | A3 | A3 | A3 | A3 | A3 | A3 |
| R | 3 | C | 1 | | | | | | P | 33 | R | 3 | C | 2 | | | |

-continued

| BB1 | | | | | | | | | | | | | | | | | |
|---|---|---|---|---|---|---|---|---|---|---|---|---|---|---|---|---|---|
| | A | 4 | | | | | | | | | | A | 4 | | | | |
| | 2 | 3 | 4 | 5 | 6 | 7 | 8 | 9 | 10 | 11 | | 2 | 3 | 4 | 5 | 6 | 7 |
| A | A4 | A4 | A4 | A4 | A4 | A4 | A4 | A4 | A4 | A4 | A | A4 | A4 | A4 | A4 | A4 | A4 |
| B | A4 | A4 | A4 | A4 | A4 | A4 | A4 | A4 | A4 | A4 | B | A4 | A4 | A4 | A4 | A4 | A4 |
| C | A4 | A4 | A4 | A4 | A4 | A4 | A4 | A4 | A4 | A4 | C | A4 | A4 | A4 | A4 | A4 | A4 |
| D | A4 | A4 | A4 | A4 | A4 | A4 | A4 | A4 | A4 | A4 | D | A4 | A4 | A4 | A4 | A4 | A4 |
| E | A4 | A4 | A4 | A4 | A4 | A4 | A4 | A4 | A4 | A4 | E | A4 | A4 | A4 | A4 | A4 | A4 |
| F | A4 | A4 | A4 | A4 | A4 | A4 | A4 | A4 | A4 | A4 | F | A4 | A4 | A4 | A4 | A4 | A4 |
| G | A4 | A4 | A4 | A4 | A4 | A4 | A4 | A4 | A4 | A4 | G | A4 | A4 | A4 | A4 | A4 | A4 |
| H | A4 | A4 | A4 | A4 | A4 | A4 | A4 | A4 | A4 | A4 | H | A4 | A4 | A4 | A4 | A4 | A4 |
| R | 4 | C | 1 | | | | | | P | 49 | R | 4 | C | 2 | | | |
| | A | 5 | | | | | | | | | | A | 5 | | | | |
| | 2 | 3 | 4 | 5 | 6 | 7 | 8 | 9 | 10 | 11 | | 2 | 3 | 4 | 5 | 6 | 7 |
| A | A5 | A5 | A5 | A5 | A5 | A5 | A5 | A5 | A5 | A5 | A | A5 | A5 | A5 | A5 | A5 | A5 |
| B | A5 | A5 | A5 | A5 | A5 | A5 | A5 | A5 | A5 | A5 | B | A5 | A5 | A5 | A5 | A5 | A5 |
| C | A5 | A5 | A5 | A5 | A5 | A5 | A5 | A5 | A5 | A5 | C | A5 | A5 | A5 | A5 | A5 | A5 |
| D | A5 | A5 | A5 | A5 | A5 | A5 | A5 | A5 | A5 | A5 | D | A5 | A5 | A5 | A5 | A5 | A5 |
| E | A5 | A5 | A5 | A5 | A5 | A5 | A5 | A5 | A5 | A5 | E | A5 | A5 | A5 | A5 | A5 | A5 |
| F | A5 | A5 | A5 | A5 | A5 | A5 | A5 | A5 | A5 | A5 | F | A5 | A5 | A5 | A5 | A5 | A5 |
| G | A5 | A5 | A5 | A5 | A5 | A5 | A5 | A5 | A5 | A5 | G | A5 | A5 | A5 | A5 | A5 | A5 |
| H | A5 | A5 | A5 | A5 | A5 | A5 | A5 | A5 | A5 | A5 | H | A5 | A5 | A5 | A5 | A5 | A5 |
| R | 5 | C | 1 | | | | | | P | 65 | R | 5 | C | 2 | | | |
| | A | 6 | | | | | | | | | | A | 6 | | | | |
| | 2 | 3 | 4 | 5 | 6 | 7 | 8 | 9 | 10 | 11 | | 2 | 3 | 4 | 5 | 6 | 7 |
| A | A6 | A6 | A6 | A6 | A6 | A6 | A6 | A6 | A6 | A6 | A | A6 | A6 | A6 | A6 | A6 | A6 |
| B | A6 | A6 | A6 | A6 | A6 | A6 | A6 | A6 | A6 | A6 | B | A6 | A6 | A6 | A6 | A6 | A6 |
| C | A6 | A6 | A6 | A6 | A6 | A6 | A6 | A6 | A6 | A6 | C | A6 | A6 | A6 | A6 | A6 | A6 |
| D | A6 | A6 | A6 | A6 | A6 | A6 | A6 | A6 | A6 | A6 | D | A6 | A6 | A6 | A6 | A6 | A6 |
| E | A6 | A6 | A6 | A6 | A6 | A6 | A6 | A6 | A6 | A6 | E | A6 | A6 | A6 | A6 | A6 | A6 |
| F | A6 | A6 | A6 | A6 | A6 | A6 | A6 | A6 | A6 | A6 | F | A6 | A6 | A6 | A6 | A6 | A6 |
| G | A6 | A6 | A6 | A6 | A6 | A6 | A6 | A6 | A6 | A6 | G | A6 | A6 | A6 | A6 | A6 | A6 |
| H | A6 | A6 | A6 | A6 | A6 | A6 | A6 | A6 | A6 | A6 | H | A6 | A6 | A6 | A6 | A6 | A6 |
| R | 6 | C | 1 | | | | | | P | 81 | R | 6 | C | 2 | | | |
| | A | 7 | | | | | | | | | | A | 7 | | | | |
| | 2 | 3 | 4 | 5 | 6 | 7 | 8 | 9 | 10 | 11 | | 2 | 3 | 4 | 5 | 6 | 7 |
| A | A7 | A7 | A7 | A7 | A7 | A7 | A7 | A7 | A7 | A7 | A | A7 | A7 | A7 | A7 | A7 | A7 |
| B | A7 | A7 | A7 | A7 | A7 | A7 | A7 | A7 | A7 | A7 | B | A7 | A7 | A7 | A7 | A7 | A7 |
| C | A7 | A7 | A7 | A7 | A7 | A7 | A7 | A7 | A7 | A7 | C | A7 | A7 | A7 | A7 | A7 | A7 |
| D | A7 | A7 | A7 | A7 | A7 | A7 | A7 | A7 | A7 | A7 | D | A7 | A7 | A7 | A7 | A7 | A7 |
| E | A7 | A7 | A7 | A7 | A7 | A7 | A7 | A7 | A7 | A7 | E | A7 | A7 | A7 | A7 | A7 | A7 |
| F | A7 | A7 | A7 | A7 | A7 | A7 | A7 | A7 | A7 | A7 | F | A7 | A7 | A7 | A7 | A7 | A7 |
| G | A7 | A7 | A7 | A7 | A7 | A7 | A7 | A7 | A7 | A7 | G | A7 | A7 | A7 | A7 | A7 | A7 |
| H | A7 | A7 | A7 | A7 | A7 | A7 | A7 | A7 | A7 | A7 | H | A7 | A7 | A7 | A7 | A7 | A7 |
| R | 7 | C | 1 | | | | | | P | 97 | R | 7 | C | 2 | | | |
| | A | 8 | | | | | | | | | | A | 8 | | | | |
| | 2 | 3 | 4 | 5 | 6 | 7 | 8 | 9 | 10 | 11 | | 2 | 3 | 4 | 5 | 6 | 7 |
| A | A8 | A8 | A8 | A8 | A8 | A8 | A8 | A8 | A8 | A8 | A | A8 | A8 | A8 | A8 | A8 | A8 |
| B | A8 | A8 | A8 | A8 | A8 | A8 | A8 | A8 | A8 | A8 | B | A8 | A8 | A8 | A8 | A8 | A8 |
| C | A8 | A8 | A8 | A8 | A8 | A8 | A8 | A8 | A8 | A8 | C | A8 | A8 | A8 | A8 | A8 | A8 |
| D | A8 | A8 | A8 | A8 | A8 | A8 | A8 | A8 | A8 | A8 | D | A8 | A8 | A8 | A8 | A8 | A8 |
| E | A8 | A8 | A8 | A8 | A8 | A8 | A8 | A8 | A8 | A8 | E | A8 | A8 | A8 | A8 | A8 | A8 |
| F | A8 | A8 | A8 | A8 | A8 | A8 | A8 | A8 | A8 | A8 | F | A8 | A8 | A8 | A8 | A8 | A8 |
| G | A8 | A8 | A8 | A8 | A8 | A8 | A8 | A8 | A8 | A8 | G | A8 | A8 | A8 | A8 | A8 | A8 |
| H | A8 | A8 | A8 | A8 | A8 | A8 | A8 | A8 | A8 | A8 | H | A8 | A8 | A8 | A8 | A8 | A8 |
| R | 8 | C | 1 | | | | | | P | 113 | R | 8 | C | 2 | | | |

-continued

BB1

| 8 | 9 | 10 | 11 | | A 2 | 1 3 | 4 | 5 | 6 | 7 | 8 | 9 | 10 | 11 | | A 2 |
|---|---|---|---|---|---|---|---|---|---|---|---|---|---|---|---|---|
| A1 | A1 | A1 | A1 | A | A1 | A1 | A1 | A1 | A1 | A1 | A1 | A1 | A1 | A1 | A | A1 |
| A1 | A1 | A1 | A1 | B | A1 | A1 | A1 | A1 | A1 | A1 | A1 | A1 | A1 | A1 | B | A1 |
| A1 | A1 | A1 | A1 | C | A1 | A1 | A1 | A1 | A1 | A1 | A1 | A1 | A1 | A1 | C | A1 |
| A1 | A1 | A1 | A1 | D | A1 | A1 | A1 | A1 | A1 | A1 | A1 | A1 | A1 | A1 | D | A1 |
| A1 | A1 | A1 | A1 | E | A1 | A1 | A1 | A1 | A1 | A1 | A1 | A1 | A1 | A1 | E | A1 |
| A1 | A1 | A1 | A1 | F | A1 | A1 | A1 | A1 | A1 | A1 | A1 | A1 | A1 | A1 | F | A1 |
| A1 | A1 | A1 | A1 | G | A1 | A1 | A1 | A1 | A1 | A1 | A1 | A1 | A1 | A1 | G | A1 |
| A1 | A1 | A1 | A1 | H | A1 | A1 | A1 | A1 | A1 | A1 | A1 | A1 | A1 | A1 | H | A1 |
| | | P | 2 | R | 1 | C | 3 | | | | | | P | 3 | R | 1 |
| 8 | 9 | 10 | 11 | | A 2 | 2 3 | 4 | 5 | 6 | 7 | 8 | 9 | 10 | 11 | | A 2 |
| A2 | A2 | A2 | A2 | A | A2 | A2 | A2 | A2 | A2 | A2 | A2 | A2 | A2 | A2 | A | A2 |
| A2 | A2 | A2 | A2 | B | A2 | A2 | A2 | A2 | A2 | A2 | A2 | A2 | A2 | A2 | B | A2 |
| A2 | A2 | A2 | A2 | C | A2 | A2 | A2 | A2 | A2 | A2 | A2 | A2 | A2 | A2 | C | A2 |
| A2 | A2 | A2 | A2 | D | A2 | A2 | A2 | A2 | A2 | A2 | A2 | A2 | A2 | A2 | D | A2 |
| A2 | A2 | A2 | A2 | E | A2 | A2 | A2 | A2 | A2 | A2 | A2 | A2 | A2 | A2 | E | A2 |
| A2 | A2 | A2 | A2 | F | A2 | A2 | A2 | A2 | A2 | A2 | A2 | A2 | A2 | A2 | F | A2 |
| A2 | A2 | A2 | A2 | G | A2 | A2 | A2 | A2 | A2 | A2 | A2 | A2 | A2 | A2 | G | A2 |
| A2 | A2 | A2 | A2 | H | A2 | A2 | A2 | A2 | A2 | A2 | A2 | A2 | A2 | A2 | H | A2 |
| | | P | 18 | R | 2 | C | 3 | | | | | | P | 19 | R | 2 |
| 8 | 9 | 10 | 11 | | A 2 | 3 3 | 4 | 5 | 6 | 7 | 8 | 9 | 10 | 11 | | A 2 |
| A3 | A3 | A3 | A3 | A | A3 | A3 | A3 | A3 | A3 | A3 | A3 | A3 | A3 | A3 | A | A3 |
| A3 | A3 | A3 | A3 | B | A3 | A3 | A3 | A3 | A3 | A3 | A3 | A3 | A3 | A3 | B | A3 |
| A3 | A3 | A3 | A3 | C | A3 | A3 | A3 | A3 | A3 | A3 | A3 | A3 | A3 | A3 | C | A3 |
| A3 | A3 | A3 | A3 | D | A3 | A3 | A3 | A3 | A3 | A3 | A3 | A3 | A3 | A3 | D | A3 |
| A3 | A3 | A3 | A3 | E | A3 | A3 | A3 | A3 | A3 | A3 | A3 | A3 | A3 | A3 | E | A3 |
| A3 | A3 | A3 | A3 | F | A3 | A3 | A3 | A3 | A3 | A3 | A3 | A3 | A3 | A3 | F | A3 |
| A3 | A3 | A3 | A3 | G | A3 | A3 | A3 | A3 | A3 | A3 | A3 | A3 | A3 | A3 | G | A3 |
| A3 | A3 | A3 | A3 | H | A3 | A3 | A3 | A3 | A3 | A3 | A3 | A3 | A3 | A3 | H | A3 |
| | | P | 34 | R | 3 | C | 3 | | | | | | P | 35 | R | 3 |
| 8 | 9 | 10 | 11 | | A 2 | 4 3 | 4 | 5 | 6 | 7 | 8 | 9 | 10 | 11 | | A 2 |
| A4 | A4 | A4 | A4 | A | A4 | A4 | A4 | A4 | A4 | A4 | A4 | A4 | A4 | A4 | A | A4 |
| A4 | A4 | A4 | A4 | B | A4 | A4 | A4 | A4 | A4 | A4 | A4 | A4 | A4 | A4 | B | A4 |
| A4 | A4 | A4 | A4 | C | A4 | A4 | A4 | A4 | A4 | A4 | A4 | A4 | A4 | A4 | C | A4 |
| A4 | A4 | A4 | A4 | D | A4 | A4 | A4 | A4 | A4 | A4 | A4 | A4 | A4 | A4 | D | A4 |
| A4 | A4 | A4 | A4 | E | A4 | A4 | A4 | A4 | A4 | A4 | A4 | A4 | A4 | A4 | E | A4 |
| A4 | A4 | A4 | A4 | F | A4 | A4 | A4 | A4 | A4 | A4 | A4 | A4 | A4 | A4 | F | A4 |
| A4 | A4 | A4 | A4 | G | A4 | A4 | A4 | A4 | A4 | A4 | A4 | A4 | A4 | A4 | G | A4 |
| A4 | A4 | A4 | A4 | H | A4 | A4 | A4 | A4 | A4 | A4 | A4 | A4 | A4 | A4 | H | A4 |
| | | P | 50 | R | 4 | C | 3 | | | | | | P | 51 | R | 4 |
| 8 | 9 | 10 | 11 | | A 2 | 5 3 | 4 | 5 | 6 | 7 | 8 | 9 | 10 | 11 | | A 2 |
| A5 | A5 | A5 | A5 | A | A5 | A5 | A5 | A5 | A5 | A5 | A5 | A5 | A5 | A5 | A | A5 |
| A5 | A5 | A5 | A5 | B | A5 | A5 | A5 | A5 | A5 | A5 | A5 | A5 | A5 | A5 | B | A5 |
| A5 | A5 | A5 | A5 | C | A5 | A5 | A5 | A5 | A5 | A5 | A5 | A5 | A5 | A5 | C | A5 |
| A5 | A5 | A5 | A5 | D | A5 | A5 | A5 | A5 | A5 | A5 | A5 | A5 | A5 | A5 | D | A5 |
| A5 | A5 | A5 | A5 | E | A5 | A5 | A5 | A5 | A5 | A5 | A5 | A5 | A5 | A5 | E | A5 |
| A5 | A5 | A5 | A5 | F | A5 | A5 | A5 | A5 | A5 | A5 | A5 | A5 | A5 | A5 | F | A5 |
| A5 | A5 | A5 | A5 | G | A5 | A5 | A5 | A5 | A5 | A5 | A5 | A5 | A5 | A5 | G | A5 |
| A5 | A5 | A5 | A5 | H | A5 | A5 | A5 | A5 | A5 | A5 | A5 | A5 | A5 | A5 | H | A5 |
| | | P | 66 | R | 5 | C | 3 | | | | | | P | 67 | R | 5 |

-continued

BB1

| | | | | | A | 6 | | | | | | | | | | A |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| A6 | A6 | A6 | A6 | A | A6 | A6 | A6 | A6 | A6 | A6 | A6 | A6 | A6 | A6 | A | A6 |
| A6 | A6 | A6 | A6 | B | A6 | A6 | A6 | A6 | A6 | A6 | A6 | A6 | A6 | A6 | B | A6 |
| A6 | A6 | A6 | A6 | C | A6 | A6 | A6 | A6 | A6 | A6 | A6 | A6 | A6 | A6 | C | A6 |
| A6 | A6 | A6 | A6 | D | A6 | A6 | A6 | A6 | A6 | A6 | A6 | A6 | A6 | A6 | D | A6 |
| A6 | A6 | A6 | A6 | E | A6 | A6 | A6 | A6 | A6 | A6 | A6 | A6 | A6 | A6 | E | A6 |
| A6 | A6 | A6 | A6 | F | A6 | A6 | A6 | A6 | A6 | A6 | A6 | A6 | A6 | A6 | F | A6 |
| A6 | A6 | A6 | A6 | G | A6 | A6 | A6 | A6 | A6 | A6 | A6 | A6 | A6 | A6 | G | A6 |
| A6 | A6 | A6 | A6 | H | A6 | A6 | A6 | A6 | A6 | A6 | A6 | A6 | A6 | A6 | H | A6 |
| | | P | 82 | R | 6 | C | 3 | | | | | | P | 83 | R | 6 |

| | | | | | A | 7 | | | | | | | | | | A |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| A7 | A7 | A7 | A7 | A | A7 | A7 | A7 | A7 | A7 | A7 | A7 | A7 | A7 | A7 | A | A7 |
| A7 | A7 | A7 | A7 | B | A7 | A7 | A7 | A7 | A7 | A7 | A7 | A7 | A7 | A7 | B | A7 |
| A7 | A7 | A7 | A7 | C | A7 | A7 | A7 | A7 | A7 | A7 | A7 | A7 | A7 | A7 | C | A7 |
| A7 | A7 | A7 | A7 | D | A7 | A7 | A7 | A7 | A7 | A7 | A7 | A7 | A7 | A7 | D | A7 |
| A7 | A7 | A7 | A7 | E | A7 | A7 | A7 | A7 | A7 | A7 | A7 | A7 | A7 | A7 | E | A7 |
| A7 | A7 | A7 | A7 | F | A7 | A7 | A7 | A7 | A7 | A7 | A7 | A7 | A7 | A7 | F | A7 |
| A7 | A7 | A7 | A7 | G | A7 | A7 | A7 | A7 | A7 | A7 | A7 | A7 | A7 | A7 | G | A7 |
| A7 | A7 | A7 | A7 | H | A7 | A7 | A7 | A7 | A7 | A7 | A7 | A7 | A7 | A7 | H | A7 |
| | | P | 98 | R | 7 | C | 3 | | | | | | P | 99 | R | 7 |

| | | | | | A | 8 | | | | | | | | | | A |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| A8 | A8 | A8 | A8 | A | A8 | A8 | A8 | A8 | A8 | A8 | A8 | A8 | A8 | A8 | A | A8 |
| A8 | A8 | A8 | A8 | B | A8 | A8 | A8 | A8 | A8 | A8 | A8 | A8 | A8 | A8 | B | A8 |
| A8 | A8 | A8 | A8 | C | A8 | A8 | A8 | A8 | A8 | A8 | A8 | A8 | A8 | A8 | C | A8 |
| A8 | A8 | A8 | A8 | D | A8 | A8 | A8 | A8 | A8 | A8 | A8 | A8 | A8 | A8 | D | A8 |
| A8 | A8 | A8 | A8 | E | A8 | A8 | A8 | A8 | A8 | A8 | A8 | A8 | A8 | A8 | E | A8 |
| A8 | A8 | A8 | A8 | F | A8 | A8 | A8 | A8 | A8 | A8 | A8 | A8 | A8 | A8 | F | A8 |
| A8 | A8 | A8 | A8 | G | A8 | A8 | A8 | A8 | A8 | A8 | A8 | A8 | A8 | A8 | G | A8 |
| A8 | A8 | A8 | A8 | H | A8 | A8 | A8 | A8 | A8 | A8 | A8 | A8 | A8 | A8 | H | A8 |
| | | P | 114 | R | 8 | C | 3 | | | | | | P | 115 | R | 8 |

| 1 | | | | | | | | | | A | 1 | | | | | | |
|---|---|---|---|---|---|---|---|---|---|---|---|---|---|---|---|---|---|
| 3 | 4 | 5 | 6 | 7 | 8 | 9 | 10 | 11 | | 2 | 3 | 4 | 5 | 6 | 7 | 8 | 9 |
| A1 | A1 | A1 | A1 | A1 | A1 | A1 | A1 | A1 | A | A1 | A1 | A1 | A1 | A1 | A1 | A1 | A1 |
| A1 | A1 | A1 | A1 | A1 | A1 | A1 | A1 | A1 | B | A1 | A1 | A1 | A1 | A1 | A1 | A1 | A1 |
| A1 | A1 | A1 | A1 | A1 | A1 | A1 | A1 | A1 | C | A1 | A1 | A1 | A1 | A1 | A1 | A1 | A1 |
| A1 | A1 | A1 | A1 | A1 | A1 | A1 | A1 | A1 | D | A1 | A1 | A1 | A1 | A1 | A1 | A1 | A1 |
| A1 | A1 | A1 | A1 | A1 | A1 | A1 | A1 | A1 | E | A1 | A1 | A1 | A1 | A1 | A1 | A1 | A1 |
| A1 | A1 | A1 | A1 | A1 | A1 | A1 | A1 | A1 | F | A1 | A1 | A1 | A1 | A1 | A1 | A1 | A1 |
| A1 | A1 | A1 | A1 | A1 | A1 | A1 | A1 | A1 | G | A1 | A1 | A1 | A1 | A1 | A1 | A1 | A1 |
| A1 | A1 | A1 | A1 | A1 | A1 | A1 | A1 | A1 | H | A1 | A1 | A1 | A1 | A1 | A1 | A1 | A1 |
| C | 4 | | | | | | P | 4 | R | 1 | C | 5 | | | | | |

| 2 | | | | | | | | | | A | 2 | | | | | | |
|---|---|---|---|---|---|---|---|---|---|---|---|---|---|---|---|---|---|
| 3 | 4 | 5 | 6 | 7 | 8 | 9 | 10 | 11 | | 2 | 3 | 4 | 5 | 6 | 7 | 8 | 9 |
| A2 | A2 | A2 | A2 | A2 | A2 | A2 | A2 | A2 | A | A2 | A2 | A2 | A2 | A2 | A2 | A2 | A2 |
| A2 | A2 | A2 | A2 | A2 | A2 | A2 | A2 | A2 | B | A2 | A2 | A2 | A2 | A2 | A2 | A2 | A2 |
| A2 | A2 | A2 | A2 | A2 | A2 | A2 | A2 | A2 | C | A2 | A2 | A2 | A2 | A2 | A2 | A2 | A2 |
| A2 | A2 | A2 | A2 | A2 | A2 | A2 | A2 | A2 | D | A2 | A2 | A2 | A2 | A2 | A2 | A2 | A2 |
| A2 | A2 | A2 | A2 | A2 | A2 | A2 | A2 | A2 | E | A2 | A2 | A2 | A2 | A2 | A2 | A2 | A2 |
| A2 | A2 | A2 | A2 | A2 | A2 | A2 | A2 | A2 | F | A2 | A2 | A2 | A2 | A2 | A2 | A2 | A2 |
| A2 | A2 | A2 | A2 | A2 | A2 | A2 | A2 | A2 | G | A2 | A2 | A2 | A2 | A2 | A2 | A2 | A2 |
| A2 | A2 | A2 | A2 | A2 | A2 | A2 | A2 | A2 | H | A2 | A2 | A2 | A2 | A2 | A2 | A2 | A2 |
| C | 4 | | | | | | P | 20 | R | 2 | C | 5 | | | | | |

-continued

| BB1 | | | | | | | | | | | | | | | | | |
|---|---|---|---|---|---|---|---|---|---|---|---|---|---|---|---|---|---|
| 3 | | | | | | | | | | A | 3 | | | | | | |
| 3 | 4 | 5 | 6 | 7 | 8 | 9 | 10 | 11 | | 2 | 3 | 4 | 5 | 6 | 7 | 8 | 9 |
| A3 | A3 | A3 | A3 | A3 | A3 | A3 | A3 | A3 | A | A3 | A3 | A3 | A3 | A3 | A3 | A3 | A3 |
| A3 | A3 | A3 | A3 | A3 | A3 | A3 | A3 | A3 | B | A3 | A3 | A3 | A3 | A3 | A3 | A3 | A3 |
| A3 | A3 | A3 | A3 | A3 | A3 | A3 | A3 | A3 | C | A3 | A3 | A3 | A3 | A3 | A3 | A3 | A3 |
| A3 | A3 | A3 | A3 | A3 | A3 | A3 | A3 | A3 | D | A3 | A3 | A3 | A3 | A3 | A3 | A3 | A3 |
| A3 | A3 | A3 | A3 | A3 | A3 | A3 | A3 | A3 | E | A3 | A3 | A3 | A3 | A3 | A3 | A3 | A3 |
| A3 | A3 | A3 | A3 | A3 | A3 | A3 | A3 | A3 | F | A3 | A3 | A3 | A3 | A3 | A3 | A3 | A3 |
| A3 | A3 | A3 | A3 | A3 | A3 | A3 | A3 | A3 | G | A3 | A3 | A3 | A3 | A3 | A3 | A3 | A3 |
| A3 | A3 | A3 | A3 | A3 | A3 | A3 | A3 | A3 | H | A3 | A3 | A3 | A3 | A3 | A3 | A3 | A3 |
| C | 4 | | | | | | P | 36 | R | 3 | C | 5 | | | | | |
| 4 | | | | | | | | | | A | 4 | | | | | | |
| 3 | 4 | 5 | 6 | 7 | 8 | 9 | 10 | 11 | | 2 | 3 | 4 | 5 | 6 | 7 | 8 | 9 |
| A4 | A4 | A4 | A4 | A4 | A4 | A4 | A4 | A4 | A | A4 | A4 | A4 | A4 | A4 | A4 | A4 | A4 |
| A4 | A4 | A4 | A4 | A4 | A4 | A4 | A4 | A4 | B | A4 | A4 | A4 | A4 | A4 | A4 | A4 | A4 |
| A4 | A4 | A4 | A4 | A4 | A4 | A4 | A4 | A4 | C | A4 | A4 | A4 | A4 | A4 | A4 | A4 | A4 |
| A4 | A4 | A4 | A4 | A4 | A4 | A4 | A4 | A4 | D | A4 | A4 | A4 | A4 | A4 | A4 | A4 | A4 |
| A4 | A4 | A4 | A4 | A4 | A4 | A4 | A4 | A4 | E | A4 | A4 | A4 | A4 | A4 | A4 | A4 | A4 |
| A4 | A4 | A4 | A4 | A4 | A4 | A4 | A4 | A4 | F | A4 | A4 | A4 | A4 | A4 | A4 | A4 | A4 |
| A4 | A4 | A4 | A4 | A4 | A4 | A4 | A4 | A4 | G | A4 | A4 | A4 | A4 | A4 | A4 | A4 | A4 |
| A4 | A4 | A4 | A4 | A4 | A4 | A4 | A4 | A4 | H | A4 | A4 | A4 | A4 | A4 | A4 | A4 | A4 |
| C | 4 | | | | | | P | 52 | R | 4 | C | 5 | | | | | |
| 5 | | | | | | | | | | A | 5 | | | | | | |
| 3 | 4 | 5 | 6 | 7 | 8 | 9 | 10 | 11 | | 2 | 3 | 4 | 5 | 6 | 7 | 8 | 9 |
| A5 | A5 | A5 | A5 | A5 | A5 | A5 | A5 | A5 | A | A5 | A5 | A5 | A5 | A5 | A5 | A5 | A5 |
| A5 | A5 | A5 | A5 | A5 | A5 | A5 | A5 | A5 | B | A5 | A5 | A5 | A5 | A5 | A5 | A5 | A5 |
| A5 | A5 | A5 | A5 | A5 | A5 | A5 | A5 | A5 | C | A5 | A5 | A5 | A5 | A5 | A5 | A5 | A5 |
| A5 | A5 | A5 | A5 | A5 | A5 | A5 | A5 | A5 | D | A5 | A5 | A5 | A5 | A5 | A5 | A5 | A5 |
| A5 | A5 | A5 | A5 | A5 | A5 | A5 | A5 | A5 | E | A5 | A5 | A5 | A5 | A5 | A5 | A5 | A5 |
| A5 | A5 | A5 | A5 | A5 | A5 | A5 | A5 | A5 | F | A5 | A5 | A5 | A5 | A5 | A5 | A5 | A5 |
| A5 | A5 | A5 | A5 | A5 | A5 | A5 | A5 | A5 | G | A5 | A5 | A5 | A5 | A5 | A5 | A5 | A5 |
| A5 | A5 | A5 | A5 | A5 | A5 | A5 | A5 | A5 | H | A5 | A5 | A5 | A5 | A5 | A5 | A5 | A5 |
| C | 4 | | | | | | P | 68 | R | 5 | C | 5 | | | | | |
| 6 | | | | | | | | | | A | 6 | | | | | | |
| 3 | 4 | 5 | 6 | 7 | 8 | 9 | 10 | 11 | | 2 | 3 | 4 | 5 | 6 | 7 | 8 | 9 |
| A6 | A6 | A6 | A6 | A6 | A6 | A6 | A6 | A6 | A | A6 | A6 | A6 | A6 | A6 | A6 | A6 | A6 |
| A6 | A6 | A6 | A6 | A6 | A6 | A6 | A6 | A6 | B | A6 | A6 | A6 | A6 | A6 | A6 | A6 | A6 |
| A6 | A6 | A6 | A6 | A6 | A6 | A6 | A6 | A6 | C | A6 | A6 | A6 | A6 | A6 | A6 | A6 | A6 |
| A6 | A6 | A6 | A6 | A6 | A6 | A6 | A6 | A6 | D | A6 | A6 | A6 | A6 | A6 | A6 | A6 | A6 |
| A6 | A6 | A6 | A6 | A6 | A6 | A6 | A6 | A6 | E | A6 | A6 | A6 | A6 | A6 | A6 | A6 | A6 |
| A6 | A6 | A6 | A6 | A6 | A6 | A6 | A6 | A6 | F | A6 | A6 | A6 | A6 | A6 | A6 | A6 | A6 |
| A6 | A6 | A6 | A6 | A6 | A6 | A6 | A6 | A6 | G | A6 | A6 | A6 | A6 | A6 | A6 | A6 | A6 |
| A6 | A6 | A6 | A6 | A6 | A6 | A6 | A6 | A6 | H | A6 | A6 | A6 | A6 | A6 | A6 | A6 | A6 |
| C | 4 | | | | | | P | 84 | R | 6 | C | 5 | | | | | |
| 7 | | | | | | | | | | A | 7 | | | | | | |
| 3 | 4 | 5 | 6 | 7 | 8 | 9 | 10 | 11 | | 2 | 3 | 4 | 5 | 6 | 7 | 8 | 9 |
| A7 | A7 | A7 | A7 | A7 | A7 | A7 | A7 | A7 | A | A7 | A7 | A7 | A7 | A7 | A7 | A7 | A7 |
| A7 | A7 | A7 | A7 | A7 | A7 | A7 | A7 | A7 | B | A7 | A7 | A7 | A7 | A7 | A7 | A7 | A7 |
| A7 | A7 | A7 | A7 | A7 | A7 | A7 | A7 | A7 | C | A7 | A7 | A7 | A7 | A7 | A7 | A7 | A7 |
| A7 | A7 | A7 | A7 | A7 | A7 | A7 | A7 | A7 | D | A7 | A7 | A7 | A7 | A7 | A7 | A7 | A7 |
| A7 | A7 | A7 | A7 | A7 | A7 | A7 | A7 | A7 | E | A7 | A7 | A7 | A7 | A7 | A7 | A7 | A7 |
| A7 | A7 | A7 | A7 | A7 | A7 | A7 | A7 | A7 | F | A7 | A7 | A7 | A7 | A7 | A7 | A7 | A7 |
| A7 | A7 | A7 | A7 | A7 | A7 | A7 | A7 | A7 | G | A7 | A7 | A7 | A7 | A7 | A7 | A7 | A7 |
| A7 | A7 | A7 | A7 | A7 | A7 | A7 | A7 | A7 | H | A7 | A7 | A7 | A7 | A7 | A7 | A7 | A7 |
| C | 4 | | | | | | P | 100 | R | 7 | C | 5 | | | | | |

-continued

| BB1 | | | | | | | | | | | | | | | | | | |
|---|---|---|---|---|---|---|---|---|---|---|---|---|---|---|---|---|---|---|
| 8 | | | | | | | | | | | A | 8 | | | | | | |
| 3 | 4 | 5 | 6 | 7 | 8 | 9 | 10 | 11 | | | 2 | 3 | 4 | 5 | 6 | 7 | 8 | 9 |
| A8 | A8 | A8 | A8 | A8 | A8 | A8 | A8 | A8 | | A | A8 | A8 | A8 | A8 | A8 | A8 | A8 | A8 |
| A8 | A8 | A8 | A8 | A8 | A8 | A8 | A8 | A8 | | B | A8 | A8 | A8 | A8 | A8 | A8 | A8 | A8 |
| A8 | A8 | A8 | A8 | A8 | A8 | A8 | A8 | A8 | | C | A8 | A8 | A8 | A8 | A8 | A8 | A8 | A8 |
| A8 | A8 | A8 | A8 | A8 | A8 | A8 | A8 | A8 | | D | A8 | A8 | A8 | A8 | A8 | A8 | A8 | A8 |
| A8 | A8 | A8 | A8 | A8 | A8 | A8 | A8 | A8 | | E | A8 | A8 | A8 | A8 | A8 | A8 | A8 | A8 |
| A8 | A8 | A8 | A8 | A8 | A8 | A8 | A8 | A8 | | F | A8 | A8 | A8 | A8 | A8 | A8 | A8 | A8 |
| A8 | A8 | A8 | A8 | A8 | A8 | A8 | A8 | A8 | | G | A8 | A8 | A8 | A8 | A8 | A8 | A8 | A8 |
| A8 | A8 | A8 | A8 | A8 | A8 | A8 | A8 | A8 | | H | A8 | A8 | A8 | A8 | A8 | A8 | A8 | A8 |
| C | 4 | | | | | | P | 116 | | R | 8 | C | 5 | | | | | |
| | | | | A | 1 | | | | | | | | | | | A | 1 | |
| 10 | 11 | | | 2 | 3 | 4 | 5 | 6 | 7 | 8 | 9 | 10 | 11 | | | 2 | 3 | 4 |
| A1 | A1 | | A | A1 | A1 | A1 | A1 | A1 | A1 | A1 | A1 | A1 | A1 | | A | A1 | A1 | A1 |
| A1 | A1 | | B | A1 | A1 | A1 | A1 | A1 | A1 | A1 | A1 | A1 | A1 | | B | A1 | A1 | A1 |
| A1 | A1 | | C | A1 | A1 | A1 | A1 | A1 | A1 | A1 | A1 | A1 | A1 | | C | A1 | A1 | A1 |
| A1 | A1 | | D | A1 | A1 | A1 | A1 | A1 | A1 | A1 | A1 | A1 | A1 | | D | A1 | A1 | A1 |
| A1 | A1 | | E | A1 | A1 | A1 | A1 | A1 | A1 | A1 | A1 | A1 | A1 | | E | A1 | A1 | A1 |
| A1 | A1 | | F | A1 | A1 | A1 | A1 | A1 | A1 | A1 | A1 | A1 | A1 | | F | A1 | A1 | A1 |
| A1 | A1 | | G | A1 | A1 | A1 | A1 | A1 | A1 | A1 | A1 | A1 | A1 | | G | A1 | A1 | A1 |
| A1 | A1 | | H | A1 | A1 | A1 | A1 | A1 | A1 | A1 | A1 | A1 | A1 | | H | A1 | A1 | A1 |
| P | 5 | | R | 1 | C | 6 | | | | | | P | 6 | | R | 1 | C | 7 |
| | | | | A | 2 | | | | | | | | | | | A | 2 | |
| 10 | 11 | | | 2 | 3 | 4 | 5 | 6 | 7 | 8 | 9 | 10 | 11 | | | 2 | 3 | 4 |
| A2 | A2 | | A | A2 | A2 | A2 | A2 | A2 | A2 | A2 | A2 | A2 | A2 | | A | A2 | A2 | A2 |
| A2 | A2 | | B | A2 | A2 | A2 | A2 | A2 | A2 | A2 | A2 | A2 | A2 | | B | A2 | A2 | A2 |
| A2 | A2 | | C | A2 | A2 | A2 | A2 | A2 | A2 | A2 | A2 | A2 | A2 | | C | A2 | A2 | A2 |
| A2 | A2 | | D | A2 | A2 | A2 | A2 | A2 | A2 | A2 | A2 | A2 | A2 | | D | A2 | A2 | A2 |
| A2 | A2 | | E | A2 | A2 | A2 | A2 | A2 | A2 | A2 | A2 | A2 | A2 | | E | A2 | A2 | A2 |
| A2 | A2 | | F | A2 | A2 | A2 | A2 | A2 | A2 | A2 | A2 | A2 | A2 | | F | A2 | A2 | A2 |
| A2 | A2 | | G | A2 | A2 | A2 | A2 | A2 | A2 | A2 | A2 | A2 | A2 | | G | A2 | A2 | A2 |
| A2 | A2 | | H | A2 | A2 | A2 | A2 | A2 | A2 | A2 | A2 | A2 | A2 | | H | A2 | A2 | A2 |
| P | 21 | | R | 2 | C | 6 | | | | | | P | 22 | | R | 2 | C | 7 |
| | | | | A | 3 | | | | | | | | | | | A | 3 | |
| 10 | 11 | | | 2 | 3 | 4 | 5 | 6 | 7 | 8 | 9 | 10 | 11 | | | 2 | 3 | 4 |
| A3 | A3 | | A | A3 | A3 | A3 | A3 | A3 | A3 | A3 | A3 | A3 | A3 | | A | A3 | A3 | A3 |
| A3 | A3 | | B | A3 | A3 | A3 | A3 | A3 | A3 | A3 | A3 | A3 | A3 | | B | A3 | A3 | A3 |
| A3 | A3 | | C | A3 | A3 | A3 | A3 | A3 | A3 | A3 | A3 | A3 | A3 | | C | A3 | A3 | A3 |
| A3 | A3 | | D | A3 | A3 | A3 | A3 | A3 | A3 | A3 | A3 | A3 | A3 | | D | A3 | A3 | A3 |
| A3 | A3 | | E | A3 | A3 | A3 | A3 | A3 | A3 | A3 | A3 | A3 | A3 | | E | A3 | A3 | A3 |
| A3 | A3 | | F | A3 | A3 | A3 | A3 | A3 | A3 | A3 | A3 | A3 | A3 | | F | A3 | A3 | A3 |
| A3 | A3 | | G | A3 | A3 | A3 | A3 | A3 | A3 | A3 | A3 | A3 | A3 | | G | A3 | A3 | A3 |
| A3 | A3 | | H | A3 | A3 | A3 | A3 | A3 | A3 | A3 | A3 | A3 | A3 | | H | A3 | A3 | A3 |
| P | 37 | | R | 3 | C | 6 | | | | | | P | 38 | | R | 3 | C | 7 |
| | | | | A | 4 | | | | | | | | | | | A | 4 | |
| 10 | 11 | | | 2 | 3 | 4 | 5 | 6 | 7 | 8 | 9 | 10 | 11 | | | 2 | 3 | 4 |
| A4 | A4 | | A | A4 | A4 | A4 | A4 | A4 | A4 | A4 | A4 | A4 | A4 | | A | A4 | A4 | A4 |
| A4 | A4 | | B | A4 | A4 | A4 | A4 | A4 | A4 | A4 | A4 | A4 | A4 | | B | A4 | A4 | A4 |
| A4 | A4 | | C | A4 | A4 | A4 | A4 | A4 | A4 | A4 | A4 | A4 | A4 | | C | A4 | A4 | A4 |
| A4 | A4 | | D | A4 | A4 | A4 | A4 | A4 | A4 | A4 | A4 | A4 | A4 | | D | A4 | A4 | A4 |
| A4 | A4 | | E | A4 | A4 | A4 | A4 | A4 | A4 | A4 | A4 | A4 | A4 | | E | A4 | A4 | A4 |
| A4 | A4 | | F | A4 | A4 | A4 | A4 | A4 | A4 | A4 | A4 | A4 | A4 | | F | A4 | A4 | A4 |
| A4 | A4 | | G | A4 | A4 | A4 | A4 | A4 | A4 | A4 | A4 | A4 | A4 | | G | A4 | A4 | A4 |
| A4 | A4 | | H | A4 | A4 | A4 | A4 | A4 | A4 | A4 | A4 | A4 | A4 | | H | A4 | A4 | A4 |
| P | 53 | | R | 4 | C | 6 | | | | | | P | 54 | | R | 4 | C | 7 |

-continued

| | | | | | | | | | | | | | | | | | | |
|---|---|---|---|---|---|---|---|---|---|---|---|---|---|---|---|---|---|---|
| | | | | | | | | | BB1 | | | | | | | | | |
| | | | | A | 5 | | | | | | | | | | | A | 5 | |
| 10 | 11 | | | 2 | 3 | 4 | 5 | 6 | 7 | 8 | 9 | 10 | 11 | | | 2 | 3 | 4 |
| A5 | A5 | | A | A5 | A5 | A5 | A5 | A5 | A5 | A5 | A5 | A5 | A5 | | A | A5 | A5 | A5 |
| A5 | A5 | | B | A5 | A5 | A5 | A5 | A5 | A5 | A5 | A5 | A5 | A5 | | B | A5 | A5 | A5 |
| A5 | A5 | | C | A5 | A5 | A5 | A5 | A5 | A5 | A5 | A5 | A5 | A5 | | C | A5 | A5 | A5 |
| A5 | A5 | | D | A5 | A5 | A5 | A5 | A5 | A5 | A5 | A5 | A5 | A5 | | D | A5 | A5 | A5 |
| A5 | A5 | | E | A5 | A5 | A5 | A5 | A5 | A5 | A5 | A5 | A5 | A5 | | E | A5 | A5 | A5 |
| A5 | A5 | | F | A5 | A5 | A5 | A5 | A5 | A5 | A5 | A5 | A5 | A5 | | F | A5 | A5 | A5 |
| A5 | A5 | | G | A5 | A5 | A5 | A5 | A5 | A5 | A5 | A5 | A5 | A5 | | G | A5 | A5 | A5 |
| A5 | A5 | | H | A5 | A5 | A5 | A5 | A5 | A5 | A5 | A5 | A5 | A5 | | H | A5 | A5 | A5 |
| P | 69 | | R | 5 | C | 6 | | | | | | P | 70 | | R | 5 | C | 7 |
| | | | | A | 6 | | | | | | | | | | | A | 6 | |
| 10 | 11 | | | 2 | 3 | 4 | 5 | 6 | 7 | 8 | 9 | 10 | 11 | | | 2 | 3 | 4 |
| A6 | A6 | | A | A6 | A6 | A6 | A6 | A6 | A6 | A6 | A6 | A6 | A6 | | A | A6 | A6 | A6 |
| A6 | A6 | | B | A6 | A6 | A6 | A6 | A6 | A6 | A6 | A6 | A6 | A6 | | B | A6 | A6 | A6 |
| A6 | A6 | | C | A6 | A6 | A6 | A6 | A6 | A6 | A6 | A6 | A6 | A6 | | C | A6 | A6 | A6 |
| A6 | A6 | | D | A6 | A6 | A6 | A6 | A6 | A6 | A6 | A6 | A6 | A6 | | D | A6 | A6 | A6 |
| A6 | A6 | | E | A6 | A6 | A6 | A6 | A6 | A6 | A6 | A6 | A6 | A6 | | E | A6 | A6 | A6 |
| A6 | A6 | | F | A6 | A6 | A6 | A6 | A6 | A6 | A6 | A6 | A6 | A6 | | F | A6 | A6 | A6 |
| A6 | A6 | | G | A6 | A6 | A6 | A6 | A6 | A6 | A6 | A6 | A6 | A6 | | G | A6 | A6 | A6 |
| A6 | A6 | | H | A6 | A6 | A6 | A6 | A6 | A6 | A6 | A6 | A6 | A6 | | H | A6 | A6 | A6 |
| P | 85 | | R | 6 | C | 6 | | | | | | P | 86 | | R | 6 | C | 7 |
| | | | | A | 7 | | | | | | | | | | | A | 7 | |
| 10 | 11 | | | 2 | 3 | 4 | 5 | 6 | 7 | 8 | 9 | 10 | 11 | | | 2 | 3 | 4 |
| A7 | A7 | | A | A7 | A7 | A7 | A7 | A7 | A7 | A7 | A7 | A7 | A7 | | A | A7 | A7 | A7 |
| A7 | A7 | | B | A7 | A7 | A7 | A7 | A7 | A7 | A7 | A7 | A7 | A7 | | B | A7 | A7 | A7 |
| A7 | A7 | | C | A7 | A7 | A7 | A7 | A7 | A7 | A7 | A7 | A7 | A7 | | C | A7 | A7 | A7 |
| A7 | A7 | | D | A7 | A7 | A7 | A7 | A7 | A7 | A7 | A7 | A7 | A7 | | D | A7 | A7 | A7 |
| A7 | A7 | | E | A7 | A7 | A7 | A7 | A7 | A7 | A7 | A7 | A7 | A7 | | E | A7 | A7 | A7 |
| A7 | A7 | | F | A7 | A7 | A7 | A7 | A7 | A7 | A7 | A7 | A7 | A7 | | F | A7 | A7 | A7 |
| A7 | A7 | | G | A7 | A7 | A7 | A7 | A7 | A7 | A7 | A7 | A7 | A7 | | G | A7 | A7 | A7 |
| A7 | A7 | | H | A7 | A7 | A7 | A7 | A7 | A7 | A7 | A7 | A7 | A7 | | H | A7 | A7 | A7 |
| P | 101 | | R | 7 | C | 6 | | | | | | P | 102 | | R | 7 | C | 7 |
| | | | | A | 8 | | | | | | | | | | | A | 8 | |
| 10 | 11 | | | 2 | 3 | 4 | 5 | 6 | 7 | 8 | 9 | 10 | 11 | | | 2 | 3 | 4 |
| A8 | A8 | | A | A8 | A8 | A8 | A8 | A8 | A8 | A8 | A8 | A8 | A8 | | A | A8 | A8 | A8 |
| A8 | A8 | | B | A8 | A8 | A8 | A8 | A8 | A8 | A8 | A8 | A8 | A8 | | B | A8 | A8 | A8 |
| A8 | A8 | | C | A8 | A8 | A8 | A8 | A8 | A8 | A8 | A8 | A8 | A8 | | C | A8 | A8 | A8 |
| A8 | A8 | | D | A8 | A8 | A8 | A8 | A8 | A8 | A8 | A8 | A8 | A8 | | D | A8 | A8 | A8 |
| A8 | A8 | | E | A8 | A8 | A8 | A8 | A8 | A8 | A8 | A8 | A8 | A8 | | E | A8 | A8 | A8 |
| A8 | A8 | | F | A8 | A8 | A8 | A8 | A8 | A8 | A8 | A8 | A8 | A8 | | F | A8 | A8 | A8 |
| A8 | A8 | | G | A8 | A8 | A8 | A8 | A8 | A8 | A8 | A8 | A8 | A8 | | G | A8 | A8 | A8 |
| A8 | A8 | | H | A8 | A8 | A8 | A8 | A8 | A8 | A8 | A8 | A8 | A8 | | H | A8 | A8 | A8 |
| P | 117 | | R | 8 | C | 6 | | | | | | P | 118 | | R | 8 | C | 7 |
| | | | | | | | | | A | 1 | | | | | | | | |
| 5 | 6 | 7 | 8 | 9 | 10 | 11 | | | 2 | 3 | 4 | 5 | 6 | 7 | 8 | 9 | 10 | 11 |
| A1 | A1 | A1 | A1 | A1 | A1 | A1 | | A | A1 | A1 | A1 | A1 | A1 | A1 | A1 | A1 | A1 | A1 |
| A1 | A1 | A1 | A1 | A1 | A1 | A1 | | B | A1 | A1 | A1 | A1 | A1 | A1 | A1 | A1 | A1 | A1 |
| A1 | A1 | A1 | A1 | A1 | A1 | A1 | | C | A1 | A1 | A1 | A1 | A1 | A1 | A1 | A1 | A1 | A1 |
| A1 | A1 | A1 | A1 | A1 | A1 | A1 | | D | A1 | A1 | A1 | A1 | A1 | A1 | A1 | A1 | A1 | A1 |
| A1 | A1 | A1 | A1 | A1 | A1 | A1 | | E | A1 | A1 | A1 | A1 | A1 | A1 | A1 | A1 | A1 | A1 |
| A1 | A1 | A1 | A1 | A1 | A1 | A1 | | F | A1 | A1 | A1 | A1 | A1 | A1 | A1 | A1 | A1 | A1 |
| A1 | A1 | A1 | A1 | A1 | A1 | A1 | | G | A1 | A1 | A1 | A1 | A1 | A1 | A1 | A1 | A1 | A1 |
| A1 | A1 | A1 | A1 | A1 | A1 | A1 | | H | A1 | A1 | A1 | A1 | A1 | A1 | A1 | A1 | A1 | A1 |
| | | | | | P | 7 | | R | 1 | C | 8 | | | | | | P | 8 |

-continued

BB1

| | | | | | | | | A | 2 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A2 | A2 | A2 | A2 | A2 | A2 | A2 | A | A2 | A2 | A2 | A2 | A2 | A2 | A2 | A2 | A2 | A2 |
| A2 | A2 | A2 | A2 | A2 | A2 | A2 | B | A2 | A2 | A2 | A2 | A2 | A2 | A2 | A2 | A2 | A2 |
| A2 | A2 | A2 | A2 | A2 | A2 | A2 | C | A2 | A2 | A2 | A2 | A2 | A2 | A2 | A2 | A2 | A2 |
| A2 | A2 | A2 | A2 | A2 | A2 | A2 | D | A2 | A2 | A2 | A2 | A2 | A2 | A2 | A2 | A2 | A2 |
| A2 | A2 | A2 | A2 | A2 | A2 | A2 | E | A2 | A2 | A2 | A2 | A2 | A2 | A2 | A2 | A2 | A2 |
| A2 | A2 | A2 | A2 | A2 | A2 | A2 | F | A2 | A2 | A2 | A2 | A2 | A2 | A2 | A2 | A2 | A2 |
| A2 | A2 | A2 | A2 | A2 | A2 | A2 | G | A2 | A2 | A2 | A2 | A2 | A2 | A2 | A2 | A2 | A2 |
| A2 | A2 | A2 | A2 | A2 | A2 | A2 | H | A2 | A2 | A2 | A2 | A2 | A2 | A2 | A2 | A2 | A2 |
| | | | | | P | 23 | R | 2 | C | 8 | | | | | | P | 24 |

| | | | | | | | | A | 3 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A3 | A3 | A3 | A3 | A3 | A3 | A3 | A | A3 | A3 | A3 | A3 | A3 | A3 | A3 | A3 | A3 | A3 |
| A3 | A3 | A3 | A3 | A3 | A3 | A3 | B | A3 | A3 | A3 | A3 | A3 | A3 | A3 | A3 | A3 | A3 |
| A3 | A3 | A3 | A3 | A3 | A3 | A3 | C | A3 | A3 | A3 | A3 | A3 | A3 | A3 | A3 | A3 | A3 |
| A3 | A3 | A3 | A3 | A3 | A3 | A3 | D | A3 | A3 | A3 | A3 | A3 | A3 | A3 | A3 | A3 | A3 |
| A3 | A3 | A3 | A3 | A3 | A3 | A3 | E | A3 | A3 | A3 | A3 | A3 | A3 | A3 | A3 | A3 | A3 |
| A3 | A3 | A3 | A3 | A3 | A3 | A3 | F | A3 | A3 | A3 | A3 | A3 | A3 | A3 | A3 | A3 | A3 |
| A3 | A3 | A3 | A3 | A3 | A3 | A3 | G | A3 | A3 | A3 | A3 | A3 | A3 | A3 | A3 | A3 | A3 |
| A3 | A3 | A3 | A3 | A3 | A3 | A3 | H | A3 | A3 | A3 | A3 | A3 | A3 | A3 | A3 | A3 | A3 |
| | | | | | P | 39 | R | 3 | C | 8 | | | | | | P | 40 |

| | | | | | | | | A | 4 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A4 | A4 | A4 | A4 | A4 | A4 | A4 | A | A4 | A4 | A4 | A4 | A4 | A4 | A4 | A4 | A4 | A4 |
| A4 | A4 | A4 | A4 | A4 | A4 | A4 | B | A4 | A4 | A4 | A4 | A4 | A4 | A4 | A4 | A4 | A4 |
| A4 | A4 | A4 | A4 | A4 | A4 | A4 | C | A4 | A4 | A4 | A4 | A4 | A4 | A4 | A4 | A4 | A4 |
| A4 | A4 | A4 | A4 | A4 | A4 | A4 | D | A4 | A4 | A4 | A4 | A4 | A4 | A4 | A4 | A4 | A4 |
| A4 | A4 | A4 | A4 | A4 | A4 | A4 | E | A4 | A4 | A4 | A4 | A4 | A4 | A4 | A4 | A4 | A4 |
| A4 | A4 | A4 | A4 | A4 | A4 | A4 | F | A4 | A4 | A4 | A4 | A4 | A4 | A4 | A4 | A4 | A4 |
| A4 | A4 | A4 | A4 | A4 | A4 | A4 | G | A4 | A4 | A4 | A4 | A4 | A4 | A4 | A4 | A4 | A4 |
| A4 | A4 | A4 | A4 | A4 | A4 | A4 | H | A4 | A4 | A4 | A4 | A4 | A4 | A4 | A4 | A4 | A4 |
| | | | | | P | 55 | R | 4 | C | 8 | | | | | | P | 56 |

| | | | | | | | | A | 5 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A5 | A5 | A5 | A5 | A5 | A5 | A5 | A | A5 | A5 | A5 | A5 | A5 | A5 | A5 | A5 | A5 | A5 |
| A5 | A5 | A5 | A5 | A5 | A5 | A5 | B | A5 | A5 | A5 | A5 | A5 | A5 | A5 | A5 | A5 | A5 |
| A5 | A5 | A5 | A5 | A5 | A5 | A5 | C | A5 | A5 | A5 | A5 | A5 | A5 | A5 | A5 | A5 | A5 |
| A5 | A5 | A5 | A5 | A5 | A5 | A5 | D | A5 | A5 | A5 | A5 | A5 | A5 | A5 | A5 | A5 | A5 |
| A5 | A5 | A5 | A5 | A5 | A5 | A5 | E | A5 | A5 | A5 | A5 | A5 | A5 | A5 | A5 | A5 | A5 |
| A5 | A5 | A5 | A5 | A5 | A5 | A5 | F | A5 | A5 | A5 | A5 | A5 | A5 | A5 | A5 | A5 | A5 |
| A5 | A5 | A5 | A5 | A5 | A5 | A5 | G | A5 | A5 | A5 | A5 | A5 | A5 | A5 | A5 | A5 | A5 |
| A5 | A5 | A5 | A5 | A5 | A5 | A5 | H | A5 | A5 | A5 | A5 | A5 | A5 | A5 | A5 | A5 | A5 |
| | | | | | P | 71 | R | 5 | C | 8 | | | | | | P | 72 |

| | | | | | | | | A | 6 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A6 | A6 | A6 | A6 | A6 | A6 | A6 | A | A6 | A6 | A6 | A6 | A6 | A6 | A6 | A6 | A6 | A6 |
| A6 | A6 | A6 | A6 | A6 | A6 | A6 | B | A6 | A6 | A6 | A6 | A6 | A6 | A6 | A6 | A6 | A6 |
| A6 | A6 | A6 | A6 | A6 | A6 | A6 | C | A6 | A6 | A6 | A6 | A6 | A6 | A6 | A6 | A6 | A6 |
| A6 | A6 | A6 | A6 | A6 | A6 | A6 | D | A6 | A6 | A6 | A6 | A6 | A6 | A6 | A6 | A6 | A6 |
| A6 | A6 | A6 | A6 | A6 | A6 | A6 | E | A6 | A6 | A6 | A6 | A6 | A6 | A6 | A6 | A6 | A6 |
| A6 | A6 | A6 | A6 | A6 | A6 | A6 | F | A6 | A6 | A6 | A6 | A6 | A6 | A6 | A6 | A6 | A6 |
| A6 | A6 | A6 | A6 | A6 | A6 | A6 | G | A6 | A6 | A6 | A6 | A6 | A6 | A6 | A6 | A6 | A6 |
| A6 | A6 | A6 | A6 | A6 | A6 | A6 | H | A6 | A6 | A6 | A6 | A6 | A6 | A6 | A6 | A6 | A6 |
| | | | | | P | 87 | R | 6 | C | 8 | | | | | | P | 88 |

-continued

BB1

| | | | | | | | | A | 7 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A7 | A7 | A7 | A7 | A7 | A7 | A7 | A | A7 | A7 | A7 | A7 | A7 | A7 | A7 | A7 | A7 | A7 |
| A7 | A7 | A7 | A7 | A7 | A7 | A7 | B | A7 | A7 | A7 | A7 | A7 | A7 | A7 | A7 | A7 | A7 |
| A7 | A7 | A7 | A7 | A7 | A7 | A7 | C | A7 | A7 | A7 | A7 | A7 | A7 | A7 | A7 | A7 | A7 |
| A7 | A7 | A7 | A7 | A7 | A7 | A7 | D | A7 | A7 | A7 | A7 | A7 | A7 | A7 | A7 | A7 | A7 |
| A7 | A7 | A7 | A7 | A7 | A7 | A7 | E | A7 | A7 | A7 | A7 | A7 | A7 | A7 | A7 | A7 | A7 |
| A7 | A7 | A7 | A7 | A7 | A7 | A7 | F | A7 | A7 | A7 | A7 | A7 | A7 | A7 | A7 | A7 | A7 |
| A7 | A7 | A7 | A7 | A7 | A7 | A7 | G | A7 | A7 | A7 | A7 | A7 | A7 | A7 | A7 | A7 | A7 |
| A7 | A7 | A7 | A7 | A7 | A7 | A7 | H | A7 | A7 | A7 | A7 | A7 | A7 | A7 | A7 | A7 | A7 |
| | | | | | P | 103 | R | 7 | C | 8 | | | | | | P | 104 |

| | | | | | | | | A | 8 | | | | | | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| A8 | A8 | A8 | A8 | A8 | A8 | A8 | A | A8 | A8 | A8 | A8 | A8 | A8 | A8 | A8 | A8 | A8 |
| A8 | A8 | A8 | A8 | A8 | A8 | A8 | B | A8 | A8 | A8 | A8 | A8 | A8 | A8 | A8 | A8 | A8 |
| A8 | A8 | A8 | A8 | A8 | A8 | A8 | C | A8 | A8 | A8 | A8 | A8 | A8 | A8 | A8 | A8 | A8 |
| A8 | A8 | A8 | A8 | A8 | A8 | A8 | D | A8 | A8 | A8 | A8 | A8 | A8 | A8 | A8 | A8 | A8 |
| A8 | A8 | A8 | A8 | A8 | A8 | A8 | E | A8 | A8 | A8 | A8 | A8 | A8 | A8 | A8 | A8 | A8 |
| A8 | A8 | A8 | A8 | A8 | A8 | A8 | F | A8 | A8 | A8 | A8 | A8 | A8 | A8 | A8 | A8 | A8 |
| A8 | A8 | A8 | A8 | A8 | A8 | A8 | G | A8 | A8 | A8 | A8 | A8 | A8 | A8 | A8 | A8 | A8 |
| A8 | A8 | A8 | A8 | A8 | A8 | A8 | H | A8 | A8 | A8 | A8 | A8 | A8 | A8 | A8 | A8 | A8 |
| | | | | | P | 119 | R | 8 | C | 8 | | | | | | P | 120 |

| | A | 1 | | | | | | | | | | A | 1 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | A1 | A1 | A1 | A1 | A1 | A1 | A1 | A1 | A1 | A1 | A | A1 | A1 | A1 | A1 | A1 |
| B | A1 | A1 | A1 | A1 | A1 | A1 | A1 | A1 | A1 | A1 | B | A1 | A1 | A1 | A1 | A1 |
| C | A1 | A1 | A1 | A1 | A1 | A1 | A1 | A1 | A1 | A1 | C | A1 | A1 | A1 | A1 | A1 |
| D | A1 | A1 | A1 | A1 | A1 | A1 | A1 | A1 | A1 | A1 | D | A1 | A1 | A1 | A1 | A1 |
| E | A1 | A1 | A1 | A1 | A1 | A1 | A1 | A1 | A1 | A1 | E | A1 | A1 | A1 | A1 | A1 |
| F | A1 | A1 | A1 | A1 | A1 | A1 | A1 | A1 | A1 | A1 | F | A1 | A1 | A1 | A1 | A1 |
| G | A1 | A1 | A1 | A1 | A1 | A1 | A1 | A1 | A1 | A1 | G | A1 | A1 | A1 | A1 | A1 |
| H | A1 | A1 | A1 | A1 | A1 | A1 | A1 | A1 | A1 | A1 | H | A1 | A1 | A1 | A1 | A1 |
| R | 1 | C | 9 | | | | | | P | 9 | R | 1 | C | 10 | | |

| | A | 2 | | | | | | | | | | A | 2 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | A2 | A2 | A2 | A2 | A2 | A2 | A2 | A2 | A2 | A2 | A | A2 | A2 | A2 | A2 | A2 |
| B | A2 | A2 | A2 | A2 | A2 | A2 | A2 | A2 | A2 | A2 | B | A2 | A2 | A2 | A2 | A2 |
| C | A2 | A2 | A2 | A2 | A2 | A2 | A2 | A2 | A2 | A2 | C | A2 | A2 | A2 | A2 | A2 |
| D | A2 | A2 | A2 | A2 | A2 | A2 | A2 | A2 | A2 | A2 | D | A2 | A2 | A2 | A2 | A2 |
| E | A2 | A2 | A2 | A2 | A2 | A2 | A2 | A2 | A2 | A2 | E | A2 | A2 | A2 | A2 | A2 |
| F | A2 | A2 | A2 | A2 | A2 | A2 | A2 | A2 | A2 | A2 | F | A2 | A2 | A2 | A2 | A2 |
| G | A2 | A2 | A2 | A2 | A2 | A2 | A2 | A2 | A2 | A2 | G | A2 | A2 | A2 | A2 | A2 |
| H | A2 | A2 | A2 | A2 | A2 | A2 | A2 | A2 | A2 | A2 | H | A2 | A2 | A2 | A2 | A2 |
| R | 2 | C | 9 | | | | | | P | 25 | R | 2 | C | 10 | | |

| | A | 3 | | | | | | | | | | A | 3 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | A3 | A3 | A3 | A3 | A3 | A3 | A3 | A3 | A3 | A3 | A | A3 | A3 | A3 | A3 | A3 |
| B | A3 | A3 | A3 | A3 | A3 | A3 | A3 | A3 | A3 | A3 | B | A3 | A3 | A3 | A3 | A3 |
| C | A3 | A3 | A3 | A3 | A3 | A3 | A3 | A3 | A3 | A3 | C | A3 | A3 | A3 | A3 | A3 |
| D | A3 | A3 | A3 | A3 | A3 | A3 | A3 | A3 | A3 | A3 | D | A3 | A3 | A3 | A3 | A3 |
| E | A3 | A3 | A3 | A3 | A3 | A3 | A3 | A3 | A3 | A3 | E | A3 | A3 | A3 | A3 | A3 |
| F | A3 | A3 | A3 | A3 | A3 | A3 | A3 | A3 | A3 | A3 | F | A3 | A3 | A3 | A3 | A3 |
| G | A3 | A3 | A3 | A3 | A3 | A3 | A3 | A3 | A3 | A3 | G | A3 | A3 | A3 | A3 | A3 |
| H | A3 | A3 | A3 | A3 | A3 | A3 | A3 | A3 | A3 | A3 | H | A3 | A3 | A3 | A3 | A3 |
| R | 3 | C | 9 | | | | | | P | 41 | R | 3 | C | 10 | | |

-continued

| BB1 | | | | | | | | | | | | | | | | |
|---|---|---|---|---|---|---|---|---|---|---|---|---|---|---|---|---|
| | A | 4 | | | | | | | | | | A | 4 | | | |
| | 2 | 3 | 4 | 5 | 6 | 7 | 8 | 9 | 10 | 11 | | 2 | 3 | 4 | 5 | 6 |
| A | A4 | A4 | A4 | A4 | A4 | A4 | A4 | A4 | A4 | A4 | A | A4 | A4 | A4 | A4 | A4 |
| B | A4 | A4 | A4 | A4 | A4 | A4 | A4 | A4 | A4 | A4 | B | A4 | A4 | A4 | A4 | A4 |
| C | A4 | A4 | A4 | A4 | A4 | A4 | A4 | A4 | A4 | A4 | C | A4 | A4 | A4 | A4 | A4 |
| D | A4 | A4 | A4 | A4 | A4 | A4 | A4 | A4 | A4 | A4 | D | A4 | A4 | A4 | A4 | A4 |
| E | A4 | A4 | A4 | A4 | A4 | A4 | A4 | A4 | A4 | A4 | E | A4 | A4 | A4 | A4 | A4 |
| F | A4 | A4 | A4 | A4 | A4 | A4 | A4 | A4 | A4 | A4 | F | A4 | A4 | A4 | A4 | A4 |
| G | A4 | A4 | A4 | A4 | A4 | A4 | A4 | A4 | A4 | A4 | G | A4 | A4 | A4 | A4 | A4 |
| H | A4 | A4 | A4 | A4 | A4 | A4 | A4 | A4 | A4 | A4 | H | A4 | A4 | A4 | A4 | A4 |
| R | 4 | C | 9 | | | | | | P | 57 | R | 4 | C | 10 | | |
| | A | 5 | | | | | | | | | | A | 5 | | | |
| | 2 | 3 | 4 | 5 | 6 | 7 | 8 | 9 | 10 | 11 | | 2 | 3 | 4 | 5 | 6 |
| A | A5 | A5 | A5 | A5 | A5 | A5 | A5 | A5 | A5 | A5 | A | A5 | A5 | A5 | A5 | A5 |
| B | A5 | A5 | A5 | A5 | A5 | A5 | A5 | A5 | A5 | A5 | B | A5 | A5 | A5 | A5 | A5 |
| C | A5 | A5 | A5 | A5 | A5 | A5 | A5 | A5 | A5 | A5 | C | A5 | A5 | A5 | A5 | A5 |
| D | A5 | A5 | A5 | A5 | A5 | A5 | A5 | A5 | A5 | A5 | D | A5 | A5 | A5 | A5 | A5 |
| E | A5 | A5 | A5 | A5 | A5 | A5 | A5 | A5 | A5 | A5 | E | A5 | A5 | A5 | A5 | A5 |
| F | A5 | A5 | A5 | A5 | A5 | A5 | A5 | A5 | A5 | A5 | F | A5 | A5 | A5 | A5 | A5 |
| G | A5 | A5 | A5 | A5 | A5 | A5 | A5 | A5 | A5 | A5 | G | A5 | A5 | A5 | A5 | A5 |
| H | A5 | A5 | A5 | A5 | A5 | A5 | A5 | A5 | A5 | A5 | H | A5 | A5 | A5 | A5 | A5 |
| R | 5 | C | 9 | | | | | | P | 73 | R | 5 | C | 10 | | |
| | A | 6 | | | | | | | | | | A | 6 | | | |
| | 2 | 3 | 4 | 5 | 6 | 7 | 8 | 9 | 10 | 11 | | 2 | 3 | 4 | 5 | 6 |
| A | A6 | A6 | A6 | A6 | A6 | A6 | A6 | A6 | A6 | A6 | A | A6 | A6 | A6 | A6 | A6 |
| B | A6 | A6 | A6 | A6 | A6 | A6 | A6 | A6 | A6 | A6 | B | A6 | A6 | A6 | A6 | A6 |
| C | A6 | A6 | A6 | A6 | A6 | A6 | A6 | A6 | A6 | A6 | C | A6 | A6 | A6 | A6 | A6 |
| D | A6 | A6 | A6 | A6 | A6 | A6 | A6 | A6 | A6 | A6 | D | A6 | A6 | A6 | A6 | A6 |
| E | A6 | A6 | A6 | A6 | A6 | A6 | A6 | A6 | A6 | A6 | E | A6 | A6 | A6 | A6 | A6 |
| F | A6 | A6 | A6 | A6 | A6 | A6 | A6 | A6 | A6 | A6 | F | A6 | A6 | A6 | A6 | A6 |
| G | A6 | A6 | A6 | A6 | A6 | A6 | A6 | A6 | A6 | A6 | G | A6 | A6 | A6 | A6 | A6 |
| H | A6 | A6 | A6 | A6 | A6 | A6 | A6 | A6 | A6 | A6 | H | A6 | A6 | A6 | A6 | A6 |
| R | 6 | C | 9 | | | | | | P | 89 | R | 6 | C | 10 | | |
| | A | 7 | | | | | | | | | | A | 7 | | | |
| | 2 | 3 | 4 | 5 | 6 | 7 | 8 | 9 | 10 | 11 | | 2 | 3 | 4 | 5 | 6 |
| A | A7 | A7 | A7 | A7 | A7 | A7 | A7 | A7 | A7 | A7 | A | A7 | A7 | A7 | A7 | A7 |
| B | A7 | A7 | A7 | A7 | A7 | A7 | A7 | A7 | A7 | A7 | B | A7 | A7 | A7 | A7 | A7 |
| C | A7 | A7 | A7 | A7 | A7 | A7 | A7 | A7 | A7 | A7 | C | A7 | A7 | A7 | A7 | A7 |
| D | A7 | A7 | A7 | A7 | A7 | A7 | A7 | A7 | A7 | A7 | D | A7 | A7 | A7 | A7 | A7 |
| E | A7 | A7 | A7 | A7 | A7 | A7 | A7 | A7 | A7 | A7 | E | A7 | A7 | A7 | A7 | A7 |
| F | A7 | A7 | A7 | A7 | A7 | A7 | A7 | A7 | A7 | A7 | F | A7 | A7 | A7 | A7 | A7 |
| G | A7 | A7 | A7 | A7 | A7 | A7 | A7 | A7 | A7 | A7 | G | A7 | A7 | A7 | A7 | A7 |
| H | A7 | A7 | A7 | A7 | A7 | A7 | A7 | A7 | A7 | A7 | H | A7 | A7 | A7 | A7 | A7 |
| R | 7 | C | 9 | | | | | | P | 105 | R | 7 | C | 10 | | |
| | A | 8 | | | | | | | | | | A | 8 | | | |
| | 2 | 3 | 4 | 5 | 6 | 7 | 8 | 9 | 10 | 11 | | 2 | 3 | 4 | 5 | 6 |
| A | A8 | A8 | A8 | A8 | A8 | A8 | A8 | A8 | A8 | A8 | A | A8 | A8 | A8 | A8 | A8 |
| B | A8 | A8 | A8 | A8 | A8 | A8 | A8 | A8 | A8 | A8 | B | A8 | A8 | A8 | A8 | A8 |
| C | A8 | A8 | A8 | A8 | A8 | A8 | A8 | A8 | A8 | A8 | C | A8 | A8 | A8 | A8 | A8 |
| D | A8 | A8 | A8 | A8 | A8 | A8 | A8 | A8 | A8 | A8 | D | A8 | A8 | A8 | A8 | A8 |
| E | A8 | A8 | A8 | A8 | A8 | A8 | A8 | A8 | A8 | A8 | E | A8 | A8 | A8 | A8 | A8 |
| F | A8 | A8 | A8 | A8 | A8 | A8 | A8 | A8 | A8 | A8 | F | A8 | A8 | A8 | A8 | A8 |
| G | A8 | A8 | A8 | A8 | A8 | A8 | A8 | A8 | A8 | A8 | G | A8 | A8 | A8 | A8 | A8 |
| H | A8 | A8 | A8 | A8 | A8 | A8 | A8 | A8 | A8 | A8 | H | A8 | A8 | A8 | A8 | A8 |
| R | 8 | C | 9 | | | | | | P | 121 | R | 8 | C | 10 | | |

-continued

| BB1 | | | | | | | | | | | | | | | | |
|---|---|---|---|---|---|---|---|---|---|---|---|---|---|---|---|---|
| | | | | | | A | 1 | | | | | | | | | |
| 7 | 8 | 9 | 10 | 11 | | 2 | 3 | 4 | 5 | 6 | 7 | 8 | 9 | 10 | 11 | |
| A1 | A1 | A1 | A1 | A1 | A | A1 | A1 | A1 | A1 | A1 | A1 | A1 | A1 | A1 | A1 | A |
| A1 | A1 | A1 | A1 | A1 | B | A1 | A1 | A1 | A1 | A1 | A1 | A1 | A1 | A1 | A1 | B |
| A1 | A1 | A1 | A1 | A1 | C | A1 | A1 | A1 | A1 | A1 | A1 | A1 | A1 | A1 | A1 | C |
| A1 | A1 | A1 | A1 | A1 | D | A1 | A1 | A1 | A1 | A1 | A1 | A1 | A1 | A1 | A1 | D |
| A1 | A1 | A1 | A1 | A1 | E | A1 | A1 | A1 | A1 | A1 | A1 | A1 | A1 | A1 | A1 | E |
| A1 | A1 | A1 | A1 | A1 | F | A1 | A1 | A1 | A1 | A1 | A1 | A1 | A1 | A1 | A1 | F |
| A1 | A1 | A1 | A1 | A1 | G | A1 | A1 | A1 | A1 | A1 | A1 | A1 | A1 | A1 | A1 | G |
| A1 | A1 | A1 | A1 | A1 | H | A1 | A1 | A1 | A1 | A1 | A1 | A1 | A1 | A1 | A1 | H |
| | | | P | 10 | R | 1 | C | 11 | | | | | | P | 11 | R |
| | | | | | | A | 2 | | | | | | | | | |
| 7 | 8 | 9 | 10 | 11 | | 2 | 3 | 4 | 5 | 6 | 7 | 8 | 9 | 10 | 11 | |
| A2 | A2 | A2 | A2 | A2 | A | A2 | A2 | A2 | A2 | A2 | A2 | A2 | A2 | A2 | A2 | A |
| A2 | A2 | A2 | A2 | A2 | B | A2 | A2 | A2 | A2 | A2 | A2 | A2 | A2 | A2 | A2 | B |
| A2 | A2 | A2 | A2 | A2 | C | A2 | A2 | A2 | A2 | A2 | A2 | A2 | A2 | A2 | A2 | C |
| A2 | A2 | A2 | A2 | A2 | D | A2 | A2 | A2 | A2 | A2 | A2 | A2 | A2 | A2 | A2 | D |
| A2 | A2 | A2 | A2 | A2 | E | A2 | A2 | A2 | A2 | A2 | A2 | A2 | A2 | A2 | A2 | E |
| A2 | A2 | A2 | A2 | A2 | F | A2 | A2 | A2 | A2 | A2 | A2 | A2 | A2 | A2 | A2 | F |
| A2 | A2 | A2 | A2 | A2 | G | A2 | A2 | A2 | A2 | A2 | A2 | A2 | A2 | A2 | A2 | G |
| A2 | A2 | A2 | A2 | A2 | H | A2 | A2 | A2 | A2 | A2 | A2 | A2 | A2 | A2 | A2 | H |
| | | | P | 26 | R | 2 | C | 11 | | | | | | P | 27 | R |
| | | | | | | A | 3 | | | | | | | | | |
| 7 | 8 | 9 | 10 | 11 | | 2 | 3 | 4 | 5 | 6 | 7 | 8 | 9 | 10 | 11 | |
| A3 | A3 | A3 | A3 | A3 | A | A3 | A3 | A3 | A3 | A3 | A3 | A3 | A3 | A3 | A3 | A |
| A3 | A3 | A3 | A3 | A3 | B | A3 | A3 | A3 | A3 | A3 | A3 | A3 | A3 | A3 | A3 | B |
| A3 | A3 | A3 | A3 | A3 | C | A3 | A3 | A3 | A3 | A3 | A3 | A3 | A3 | A3 | A3 | C |
| A3 | A3 | A3 | A3 | A3 | D | A3 | A3 | A3 | A3 | A3 | A3 | A3 | A3 | A3 | A3 | D |
| A3 | A3 | A3 | A3 | A3 | E | A3 | A3 | A3 | A3 | A3 | A3 | A3 | A3 | A3 | A3 | E |
| A3 | A3 | A3 | A3 | A3 | F | A3 | A3 | A3 | A3 | A3 | A3 | A3 | A3 | A3 | A3 | F |
| A3 | A3 | A3 | A3 | A3 | G | A3 | A3 | A3 | A3 | A3 | A3 | A3 | A3 | A3 | A3 | G |
| A3 | A3 | A3 | A3 | A3 | H | A3 | A3 | A3 | A3 | A3 | A3 | A3 | A3 | A3 | A3 | H |
| | | | P | 42 | R | 3 | C | 11 | | | | | | P | 43 | R |
| | | | | | | A | 4 | | | | | | | | | |
| 7 | 8 | 9 | 10 | 11 | | 2 | 3 | 4 | 5 | 6 | 7 | 8 | 9 | 10 | 11 | |
| A4 | A4 | A4 | A4 | A4 | A | A4 | A4 | A4 | A4 | A4 | A4 | A4 | A4 | A4 | A4 | A |
| A4 | A4 | A4 | A4 | A4 | B | A4 | A4 | A4 | A4 | A4 | A4 | A4 | A4 | A4 | A4 | B |
| A4 | A4 | A4 | A4 | A4 | C | A4 | A4 | A4 | A4 | A4 | A4 | A4 | A4 | A4 | A4 | C |
| A4 | A4 | A4 | A4 | A4 | D | A4 | A4 | A4 | A4 | A4 | A4 | A4 | A4 | A4 | A4 | D |
| A4 | A4 | A4 | A4 | A4 | E | A4 | A4 | A4 | A4 | A4 | A4 | A4 | A4 | A4 | A4 | E |
| A4 | A4 | A4 | A4 | A4 | F | A4 | A4 | A4 | A4 | A4 | A4 | A4 | A4 | A4 | A4 | F |
| A4 | A4 | A4 | A4 | A4 | G | A4 | A4 | A4 | A4 | A4 | A4 | A4 | A4 | A4 | A4 | G |
| A4 | A4 | A4 | A4 | A4 | H | A4 | A4 | A4 | A4 | A4 | A4 | A4 | A4 | A4 | A4 | H |
| | | | P | 58 | R | 4 | C | 11 | | | | | | P | 59 | R |
| | | | | | | A | 5 | | | | | | | | | |
| 7 | 8 | 9 | 10 | 11 | | 2 | 3 | 4 | 5 | 6 | 7 | 8 | 9 | 10 | 11 | |
| A5 | A5 | A5 | A5 | A5 | A | A5 | A5 | A5 | A5 | A5 | A5 | A5 | A5 | A5 | A5 | A |
| A5 | A5 | A5 | A5 | A5 | B | A5 | A5 | A5 | A5 | A5 | A5 | A5 | A5 | A5 | A5 | B |
| A5 | A5 | A5 | A5 | A5 | C | A5 | A5 | A5 | A5 | A5 | A5 | A5 | A5 | A5 | A5 | C |
| A5 | A5 | A5 | A5 | A5 | D | A5 | A5 | A5 | A5 | A5 | A5 | A5 | A5 | A5 | A5 | D |
| A5 | A5 | A5 | A5 | A5 | E | A5 | A5 | A5 | A5 | A5 | A5 | A5 | A5 | A5 | A5 | E |
| A5 | A5 | A5 | A5 | A5 | F | A5 | A5 | A5 | A5 | A5 | A5 | A5 | A5 | A5 | A5 | F |
| A5 | A5 | A5 | A5 | A5 | G | A5 | A5 | A5 | A5 | A5 | A5 | A5 | A5 | A5 | A5 | G |
| A5 | A5 | A5 | A5 | A5 | H | A5 | A5 | A5 | A5 | A5 | A5 | A5 | A5 | A5 | A5 | H |
| | | | P | 74 | R | 5 | C | 11 | | | | | | P | 75 | R |

-continued

BB1

| 7 | 8 | 9 | 10 | 11 | | A 2 | 6 3 | 4 | 5 | 6 | 7 | 8 | 9 | 10 | 11 | |
|---|---|---|---|---|---|---|---|---|---|---|---|---|---|---|---|---|
| A6 | A6 | A6 | A6 | A6 | A | A6 | A6 | A6 | A6 | A6 | A6 | A6 | A6 | A6 | A6 | A |
| A6 | A6 | A6 | A6 | A6 | B | A6 | A6 | A6 | A6 | A6 | A6 | A6 | A6 | A6 | A6 | B |
| A6 | A6 | A6 | A6 | A6 | C | A6 | A6 | A6 | A6 | A6 | A6 | A6 | A6 | A6 | A6 | C |
| A6 | A6 | A6 | A6 | A6 | D | A6 | A6 | A6 | A6 | A6 | A6 | A6 | A6 | A6 | A6 | D |
| A6 | A6 | A6 | A6 | A6 | E | A6 | A6 | A6 | A6 | A6 | A6 | A6 | A6 | A6 | A6 | E |
| A6 | A6 | A6 | A6 | A6 | F | A6 | A6 | A6 | A6 | A6 | A6 | A6 | A6 | A6 | A6 | F |
| A6 | A6 | A6 | A6 | A6 | G | A6 | A6 | A6 | A6 | A6 | A6 | A6 | A6 | A6 | A6 | G |
| A6 | A6 | A6 | A6 | A6 | H | A6 | A6 | A6 | A6 | A6 | A6 | A6 | A6 | A6 | A6 | H |
| | | | P | 90 | R | 6 | C | 11 | | | | | | P | 91 | R |

| 7 | 8 | 9 | 10 | 11 | | A 2 | 7 3 | 4 | 5 | 6 | 7 | 8 | 9 | 10 | 11 | |
|---|---|---|---|---|---|---|---|---|---|---|---|---|---|---|---|---|
| A7 | A7 | A7 | A7 | A7 | A | A7 | A7 | A7 | A7 | A7 | A7 | A7 | A7 | A7 | A7 | A |
| A7 | A7 | A7 | A7 | A7 | B | A7 | A7 | A7 | A7 | A7 | A7 | A7 | A7 | A7 | A7 | B |
| A7 | A7 | A7 | A7 | A7 | C | A7 | A7 | A7 | A7 | A7 | A7 | A7 | A7 | A7 | A7 | C |
| A7 | A7 | A7 | A7 | A7 | D | A7 | A7 | A7 | A7 | A7 | A7 | A7 | A7 | A7 | A7 | D |
| A7 | A7 | A7 | A7 | A7 | E | A7 | A7 | A7 | A7 | A7 | A7 | A7 | A7 | A7 | A7 | E |
| A7 | A7 | A7 | A7 | A7 | F | A7 | A7 | A7 | A7 | A7 | A7 | A7 | A7 | A7 | A7 | F |
| A7 | A7 | A7 | A7 | A7 | G | A7 | A7 | A7 | A7 | A7 | A7 | A7 | A7 | A7 | A7 | G |
| A7 | A7 | A7 | A7 | A7 | H | A7 | A7 | A7 | A7 | A7 | A7 | A7 | A7 | A7 | A7 | H |
| | | | P | 106 | R | 7 | C | 11 | | | | | | P | 107 | R |

| 7 | 8 | 9 | 10 | 11 | | A 2 | 8 3 | 4 | 5 | 6 | 7 | 8 | 9 | 10 | 11 | |
|---|---|---|---|---|---|---|---|---|---|---|---|---|---|---|---|---|
| A8 | A8 | A8 | A8 | A8 | A | A8 | A8 | A8 | A8 | A8 | A8 | A8 | A8 | A8 | A8 | A |
| A8 | A8 | A8 | A8 | A8 | B | A8 | A8 | A8 | A8 | A8 | A8 | A8 | A8 | A8 | A8 | B |
| A8 | A8 | A8 | A8 | A8 | C | A8 | A8 | A8 | A8 | A8 | A8 | A8 | A8 | A8 | A8 | C |
| A8 | A8 | A8 | A8 | A8 | D | A8 | A8 | A8 | A8 | A8 | A8 | A8 | A8 | A8 | A8 | D |
| A8 | A8 | A8 | A8 | A8 | E | A8 | A8 | A8 | A8 | A8 | A8 | A8 | A8 | A8 | A8 | E |
| A8 | A8 | A8 | A8 | A8 | F | A8 | A8 | A8 | A8 | A8 | A8 | A8 | A8 | A8 | A8 | F |
| A8 | A8 | A8 | A8 | A8 | G | A8 | A8 | A8 | A8 | A8 | A8 | A8 | A8 | A8 | A8 | G |
| A8 | A8 | A8 | A8 | A8 | H | A8 | A8 | A8 | A8 | A8 | A8 | A8 | A8 | A8 | A8 | H |
| | | | P | 122 | R | 8 | C | 11 | | | | | | P | 123 | R |

| A 2 | 1 3 | 4 | 5 | 6 | 7 | 8 | 9 | 10 | 11 | | A 2 | 1 3 | 4 | 5 | 6 | 7 | 8 |
|---|---|---|---|---|---|---|---|---|---|---|---|---|---|---|---|---|---|
| A1 | A1 | A1 | A1 | A1 | A1 | A1 | A1 | A1 | A1 | A | A1 | A1 | A1 | A1 | A1 | A1 | A1 |
| A1 | A1 | A1 | A1 | A1 | A1 | A1 | A1 | A1 | A1 | B | A1 | A1 | A1 | A1 | A1 | A1 | A1 |
| A1 | A1 | A1 | A1 | A1 | A1 | A1 | A1 | A1 | A1 | C | A1 | A1 | A1 | A1 | A1 | A1 | A1 |
| A1 | A1 | A1 | A1 | A1 | A1 | A1 | A1 | A1 | A1 | D | A1 | A1 | A1 | A1 | A1 | A1 | A1 |
| A1 | A1 | A1 | A1 | A1 | A1 | A1 | A1 | A1 | A1 | E | A1 | A1 | A1 | A1 | A1 | A1 | A1 |
| A1 | A1 | A1 | A1 | A1 | A1 | A1 | A1 | A1 | A1 | F | A1 | A1 | A1 | A1 | A1 | A1 | A1 |
| A1 | A1 | A1 | A1 | A1 | A1 | A1 | A1 | A1 | A1 | G | A1 | A1 | A1 | A1 | A1 | A1 | A1 |
| A1 | A1 | A1 | A1 | A1 | A1 | A1 | A1 | A1 | A1 | H | A1 | A1 | A1 | A1 | A1 | A1 | A1 |
| 1 | C | 12 | | | | | | P | 12 | R | 1 | C | 13 | | | | |

| A 2 | 2 3 | 4 | 5 | 6 | 7 | 8 | 9 | 10 | 11 | | A 2 | 2 3 | 4 | 5 | 6 | 7 | 8 |
|---|---|---|---|---|---|---|---|---|---|---|---|---|---|---|---|---|---|
| A2 | A2 | A2 | A2 | A2 | A2 | A2 | A2 | A2 | A2 | A | A2 | A2 | A2 | A2 | A2 | A2 | A2 |
| A2 | A2 | A2 | A2 | A2 | A2 | A2 | A2 | A2 | A2 | B | A2 | A2 | A2 | A2 | A2 | A2 | A2 |
| A2 | A2 | A2 | A2 | A2 | A2 | A2 | A2 | A2 | A2 | C | A2 | A2 | A2 | A2 | A2 | A2 | A2 |
| A2 | A2 | A2 | A2 | A2 | A2 | A2 | A2 | A2 | A2 | D | A2 | A2 | A2 | A2 | A2 | A2 | A2 |
| A2 | A2 | A2 | A2 | A2 | A2 | A2 | A2 | A2 | A2 | E | A2 | A2 | A2 | A2 | A2 | A2 | A2 |
| A2 | A2 | A2 | A2 | A2 | A2 | A2 | A2 | A2 | A2 | F | A2 | A2 | A2 | A2 | A2 | A2 | A2 |
| A2 | A2 | A2 | A2 | A2 | A2 | A2 | A2 | A2 | A2 | G | A2 | A2 | A2 | A2 | A2 | A2 | A2 |
| A2 | A2 | A2 | A2 | A2 | A2 | A2 | A2 | A2 | A2 | H | A2 | A2 | A2 | A2 | A2 | A2 | A2 |
| 2 | C | 12 | | | | | | P | 28 | R | 2 | C | 13 | | | | |

-continued

| BB1 | | | | | | | | | | | | | | | | | |
|---|---|---|---|---|---|---|---|---|---|---|---|---|---|---|---|---|---|
| A | 3 | | | | | | | | | | A | 3 | | | | | |
| 2 | 3 | 4 | 5 | 6 | 7 | 8 | 9 | 10 | 11 | | 2 | 3 | 4 | 5 | 6 | 7 | 8 |
| A3 | A3 | A3 | A3 | A3 | A3 | A3 | A3 | A3 | A3 | A | A3 | A3 | A3 | A3 | A3 | A3 | A3 |
| A3 | A3 | A3 | A3 | A3 | A3 | A3 | A3 | A3 | A3 | B | A3 | A3 | A3 | A3 | A3 | A3 | A3 |
| A3 | A3 | A3 | A3 | A3 | A3 | A3 | A3 | A3 | A3 | C | A3 | A3 | A3 | A3 | A3 | A3 | A3 |
| A3 | A3 | A3 | A3 | A3 | A3 | A3 | A3 | A3 | A3 | D | A3 | A3 | A3 | A3 | A3 | A3 | A3 |
| A3 | A3 | A3 | A3 | A3 | A3 | A3 | A3 | A3 | A3 | E | A3 | A3 | A3 | A3 | A3 | A3 | A3 |
| A3 | A3 | A3 | A3 | A3 | A3 | A3 | A3 | A3 | A3 | F | A3 | A3 | A3 | A3 | A3 | A3 | A3 |
| A3 | A3 | A3 | A3 | A3 | A3 | A3 | A3 | A3 | A3 | G | A3 | A3 | A3 | A3 | A3 | A3 | A3 |
| A3 | A3 | A3 | A3 | A3 | A3 | A3 | A3 | A3 | A3 | H | A3 | A3 | A3 | A3 | A3 | A3 | A3 |
| 3 | C | 12 | | | | | | P | 44 | R | 3 | C | 13 | | | | |
| A | 4 | | | | | | | | | | A | 4 | | | | | |
| 2 | 3 | 4 | 5 | 6 | 7 | 8 | 9 | 10 | 11 | | 2 | 3 | 4 | 5 | 6 | 7 | 8 |
| A4 | A4 | A4 | A4 | A4 | A4 | A4 | A4 | A4 | A4 | A | A4 | A4 | A4 | A4 | A4 | A4 | A4 |
| A4 | A4 | A4 | A4 | A4 | A4 | A4 | A4 | A4 | A4 | B | A4 | A4 | A4 | A4 | A4 | A4 | A4 |
| A4 | A4 | A4 | A4 | A4 | A4 | A4 | A4 | A4 | A4 | C | A4 | A4 | A4 | A4 | A4 | A4 | A4 |
| A4 | A4 | A4 | A4 | A4 | A4 | A4 | A4 | A4 | A4 | D | A4 | A4 | A4 | A4 | A4 | A4 | A4 |
| A4 | A4 | A4 | A4 | A4 | A4 | A4 | A4 | A4 | A4 | E | A4 | A4 | A4 | A4 | A4 | A4 | A4 |
| A4 | A4 | A4 | A4 | A4 | A4 | A4 | A4 | A4 | A4 | F | A4 | A4 | A4 | A4 | A4 | A4 | A4 |
| A4 | A4 | A4 | A4 | A4 | A4 | A4 | A4 | A4 | A4 | G | A4 | A4 | A4 | A4 | A4 | A4 | A4 |
| A4 | A4 | A4 | A4 | A4 | A4 | A4 | A4 | A4 | A4 | H | A4 | A4 | A4 | A4 | A4 | A4 | A4 |
| 4 | C | 12 | | | | | | P | 60 | R | 4 | C | 13 | | | | |
| A | 5 | | | | | | | | | | A | 5 | | | | | |
| 2 | 3 | 4 | 5 | 6 | 7 | 8 | 9 | 10 | 11 | | 2 | 3 | 4 | 5 | 6 | 7 | 8 |
| A5 | A5 | A5 | A5 | A5 | A5 | A5 | A5 | A5 | A5 | A | A5 | A5 | A5 | A5 | A5 | A5 | A5 |
| A5 | A5 | A5 | A5 | A5 | A5 | A5 | A5 | A5 | A5 | B | A5 | A5 | A5 | A5 | A5 | A5 | A5 |
| A5 | A5 | A5 | A5 | A5 | A5 | A5 | A5 | A5 | A5 | C | A5 | A5 | A5 | A5 | A5 | A5 | A5 |
| A5 | A5 | A5 | A5 | A5 | A5 | A5 | A5 | A5 | A5 | D | A5 | A5 | A5 | A5 | A5 | A5 | A5 |
| A5 | A5 | A5 | A5 | A5 | A5 | A5 | A5 | A5 | A5 | E | A5 | A5 | A5 | A5 | A5 | A5 | A5 |
| A5 | A5 | A5 | A5 | A5 | A5 | A5 | A5 | A5 | A5 | F | A5 | A5 | A5 | A5 | A5 | A5 | A5 |
| A5 | A5 | A5 | A5 | A5 | A5 | A5 | A5 | A5 | A5 | G | A5 | A5 | A5 | A5 | A5 | A5 | A5 |
| A5 | A5 | A5 | A5 | A5 | A5 | A5 | A5 | A5 | A5 | H | A5 | A5 | A5 | A5 | A5 | A5 | A5 |
| 5 | C | 12 | | | | | | P | 76 | R | 5 | C | 13 | | | | |
| A | 6 | | | | | | | | | | A | 6 | | | | | |
| 2 | 3 | 4 | 5 | 6 | 7 | 8 | 9 | 10 | 11 | | 2 | 3 | 4 | 5 | 6 | 7 | 8 |
| A6 | A6 | A6 | A6 | A6 | A6 | A6 | A6 | A6 | A6 | A | A6 | A6 | A6 | A6 | A6 | A6 | A6 |
| A6 | A6 | A6 | A6 | A6 | A6 | A6 | A6 | A6 | A6 | B | A6 | A6 | A6 | A6 | A6 | A6 | A6 |
| A6 | A6 | A6 | A6 | A6 | A6 | A6 | A6 | A6 | A6 | C | A6 | A6 | A6 | A6 | A6 | A6 | A6 |
| A6 | A6 | A6 | A6 | A6 | A6 | A6 | A6 | A6 | A6 | D | A6 | A6 | A6 | A6 | A6 | A6 | A6 |
| A6 | A6 | A6 | A6 | A6 | A6 | A6 | A6 | A6 | A6 | E | A6 | A6 | A6 | A6 | A6 | A6 | A6 |
| A6 | A6 | A6 | A6 | A6 | A6 | A6 | A6 | A6 | A6 | F | A6 | A6 | A6 | A6 | A6 | A6 | A6 |
| A6 | A6 | A6 | A6 | A6 | A6 | A6 | A6 | A6 | A6 | G | A6 | A6 | A6 | A6 | A6 | A6 | A6 |
| A6 | A6 | A6 | A6 | A6 | A6 | A6 | A6 | A6 | A6 | H | A6 | A6 | A6 | A6 | A6 | A6 | A6 |
| 6 | C | 12 | | | | | | P | 92 | R | 6 | C | 13 | | | | |
| A | 7 | | | | | | | | | | A | 7 | | | | | |
| 2 | 3 | 4 | 5 | 6 | 7 | 8 | 9 | 10 | 11 | | 2 | 3 | 4 | 5 | 6 | 7 | 8 |
| A7 | A7 | A7 | A7 | A7 | A7 | A7 | A7 | A7 | A7 | A | A7 | A7 | A7 | A7 | A7 | A7 | A7 |
| A7 | A7 | A7 | A7 | A7 | A7 | A7 | A7 | A7 | A7 | B | A7 | A7 | A7 | A7 | A7 | A7 | A7 |
| A7 | A7 | A7 | A7 | A7 | A7 | A7 | A7 | A7 | A7 | C | A7 | A7 | A7 | A7 | A7 | A7 | A7 |
| A7 | A7 | A7 | A7 | A7 | A7 | A7 | A7 | A7 | A7 | D | A7 | A7 | A7 | A7 | A7 | A7 | A7 |
| A7 | A7 | A7 | A7 | A7 | A7 | A7 | A7 | A7 | A7 | E | A7 | A7 | A7 | A7 | A7 | A7 | A7 |
| A7 | A7 | A7 | A7 | A7 | A7 | A7 | A7 | A7 | A7 | F | A7 | A7 | A7 | A7 | A7 | A7 | A7 |
| A7 | A7 | A7 | A7 | A7 | A7 | A7 | A7 | A7 | A7 | G | A7 | A7 | A7 | A7 | A7 | A7 | A7 |
| A7 | A7 | A7 | A7 | A7 | A7 | A7 | A7 | A7 | A7 | H | A7 | A7 | A7 | A7 | A7 | A7 | A7 |
| 7 | C | 12 | | | | | | P | 108 | R | 7 | C | 13 | | | | |

-continued

| BB1 | | | | | | | | | | | | | | | | | | |
|---|---|---|---|---|---|---|---|---|---|---|---|---|---|---|---|---|---|---|
| A<br>2 | 8<br>3 | 4 | 5 | 6 | 7 | 8 | 9 | 10 | 11 | | | A<br>2 | 8<br>3 | 4 | 5 | 6 | 7 | 8 |
| A8 | A8 | A8 | A8 | A8 | A8 | A8 | A8 | A8 | A8 | | A | A8 | A8 | A8 | A8 | A8 | A8 | A8 |
| A8 | A8 | A8 | A8 | A8 | A8 | A8 | A8 | A8 | A8 | | B | A8 | A8 | A8 | A8 | A8 | A8 | A8 |
| A8 | A8 | A8 | A8 | A8 | A8 | A8 | A8 | A8 | A8 | | C | A8 | A8 | A8 | A8 | A8 | A8 | A8 |
| A8 | A8 | A8 | A8 | A8 | A8 | A8 | A8 | A8 | A8 | | D | A8 | A8 | A8 | A8 | A8 | A8 | A8 |
| A8 | A8 | A8 | A8 | A8 | A8 | A8 | A8 | A8 | A8 | | E | A8 | A8 | A8 | A8 | A8 | A8 | A8 |
| A8 | A8 | A8 | A8 | A8 | A8 | A8 | A8 | A8 | A8 | | F | A8 | A8 | A8 | A8 | A8 | A8 | A8 |
| A8 | A8 | A8 | A8 | A8 | A8 | A8 | A8 | A8 | A8 | | G | A8 | A8 | A8 | A8 | A8 | A8 | A8 |
| A8 | A8 | A8 | A8 | A8 | A8 | A8 | A8 | A8 | A8 | | H | A8 | A8 | A8 | A8 | A8 | A8 | A8 |
| 8 | C | 12 | | | | | | P | 124 | | R | 8 | C | 13 | | | | |
| 9 | 10 | 11 | | | A<br>2 | 1<br>3 | 4 | 5 | 6 | 7 | 8 | 9 | 10 | 11 | | | A<br>2 | 1<br>3 |
| A1 | A1 | A1 | | A | A1 | A1 | A1 | A1 | A1 | A1 | A1 | A1 | A1 | A1 | | A | A1 | A1 |
| A1 | A1 | A1 | | B | A1 | A1 | A1 | A1 | A1 | A1 | A1 | A1 | A1 | A1 | | B | A1 | A1 |
| A1 | A1 | A1 | | C | A1 | A1 | A1 | A1 | A1 | A1 | A1 | A1 | A1 | A1 | | C | A1 | A1 |
| A1 | A1 | A1 | | D | A1 | A1 | A1 | A1 | A1 | A1 | A1 | A1 | A1 | A1 | | D | A1 | A1 |
| A1 | A1 | A1 | | E | A1 | A1 | A1 | A1 | A1 | A1 | A1 | A1 | A1 | A1 | | E | A1 | A1 |
| A1 | A1 | A1 | | F | A1 | A1 | A1 | A1 | A1 | A1 | A1 | A1 | A1 | A1 | | F | A1 | A1 |
| A1 | A1 | A1 | | G | A1 | A1 | A1 | A1 | A1 | A1 | A1 | A1 | A1 | A1 | | G | A1 | A1 |
| A1 | A1 | A1 | | H | A1 | A1 | A1 | A1 | A1 | A1 | A1 | A1 | A1 | A1 | | H | A1 | A1 |
| | P | 13 | | R | 1 | C | 14 | | | | | | P | 14 | | R | 1 | C |
| 9 | 10 | 11 | | | A<br>2 | 2<br>3 | 4 | 5 | 6 | 7 | 8 | 9 | 10 | 11 | | | A<br>2 | 2<br>3 |
| A2 | A2 | A2 | | A | A2 | A2 | A2 | A2 | A2 | A2 | A2 | A2 | A2 | A2 | | A | A2 | A2 |
| A2 | A2 | A2 | | B | A2 | A2 | A2 | A2 | A2 | A2 | A2 | A2 | A2 | A2 | | B | A2 | A2 |
| A2 | A2 | A2 | | C | A2 | A2 | A2 | A2 | A2 | A2 | A2 | A2 | A2 | A2 | | C | A2 | A2 |
| A2 | A2 | A2 | | D | A2 | A2 | A2 | A2 | A2 | A2 | A2 | A2 | A2 | A2 | | D | A2 | A2 |
| A2 | A2 | A2 | | E | A2 | A2 | A2 | A2 | A2 | A2 | A2 | A2 | A2 | A2 | | E | A2 | A2 |
| A2 | A2 | A2 | | F | A2 | A2 | A2 | A2 | A2 | A2 | A2 | A2 | A2 | A2 | | F | A2 | A2 |
| A2 | A2 | A2 | | G | A2 | A2 | A2 | A2 | A2 | A2 | A2 | A2 | A2 | A2 | | G | A2 | A2 |
| A2 | A2 | A2 | | H | A2 | A2 | A2 | A2 | A2 | A2 | A2 | A2 | A2 | A2 | | H | A2 | A2 |
| | P | 29 | | R | 2 | C | 14 | | | | | | P | 30 | | R | 2 | C |
| 9 | 10 | 11 | | | A<br>2 | 3<br>3 | 4 | 5 | 6 | 7 | 8 | 9 | 10 | 11 | | | A<br>2 | 3<br>3 |
| A3 | A3 | A3 | | A | A3 | A3 | A3 | A3 | A3 | A3 | A3 | A3 | A3 | A3 | | A | A3 | A3 |
| A3 | A3 | A3 | | B | A3 | A3 | A3 | A3 | A3 | A3 | A3 | A3 | A3 | A3 | | B | A3 | A3 |
| A3 | A3 | A3 | | C | A3 | A3 | A3 | A3 | A3 | A3 | A3 | A3 | A3 | A3 | | C | A3 | A3 |
| A3 | A3 | A3 | | D | A3 | A3 | A3 | A3 | A3 | A3 | A3 | A3 | A3 | A3 | | D | A3 | A3 |
| A3 | A3 | A3 | | E | A3 | A3 | A3 | A3 | A3 | A3 | A3 | A3 | A3 | A3 | | E | A3 | A3 |
| A3 | A3 | A3 | | F | A3 | A3 | A3 | A3 | A3 | A3 | A3 | A3 | A3 | A3 | | F | A3 | A3 |
| A3 | A3 | A3 | | G | A3 | A3 | A3 | A3 | A3 | A3 | A3 | A3 | A3 | A3 | | G | A3 | A3 |
| A3 | A3 | A3 | | H | A3 | A3 | A3 | A3 | A3 | A3 | A3 | A3 | A3 | A3 | | H | A3 | A3 |
| | P | 45 | | R | 3 | C | 14 | | | | | | P | 46 | | R | 3 | C |
| 9 | 10 | 11 | | | A<br>2 | 4<br>3 | 4 | 5 | 6 | 7 | 8 | 9 | 10 | 11 | | | A<br>2 | 4<br>3 |
| A4 | A4 | A4 | | A | A4 | A4 | A4 | A4 | A4 | A4 | A4 | A4 | A4 | A4 | | A | A4 | A4 |
| A4 | A4 | A4 | | B | A4 | A4 | A4 | A4 | A4 | A4 | A4 | A4 | A4 | A4 | | B | A4 | A4 |
| A4 | A4 | A4 | | C | A4 | A4 | A4 | A4 | A4 | A4 | A4 | A4 | A4 | A4 | | C | A4 | A4 |
| A4 | A4 | A4 | | D | A4 | A4 | A4 | A4 | A4 | A4 | A4 | A4 | A4 | A4 | | D | A4 | A4 |
| A4 | A4 | A4 | | E | A4 | A4 | A4 | A4 | A4 | A4 | A4 | A4 | A4 | A4 | | E | A4 | A4 |
| A4 | A4 | A4 | | F | A4 | A4 | A4 | A4 | A4 | A4 | A4 | A4 | A4 | A4 | | F | A4 | A4 |
| A4 | A4 | A4 | | G | A4 | A4 | A4 | A4 | A4 | A4 | A4 | A4 | A4 | A4 | | G | A4 | A4 |
| A4 | A4 | A4 | | H | A4 | A4 | A4 | A4 | A4 | A4 | A4 | A4 | A4 | A4 | | H | A4 | A4 |
| | P | 61 | | R | 4 | C | 14 | | | | | | P | 62 | | R | 4 | C |

-continued

BB1

| | | | | | | | | | | | | | | | | |
|---|---|---|---|---|---|---|---|---|---|---|---|---|---|---|---|---|
| | | | | A | 5 | | | | | | | | | | A | 5 |
| 9 | 10 | 11 | | 2 | 3 | 4 | 5 | 6 | 7 | 8 | 9 | 10 | 11 | | 2 | 3 |
| A5 | A5 | A5 | A | A5 | A5 | A5 | A5 | A5 | A5 | A5 | A5 | A5 | A5 | A | A5 | A5 |
| A5 | A5 | A5 | B | A5 | A5 | A5 | A5 | A5 | A5 | A5 | A5 | A5 | A5 | B | A5 | A5 |
| A5 | A5 | A5 | C | A5 | A5 | A5 | A5 | A5 | A5 | A5 | A5 | A5 | A5 | C | A5 | A5 |
| A5 | A5 | A5 | D | A5 | A5 | A5 | A5 | A5 | A5 | A5 | A5 | A5 | A5 | D | A5 | A5 |
| A5 | A5 | A5 | E | A5 | A5 | A5 | A5 | A5 | A5 | A5 | A5 | A5 | A5 | E | A5 | A5 |
| A5 | A5 | A5 | F | A5 | A5 | A5 | A5 | A5 | A5 | A5 | A5 | A5 | A5 | F | A5 | A5 |
| A5 | A5 | A5 | G | A5 | A5 | A5 | A5 | A5 | A5 | A5 | A5 | A5 | A5 | G | A5 | A5 |
| A5 | A5 | A5 | H | A5 | A5 | A5 | A5 | A5 | A5 | A5 | A5 | A5 | A5 | H | A5 | A5 |
| | P | 77 | R | 5 | C | 14 | | | | | | P | 78 | R | 5 | C |
| | | | | A | 6 | | | | | | | | | | A | 6 |
| 9 | 10 | 11 | | 2 | 3 | 4 | 5 | 6 | 7 | 8 | 9 | 10 | 11 | | 2 | 3 |
| A6 | A6 | A6 | A | A6 | A6 | A6 | A6 | A6 | A6 | A6 | A6 | A6 | A6 | A | A6 | A6 |
| A6 | A6 | A6 | B | A6 | A6 | A6 | A6 | A6 | A6 | A6 | A6 | A6 | A6 | B | A6 | A6 |
| A6 | A6 | A6 | C | A6 | A6 | A6 | A6 | A6 | A6 | A6 | A6 | A6 | A6 | C | A6 | A6 |
| A6 | A6 | A6 | D | A6 | A6 | A6 | A6 | A6 | A6 | A6 | A6 | A6 | A6 | D | A6 | A6 |
| A6 | A6 | A6 | E | A6 | A6 | A6 | A6 | A6 | A6 | A6 | A6 | A6 | A6 | E | A6 | A6 |
| A6 | A6 | A6 | F | A6 | A6 | A6 | A6 | A6 | A6 | A6 | A6 | A6 | A6 | F | A6 | A6 |
| A6 | A6 | A6 | G | A6 | A6 | A6 | A6 | A6 | A6 | A6 | A6 | A6 | A6 | G | A6 | A6 |
| A6 | A6 | A6 | H | A6 | A6 | A6 | A6 | A6 | A6 | A6 | A6 | A6 | A6 | H | A6 | A6 |
| | P | 93 | R | 6 | C | 14 | | | | | | P | 94 | R | 6 | C |
| | | | | A | 7 | | | | | | | | | | A | 7 |
| 9 | 10 | 11 | | 2 | 3 | 4 | 5 | 6 | 7 | 8 | 9 | 10 | 11 | | 2 | 3 |
| A7 | A7 | A7 | A | A7 | A7 | A7 | A7 | A7 | A7 | A7 | A7 | A7 | A7 | A | A7 | A7 |
| A7 | A7 | A7 | B | A7 | A7 | A7 | A7 | A7 | A7 | A7 | A7 | A7 | A7 | B | A7 | A7 |
| A7 | A7 | A7 | C | A7 | A7 | A7 | A7 | A7 | A7 | A7 | A7 | A7 | A7 | C | A7 | A7 |
| A7 | A7 | A7 | D | A7 | A7 | A7 | A7 | A7 | A7 | A7 | A7 | A7 | A7 | D | A7 | A7 |
| A7 | A7 | A7 | E | A7 | A7 | A7 | A7 | A7 | A7 | A7 | A7 | A7 | A7 | E | A7 | A7 |
| A7 | A7 | A7 | F | A7 | A7 | A7 | A7 | A7 | A7 | A7 | A7 | A7 | A7 | F | A7 | A7 |
| A7 | A7 | A7 | G | A7 | A7 | A7 | A7 | A7 | A7 | A7 | A7 | A7 | A7 | G | A7 | A7 |
| A7 | A7 | A7 | H | A7 | A7 | A7 | A7 | A7 | A7 | A7 | A7 | A7 | A7 | H | A7 | A7 |
| | P | 109 | R | 7 | C | 14 | | | | | | P | 110 | R | 7 | C |
| | | | | A | 8 | | | | | | | | | | A | 8 |
| 9 | 10 | 11 | | 2 | 3 | 4 | 5 | 6 | 7 | 8 | 9 | 10 | 11 | | 2 | 3 |
| A8 | A8 | A8 | A | A8 | A8 | A8 | A8 | A8 | A8 | A8 | A8 | A8 | A8 | A | A8 | A8 |
| A8 | A8 | A8 | B | A8 | A8 | A8 | A8 | A8 | A8 | A8 | A8 | A8 | A8 | B | A8 | A8 |
| A8 | A8 | A8 | C | A8 | A8 | A8 | A8 | A8 | A8 | A8 | A8 | A8 | A8 | C | A8 | A8 |
| A8 | A8 | A8 | D | A8 | A8 | A8 | A8 | A8 | A8 | A8 | A8 | A8 | A8 | D | A8 | A8 |
| A8 | A8 | A8 | E | A8 | A8 | A8 | A8 | A8 | A8 | A8 | A8 | A8 | A8 | E | A8 | A8 |
| A8 | A8 | A8 | F | A8 | A8 | A8 | A8 | A8 | A8 | A8 | A8 | A8 | A8 | F | A8 | A8 |
| A8 | A8 | A8 | G | A8 | A8 | A8 | A8 | A8 | A8 | A8 | A8 | A8 | A8 | G | A8 | A8 |
| A8 | A8 | A8 | H | A8 | A8 | A8 | A8 | A8 | A8 | A8 | A8 | A8 | A8 | H | A8 | A8 |
| | P | 125 | R | 8 | C | 14 | | | | | | P | 126 | R | 8 | C |

| | | | | | | | | | | | | | | | | | |
|---|---|---|---|---|---|---|---|---|---|---|---|---|---|---|---|---|---|
| | | | | | | | | | A | 1 | | | | | | | |
| 4 | 5 | 6 | 7 | 8 | 9 | 10 | 11 | | 2 | 3 | 4 | 5 | 6 | 7 | 8 | 9 | 10 |
| A1 | A1 | A1 | A1 | A1 | A1 | A1 | A1 | A | A1 | A1 | A1 | A1 | A1 | A1 | A1 | A1 | A1 |
| A1 | A1 | A1 | A1 | A1 | A1 | A1 | A1 | B | A1 | A1 | A1 | A1 | A1 | A1 | A1 | A1 | A1 |
| A1 | A1 | A1 | A1 | A1 | A1 | A1 | A1 | C | A1 | A1 | A1 | A1 | A1 | A1 | A1 | A1 | A1 |
| A1 | A1 | A1 | A1 | A1 | A1 | A1 | A1 | D | A1 | A1 | A1 | A1 | A1 | A1 | A1 | A1 | A1 |
| A1 | A1 | A1 | A1 | A1 | A1 | A1 | A1 | E | A1 | A1 | A1 | A1 | A1 | A1 | A1 | A1 | A1 |
| A1 | A1 | A1 | A1 | A1 | A1 | A1 | A1 | F | A1 | A1 | A1 | A1 | A1 | A1 | A1 | A1 | A1 |
| A1 | A1 | A1 | A1 | A1 | A1 | A1 | A1 | G | A1 | A1 | A1 | A1 | A1 | A1 | A1 | A1 | A1 |
| A1 | A1 | A1 | A1 | A1 | A1 | A1 | A1 | H | A1 | A1 | A1 | A1 | A1 | A1 | A1 | A1 | A1 |
| 15 | | | | | | P | 15 | R | 1 | C | 16 | | | | | | P |

-continued

| BB1 | | | | | | | | | | | | | | | | | |
|---|---|---|---|---|---|---|---|---|---|---|---|---|---|---|---|---|---|
| | | | | | | | | | A | 2 | | | | | | | |
| 4 | 5 | 6 | 7 | 8 | 9 | 10 | 11 | | 2 | 3 | 4 | 5 | 6 | 7 | 8 | 9 | 10 |
| A2 | A2 | A2 | A2 | A2 | A2 | A2 | A2 | A | A2 | A2 | A2 | A2 | A2 | A2 | A2 | A2 | A2 |
| A2 | A2 | A2 | A2 | A2 | A2 | A2 | A2 | B | A2 | A2 | A2 | A2 | A2 | A2 | A2 | A2 | A2 |
| A2 | A2 | A2 | A2 | A2 | A2 | A2 | A2 | C | A2 | A2 | A2 | A2 | A2 | A2 | A2 | A2 | A2 |
| A2 | A2 | A2 | A2 | A2 | A2 | A2 | A2 | D | A2 | A2 | A2 | A2 | A2 | A2 | A2 | A2 | A2 |
| A2 | A2 | A2 | A2 | A2 | A2 | A2 | A2 | E | A2 | A2 | A2 | A2 | A2 | A2 | A2 | A2 | A2 |
| A2 | A2 | A2 | A2 | A2 | A2 | A2 | A2 | F | A2 | A2 | A2 | A2 | A2 | A2 | A2 | A2 | A2 |
| A2 | A2 | A2 | A2 | A2 | A2 | A2 | A2 | G | A2 | A2 | A2 | A2 | A2 | A2 | A2 | A2 | A2 |
| A2 | A2 | A2 | A2 | A2 | A2 | A2 | A2 | H | A2 | A2 | A2 | A2 | A2 | A2 | A2 | A2 | A2 |
| 15 | | | | | | P | 31 | R | 2 | C | 16 | | | | | | P |
| | | | | | | | | | A | 3 | | | | | | | |
| 4 | 5 | 6 | 7 | 8 | 9 | 10 | 11 | | 2 | 3 | 4 | 5 | 6 | 7 | 8 | 9 | 10 |
| A3 | A3 | A3 | A3 | A3 | A3 | A3 | A3 | A | A3 | A3 | A3 | A3 | A3 | A3 | A3 | A3 | A3 |
| A3 | A3 | A3 | A3 | A3 | A3 | A3 | A3 | B | A3 | A3 | A3 | A3 | A3 | A3 | A3 | A3 | A3 |
| A3 | A3 | A3 | A3 | A3 | A3 | A3 | A3 | C | A3 | A3 | A3 | A3 | A3 | A3 | A3 | A3 | A3 |
| A3 | A3 | A3 | A3 | A3 | A3 | A3 | A3 | D | A3 | A3 | A3 | A3 | A3 | A3 | A3 | A3 | A3 |
| A3 | A3 | A3 | A3 | A3 | A3 | A3 | A3 | E | A3 | A3 | A3 | A3 | A3 | A3 | A3 | A3 | A3 |
| A3 | A3 | A3 | A3 | A3 | A3 | A3 | A3 | F | A3 | A3 | A3 | A3 | A3 | A3 | A3 | A3 | A3 |
| A3 | A3 | A3 | A3 | A3 | A3 | A3 | A3 | G | A3 | A3 | A3 | A3 | A3 | A3 | A3 | A3 | A3 |
| A3 | A3 | A3 | A3 | A3 | A3 | A3 | A3 | H | A3 | A3 | A3 | A3 | A3 | A3 | A3 | A3 | A3 |
| 15 | | | | | | P | 47 | R | 3 | C | 16 | | | | | | P |
| | | | | | | | | | A | 4 | | | | | | | |
| 4 | 5 | 6 | 7 | 8 | 9 | 10 | 11 | | 2 | 3 | 4 | 5 | 6 | 7 | 8 | 9 | 10 |
| A4 | A4 | A4 | A4 | A4 | A4 | A4 | A4 | A | A4 | A4 | A4 | A4 | A4 | A4 | A4 | A4 | A4 |
| A4 | A4 | A4 | A4 | A4 | A4 | A4 | A4 | B | A4 | A4 | A4 | A4 | A4 | A4 | A4 | A4 | A4 |
| A4 | A4 | A4 | A4 | A4 | A4 | A4 | A4 | C | A4 | A4 | A4 | A4 | A4 | A4 | A4 | A4 | A4 |
| A4 | A4 | A4 | A4 | A4 | A4 | A4 | A4 | D | A4 | A4 | A4 | A4 | A4 | A4 | A4 | A4 | A4 |
| A4 | A4 | A4 | A4 | A4 | A4 | A4 | A4 | E | A4 | A4 | A4 | A4 | A4 | A4 | A4 | A4 | A4 |
| A4 | A4 | A4 | A4 | A4 | A4 | A4 | A4 | F | A4 | A4 | A4 | A4 | A4 | A4 | A4 | A4 | A4 |
| A4 | A4 | A4 | A4 | A4 | A4 | A4 | A4 | G | A4 | A4 | A4 | A4 | A4 | A4 | A4 | A4 | A4 |
| A4 | A4 | A4 | A4 | A4 | A4 | A4 | A4 | H | A4 | A4 | A4 | A4 | A4 | A4 | A4 | A4 | A4 |
| 15 | | | | | | P | 63 | R | 4 | C | 16 | | | | | | P |
| | | | | | | | | | A | 5 | | | | | | | |
| 4 | 5 | 6 | 7 | 8 | 9 | 10 | 11 | | 2 | 3 | 4 | 5 | 6 | 7 | 8 | 9 | 10 |
| A5 | A5 | A5 | A5 | A5 | A5 | A5 | A5 | A | A5 | A5 | A5 | A5 | A5 | A5 | A5 | A5 | A5 |
| A5 | A5 | A5 | A5 | A5 | A5 | A5 | A5 | B | A5 | A5 | A5 | A5 | A5 | A5 | A5 | A5 | A5 |
| A5 | A5 | A5 | A5 | A5 | A5 | A5 | A5 | C | A5 | A5 | A5 | A5 | A5 | A5 | A5 | A5 | A5 |
| A5 | A5 | A5 | A5 | A5 | A5 | A5 | A5 | D | A5 | A5 | A5 | A5 | A5 | A5 | A5 | A5 | A5 |
| A5 | A5 | A5 | A5 | A5 | A5 | A5 | A5 | E | A5 | A5 | A5 | A5 | A5 | A5 | A5 | A5 | A5 |
| A5 | A5 | A5 | A5 | A5 | A5 | A5 | A5 | F | A5 | A5 | A5 | A5 | A5 | A5 | A5 | A5 | A5 |
| A5 | A5 | A5 | A5 | A5 | A5 | A5 | A5 | G | A5 | A5 | A5 | A5 | A5 | A5 | A5 | A5 | A5 |
| A5 | A5 | A5 | A5 | A5 | A5 | A5 | A5 | H | A5 | A5 | A5 | A5 | A5 | A5 | A5 | A5 | A5 |
| 15 | | | | | | P | 79 | R | 5 | C | 16 | | | | | | P |
| | | | | | | | | | A | 6 | | | | | | | |
| 4 | 5 | 6 | 7 | 8 | 9 | 10 | 11 | | 2 | 3 | 4 | 5 | 6 | 7 | 8 | 9 | 10 |
| A6 | A6 | A6 | A6 | A6 | A6 | A6 | A6 | A | A6 | A6 | A6 | A6 | A6 | A6 | A6 | A6 | A6 |
| A6 | A6 | A6 | A6 | A6 | A6 | A6 | A6 | B | A6 | A6 | A6 | A6 | A6 | A6 | A6 | A6 | A6 |
| A6 | A6 | A6 | A6 | A6 | A6 | A6 | A6 | C | A6 | A6 | A6 | A6 | A6 | A6 | A6 | A6 | A6 |
| A6 | A6 | A6 | A6 | A6 | A6 | A6 | A6 | D | A6 | A6 | A6 | A6 | A6 | A6 | A6 | A6 | A6 |
| A6 | A6 | A6 | A6 | A6 | A6 | A6 | A6 | E | A6 | A6 | A6 | A6 | A6 | A6 | A6 | A6 | A6 |
| A6 | A6 | A6 | A6 | A6 | A6 | A6 | A6 | F | A6 | A6 | A6 | A6 | A6 | A6 | A6 | A6 | A6 |
| A6 | A6 | A6 | A6 | A6 | A6 | A6 | A6 | G | A6 | A6 | A6 | A6 | A6 | A6 | A6 | A6 | A6 |
| A6 | A6 | A6 | A6 | A6 | A6 | A6 | A6 | H | A6 | A6 | A6 | A6 | A6 | A6 | A6 | A6 | A6 |
| 15 | | | | | | P | 95 | R | 6 | C | 16 | | | | | | P |

-continued

BB1

| 4 | 5 | 6 | 7 | 8 | 9 | 10 | 11 | | A<br>2 | 7<br>3 | 4 | 5 | 6 | 7 | 8 | 9 | 10 |
|---|---|---|---|---|---|---|---|---|---|---|---|---|---|---|---|---|---|
| A7 | A7 | A7 | A7 | A7 | A7 | A7 | A7 | A | A7 | A7 | A7 | A7 | A7 | A7 | A7 | A7 | A7 |
| A7 | A7 | A7 | A7 | A7 | A7 | A7 | A7 | B | A7 | A7 | A7 | A7 | A7 | A7 | A7 | A7 | A7 |
| A7 | A7 | A7 | A7 | A7 | A7 | A7 | A7 | C | A7 | A7 | A7 | A7 | A7 | A7 | A7 | A7 | A7 |
| A7 | A7 | A7 | A7 | A7 | A7 | A7 | A7 | D | A7 | A7 | A7 | A7 | A7 | A7 | A7 | A7 | A7 |
| A7 | A7 | A7 | A7 | A7 | A7 | A7 | A7 | E | A7 | A7 | A7 | A7 | A7 | A7 | A7 | A7 | A7 |
| A7 | A7 | A7 | A7 | A7 | A7 | A7 | A7 | F | A7 | A7 | A7 | A7 | A7 | A7 | A7 | A7 | A7 |
| A7 | A7 | A7 | A7 | A7 | A7 | A7 | A7 | G | A7 | A7 | A7 | A7 | A7 | A7 | A7 | A7 | A7 |
| A7 | A7 | A7 | A7 | A7 | A7 | A7 | A7 | H | A7 | A7 | A7 | A7 | A7 | A7 | A7 | A7 | A7 |
| 15 | | | | | | P | 111 | R | 7 | C | 16 | | | | | | P |

| 4 | 5 | 6 | 7 | 8 | 9 | 10 | 11 | | A<br>2 | 8<br>3 | 4 | 5 | 6 | 7 | 8 | 9 | 10 |
|---|---|---|---|---|---|---|---|---|---|---|---|---|---|---|---|---|---|
| A8 | A8 | A8 | A8 | A8 | A8 | A8 | A8 | A | A8 | A8 | A8 | A8 | A8 | A8 | A8 | A8 | A8 |
| A8 | A8 | A8 | A8 | A8 | A8 | A8 | A8 | B | A8 | A8 | A8 | A8 | A8 | A8 | A8 | A8 | A8 |
| A8 | A8 | A8 | A8 | A8 | A8 | A8 | A8 | C | A8 | A8 | A8 | A8 | A8 | A8 | A8 | A8 | A8 |
| A8 | A8 | A8 | A8 | A8 | A8 | A8 | A8 | D | A8 | A8 | A8 | A8 | A8 | A8 | A8 | A8 | A8 |
| A8 | A8 | A8 | A8 | A8 | A8 | A8 | A8 | E | A8 | A8 | A8 | A8 | A8 | A8 | A8 | A8 | A8 |
| A8 | A8 | A8 | A8 | A8 | A8 | A8 | A8 | F | A8 | A8 | A8 | A8 | A8 | A8 | A8 | A8 | A8 |
| A8 | A8 | A8 | A8 | A8 | A8 | A8 | A8 | G | A8 | A8 | A8 | A8 | A8 | A8 | A8 | A8 | A8 |
| A8 | A8 | A8 | A8 | A8 | A8 | A8 | A8 | H | A8 | A8 | A8 | A8 | A8 | A8 | A8 | A8 | A8 |
| 15 | | | | | | P | 127 | R | 8 | C | 16 | | | | | | P |

| 11 |
|---|
| A1 |
| A1 |
| A1 |
| A1 |
| A1 |
| A1 |
| A1 |
| A1 |
| 16 |

| 11 |
|---|
| A2 |
| A2 |
| A2 |
| A2 |
| A2 |
| A2 |
| A2 |
| A2 |
| 32 |

| 11 |
|---|
| A3 |
| A3 |
| A3 |
| A3 |
| A3 |
| A3 |
| A3 |
| A3 |
| 48 |

| 11 |
|---|
| A4 |
| A4 |
| A4 |
| A4 |
| A4 |
| A4 |
| A4 |
| A4 |
| 64 |

-continued

| BB1 |
|---|
| 11 |
| A5 |
| A5 |
| A5 |
| A5 |
| A5 |
| A5 |
| A5 |
| A5 |
| 80 |
| 11 |
| A6 |
| A6 |
| A6 |
| A6 |
| A6 |
| A6 |
| A6 |
| A6 |
| 96 |
| 11 |
| A7 |
| A7 |
| A7 |
| A7 |
| A7 |
| A7 |
| A7 |
| A7 |
| 112 |
| 11 |
| A8 |
| A8 |
| A8 |
| A8 |
| A8 |
| A8 |
| A8 |
| A8 |
| 128 |

BB2

| | B<br>2 | 1<br>3 | 4 | 5 | 6 | B<br>7 | 2<br>8 | 9 | 10 | 11 | | B<br>2 | 3<br>3 | 4 | 5 | 6 | B<br>7 |
|---|---|---|---|---|---|---|---|---|---|---|---|---|---|---|---|---|---|
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 1 | C | 1 | | | | | | P | 1 | R | 1 | C | 2 | | | |

-continued

| BB2 | | | | | | | | | | | | | | | | | |
|---|---|---|---|---|---|---|---|---|---|---|---|---|---|---|---|---|---|
| | B | 1 | | | | B | 2 | | | | | B | 3 | | | | B |
| | 2 | 3 | 4 | 5 | 6 | 7 | 8 | 9 | 10 | 11 | | 2 | 3 | 4 | 5 | 6 | 7 |
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 2 | C | 1 | | | | | | P | 17 | R | 2 | C | 2 | | | |
| | B | 1 | | | | B | 2 | | | | | B | 3 | | | | B |
| | 2 | 3 | 4 | 5 | 6 | 7 | 8 | 9 | 10 | 11 | | 2 | 3 | 4 | 5 | 6 | 7 |
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 3 | C | 1 | | | | | | P | 33 | R | 3 | C | 2 | | | |
| | B | 1 | | | | B | 2 | | | | | B | 3 | | | | B |
| | 2 | 3 | 4 | 5 | 6 | 7 | 8 | 9 | 10 | 11 | | 2 | 3 | 4 | 5 | 6 | 7 |
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 4 | C | 1 | | | | | | P | 49 | R | 4 | C | 2 | | | |
| | B | 1 | | | | B | 2 | | | | | B | 3 | | | | B |
| | 2 | 3 | 4 | 5 | 6 | 7 | 8 | 9 | 10 | 11 | | 2 | 3 | 4 | 5 | 6 | 7 |
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 5 | C | 1 | | | | | | P | 65 | R | 5 | C | 2 | | | |
| | B | 1 | | | | B | 2 | | | | | B | 3 | | | | B |
| | 2 | 3 | 4 | 5 | 6 | 7 | 8 | 9 | 10 | 11 | | 2 | 3 | 4 | 5 | 6 | 7 |
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 6 | C | 1 | | | | | | P | 81 | R | 6 | C | 2 | | | |

-continued

BB2

| | B<br>2 | 1<br>3 | 4 | 5 | 6 | B<br>7 | 2<br>8 | 9 | 10 | 11 | | B<br>2 | 3<br>3 | 4 | 5 | 6 | B<br>7 |
|---|---|---|---|---|---|---|---|---|---|---|---|---|---|---|---|---|---|
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 7 | C | 1 | | | | | | P | 97 | R | 7 | C | 2 | | | |

| | B<br>2 | 1<br>3 | 4 | 5 | 6 | B<br>7 | 2<br>8 | 9 | 10 | 11 | | B<br>2 | 3<br>3 | 4 | 5 | 6 | B<br>7 |
|---|---|---|---|---|---|---|---|---|---|---|---|---|---|---|---|---|---|
| A | B1 | B1 | B1 | B1 | B1 | B2 | B2 | B2 | B2 | B2 | A | B3 | B3 | B3 | B3 | B3 | B4 |
| B | B1 | B1 | B1 | B1 | B1 | B2 | B2 | B2 | B2 | B2 | B | B3 | B3 | B3 | B3 | B3 | B4 |
| C | B1 | B1 | B1 | B1 | B1 | B2 | B2 | B2 | B2 | B2 | C | B3 | B3 | B3 | B3 | B3 | B4 |
| D | B1 | B1 | B1 | B1 | B1 | B2 | B2 | B2 | B2 | B2 | D | B3 | B3 | B3 | B3 | B3 | B4 |
| E | B1 | B1 | B1 | B1 | B1 | B2 | B2 | B2 | B2 | B2 | E | B3 | B3 | B3 | B3 | B3 | B4 |
| F | B1 | B1 | B1 | B1 | B1 | B2 | B2 | B2 | B2 | B2 | F | B3 | B3 | B3 | B3 | B3 | B4 |
| G | B1 | B1 | B1 | B1 | B1 | B2 | B2 | B2 | B2 | B2 | G | B3 | B3 | B3 | B3 | B3 | B4 |
| H | B1 | B1 | B1 | B1 | B1 | B2 | B2 | B2 | B2 | B2 | H | B3 | B3 | B3 | B3 | B3 | B4 |
| R | 8 | C | 1 | | | | | | P | 113 | R | 8 | C | 2 | | | |

| 4<br>8 | 9 | 10 | 11 | | B<br>2 | 5<br>3 | 4 | 5 | 6 | B<br>7 | 6<br>8 | 9 | 10 | 11 | | B<br>2 |
|---|---|---|---|---|---|---|---|---|---|---|---|---|---|---|---|---|
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 2 | R | 1 | C | 3 | | | | | | P | 3 | R | 1 |

| 4<br>8 | 9 | 10 | 11 | | B<br>2 | 5<br>3 | 4 | 5 | 6 | B<br>7 | 6<br>8 | 9 | 10 | 11 | | B<br>2 |
|---|---|---|---|---|---|---|---|---|---|---|---|---|---|---|---|---|
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 18 | R | 2 | C | 3 | | | | | | P | 19 | R | 2 |

| 4<br>8 | 9 | 10 | 11 | | B<br>2 | 5<br>3 | 4 | 5 | 6 | B<br>7 | 6<br>8 | 9 | 10 | 11 | | B<br>2 |
|---|---|---|---|---|---|---|---|---|---|---|---|---|---|---|---|---|
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 34 | R | 3 | C | 3 | | | | | | P | 35 | R | 3 |

-continued

BB2

| 4 | | | | | B | 5 | | | | B | 6 | | | | | B |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 50 | R | 4 | C | 3 | | | | | | P | 51 | R | 4 |

| 4 | | | | | B | 5 | | | | B | 6 | | | | | B |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 66 | R | 5 | C | 3 | | | | | | P | 67 | R | 5 |

| 4 | | | | | B | 5 | | | | B | 6 | | | | | B |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 82 | R | 6 | C | 3 | | | | | | P | 83 | R | 6 |

| 4 | | | | | B | 5 | | | | B | 6 | | | | | B |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 98 | R | 7 | C | 3 | | | | | | P | 99 | R | 7 |

| 4 | | | | | B | 5 | | | | B | 6 | | | | | B |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| B4 | B4 | B4 | B4 | A | B5 | B5 | B5 | B5 | B5 | B6 | B6 | B6 | B6 | B6 | A | B7 |
| B4 | B4 | B4 | B4 | B | B5 | B5 | B5 | B5 | B5 | B6 | B6 | B6 | B6 | B6 | B | B7 |
| B4 | B4 | B4 | B4 | C | B5 | B5 | B5 | B5 | B5 | B6 | B6 | B6 | B6 | B6 | C | B7 |
| B4 | B4 | B4 | B4 | D | B5 | B5 | B5 | B5 | B5 | B6 | B6 | B6 | B6 | B6 | D | B7 |
| B4 | B4 | B4 | B4 | E | B5 | B5 | B5 | B5 | B5 | B6 | B6 | B6 | B6 | B6 | E | B7 |
| B4 | B4 | B4 | B4 | F | B5 | B5 | B5 | B5 | B5 | B6 | B6 | B6 | B6 | B6 | F | B7 |
| B4 | B4 | B4 | B4 | G | B5 | B5 | B5 | B5 | B5 | B6 | B6 | B6 | B6 | B6 | G | B7 |
| B4 | B4 | B4 | B4 | H | B5 | B5 | B5 | B5 | B5 | B6 | B6 | B6 | B6 | B6 | H | B7 |
| | | P | 114 | R | 8 | C | 3 | | | | | | P | 115 | R | 8 |

-continued

| BB2 | | | | | | | | | | | | | | | | | |
|---|---|---|---|---|---|---|---|---|---|---|---|---|---|---|---|---|---|
| 7 | | | | B | 8 | | | | | B | 9 | | | | B | 10 | |
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 4 | R | 1 | C | 5 | | | | | |
| 7 | | | | B | 8 | | | | | B | 9 | | | | B | 10 | |
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 20 | R | 2 | C | 5 | | | | | |
| 7 | | | | B | 8 | | | | | B | 9 | | | | B | 10 | |
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 36 | R | 3 | C | 5 | | | | | |
| 7 | | | | B | 8 | | | | | B | 9 | | | | B | 10 | |
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 52 | R | 4 | C | 5 | | | | | |
| 7 | | | | B | 8 | | | | | B | 9 | | | | B | 10 | |
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 68 | R | 5 | C | 5 | | | | | |

-continued

BB2

| 7 | | | | B | 8 | | | | | B | 9 | | | | B | 10 | |
|---|---|---|---|---|---|---|---|---|---|---|---|---|---|---|---|---|---|
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 84 | R | 6 | C | 5 | | | | | |

| 7 | | | | B | 8 | | | | | B | 9 | | | | B | 10 | |
|---|---|---|---|---|---|---|---|---|---|---|---|---|---|---|---|---|---|
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 100 | R | 7 | C | 5 | | | | | |

| 7 | | | | B | 8 | | | | | B | 9 | | | | B | 10 | |
|---|---|---|---|---|---|---|---|---|---|---|---|---|---|---|---|---|---|
| 3 | 4 | 5 | 6 | 7 | 8 | 9 | 10 | 11 | | 2 | 3 | 4 | 5 | 6 | 7 | 8 | 9 |
| B7 | B7 | B7 | B7 | B8 | B8 | B8 | B8 | B8 | A | B9 | B9 | B9 | B9 | B9 | B10 | B10 | B10 |
| B7 | B7 | B7 | B7 | B8 | B8 | B8 | B8 | B8 | B | B9 | B9 | B9 | B9 | B9 | B10 | B10 | B10 |
| B7 | B7 | B7 | B7 | B8 | B8 | B8 | B8 | B8 | C | B9 | B9 | B9 | B9 | B9 | B10 | B10 | B10 |
| B7 | B7 | B7 | B7 | B8 | B8 | B8 | B8 | B8 | D | B9 | B9 | B9 | B9 | B9 | B10 | B10 | B10 |
| B7 | B7 | B7 | B7 | B8 | B8 | B8 | B8 | B8 | E | B9 | B9 | B9 | B9 | B9 | B10 | B10 | B10 |
| B7 | B7 | B7 | B7 | B8 | B8 | B8 | B8 | B8 | F | B9 | B9 | B9 | B9 | B9 | B10 | B10 | B10 |
| B7 | B7 | B7 | B7 | B8 | B8 | B8 | B8 | B8 | G | B9 | B9 | B9 | B9 | B9 | B10 | B10 | B10 |
| B7 | B7 | B7 | B7 | B8 | B8 | B8 | B8 | B8 | H | B9 | B9 | B9 | B9 | B9 | B10 | B10 | B10 |
| C | 4 | | | | | | P | 116 | R | 8 | C | 5 | | | | | |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 5 | R | 1 | C | 6 | | | | | | P | 6 | R | 1 | C | 7 |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 21 | R | 2 | C | 6 | | | | | | P | 22 | R | 2 | C | 7 |

-continued

BB2

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 37 | R | 3 | C | 6 | | | | | | P | 38 | R | 3 | C | 7 |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 53 | R | 4 | C | 6 | | | | | | P | 54 | R | 4 | C | 7 |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 69 | R | 5 | C | 6 | | | | | | P | 70 | R | 5 | C | 7 |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 85 | R | 6 | C | 6 | | | | | | P | 86 | R | 6 | C | 7 |

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 101 | R | 7 | C | 6 | | | | | | P | 102 | R | 7 | C | 7 |

-continued

BB2

| | | | B | 11 | | | | B | 12 | | | | | B | 13 | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| B10 | B10 | A | B11 | B11 | B11 | B11 | B11 | B12 | B12 | B12 | B12 | B12 | A | B13 | B13 | B13 |
| B10 | B10 | B | B11 | B11 | B11 | B11 | B11 | B12 | B12 | B12 | B12 | B12 | B | B13 | B13 | B13 |
| B10 | B10 | C | B11 | B11 | B11 | B11 | B11 | B12 | B12 | B12 | B12 | B12 | C | B13 | B13 | B13 |
| B10 | B10 | D | B11 | B11 | B11 | B11 | B11 | B12 | B12 | B12 | B12 | B12 | D | B13 | B13 | B13 |
| B10 | B10 | E | B11 | B11 | B11 | B11 | B11 | B12 | B12 | B12 | B12 | B12 | E | B13 | B13 | B13 |
| B10 | B10 | F | B11 | B11 | B11 | B11 | B11 | B12 | B12 | B12 | B12 | B12 | F | B13 | B13 | B13 |
| B10 | B10 | G | B11 | B11 | B11 | B11 | B11 | B12 | B12 | B12 | B12 | B12 | G | B13 | B13 | B13 |
| B10 | B10 | H | B11 | B11 | B11 | B11 | B11 | B12 | B12 | B12 | B12 | B12 | H | B13 | B13 | B13 |
| P | 117 | R | 8 | C | 6 | | | | | | P | 118 | R | 8 | C | 7 |

| | | B | 14 | | | | | B | 15 | | | | B | 16 | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 7 | R | 1 | C | 8 | | | | | | P | 8 |

| | | B | 14 | | | | | B | 15 | | | | B | 16 | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 23 | R | 2 | C | 8 | | | | | | P | 24 |

| | | B | 14 | | | | | B | 15 | | | | B | 16 | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 39 | R | 3 | C | 8 | | | | | | P | 40 |

| | | B | 14 | | | | | B | 15 | | | | B | 16 | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 55 | R | 4 | C | 8 | | | | | | P | 56 |

-continued

BB2

| | | B | 14 | | | | | B | 15 | | | | B | 16 | | | |
|---|---|---|---|---|---|---|---|---|---|---|---|---|---|---|---|---|---|
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 71 | R | 5 | C | 8 | | | | | | P | 72 |
| | | B | 14 | | | | | B | 15 | | | | B | 16 | | | |
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 87 | R | 6 | C | 8 | | | | | | P | 68 |
| | | B | 14 | | | | | B | 15 | | | | B | 16 | | | |
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 103 | R | 7 | C | 8 | | | | | | P | 104 |
| | | B | 14 | | | | | B | 15 | | | | B | 16 | | | |
| 5 | 6 | 7 | 8 | 9 | 10 | 11 | | 2 | 3 | 4 | 5 | 6 | 7 | 8 | 9 | 10 | 11 |
| B13 | B13 | B14 | B14 | B14 | B14 | B14 | A | B15 | B15 | B15 | B15 | B15 | B16 | B16 | B16 | B16 | B16 |
| B13 | B13 | B14 | B14 | B14 | B14 | B14 | B | B15 | B15 | B15 | B15 | B15 | B16 | B16 | B16 | B16 | B16 |
| B13 | B13 | B14 | B14 | B14 | B14 | B14 | C | B15 | B15 | B15 | B15 | B15 | B16 | B16 | B16 | B16 | B16 |
| B13 | B13 | B14 | B14 | B14 | B14 | B14 | D | B15 | B15 | B15 | B15 | B15 | B16 | B16 | B16 | B16 | B16 |
| B13 | B13 | B14 | B14 | B14 | B14 | B14 | E | B15 | B15 | B15 | B15 | B15 | B16 | B16 | B16 | B16 | B16 |
| B13 | B13 | B14 | B14 | B14 | B14 | B14 | F | B15 | B15 | B15 | B15 | B15 | B16 | B16 | B16 | B16 | B16 |
| B13 | B13 | B14 | B14 | B14 | B14 | B14 | G | B15 | B15 | B15 | B15 | B15 | B16 | B16 | B16 | B16 | B16 |
| B13 | B13 | B14 | B14 | B14 | B14 | B14 | H | B15 | B15 | B15 | B15 | B15 | B16 | B16 | B16 | B16 | B16 |
| | | | | | P | 119 | R | 8 | C | 8 | | | | | | P | 120 |

| | B | 17 | | | | B | 18 | | | | | B | 19 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 1 | C | 9 | | | | | | P | 9 | R | 1 | C | 10 | | |

-continued

| BB2 | | | | | | | | | | | | | | | | |
|---|---|---|---|---|---|---|---|---|---|---|---|---|---|---|---|---|
| | B | 17 | | | | B | 18 | | | | | B | 19 | | | |
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 2 | C | 9 | | | | | | P | 25 | R | 2 | C | 10 | | |
| | B | 17 | | | | B | 18 | | | | | B | 19 | | | |
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 3 | C | 9 | | | | | | P | 41 | R | 3 | C | 10 | | |
| | B | 17 | | | | B | 18 | | | | | B | 19 | | | |
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 4 | C | 9 | | | | | | P | 57 | R | 4 | C | 10 | | |
| | B | 17 | | | | B | 18 | | | | | B | 19 | | | |
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 5 | C | 9 | | | | | | P | 73 | R | 5 | C | 10 | | |
| | B | 17 | | | | B | 18 | | | | | B | 19 | | | |
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 6 | C | 9 | | | | | | P | 89 | R | 6 | C | 10 | | |

-continued

BB2

| | B | 17 | | | | B | 18 | | | | | B | 19 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 7 | C | 9 | | | | | | P | 105 | R | 7 | C | 10 | | |

| | B | 17 | | | | B | 18 | | | | | B | 19 | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | B17 | B17 | B17 | B17 | B17 | B18 | B18 | B18 | B18 | B18 | A | B19 | B19 | B19 | B19 | B19 |
| B | B17 | B17 | B17 | B17 | B17 | B18 | B18 | B18 | B18 | B18 | B | B19 | B19 | B19 | B19 | B19 |
| C | B17 | B17 | B17 | B17 | B17 | B18 | B18 | B18 | B18 | B18 | C | B19 | B19 | B19 | B19 | B19 |
| D | B17 | B17 | B17 | B17 | B17 | B18 | B18 | B18 | B18 | B18 | D | B19 | B19 | B19 | B19 | B19 |
| E | B17 | B17 | B17 | B17 | B17 | B18 | B18 | B18 | B18 | B18 | E | B19 | B19 | B19 | B19 | B19 |
| F | B17 | B17 | B17 | B17 | B17 | B18 | B18 | B18 | B18 | B18 | F | B19 | B19 | B19 | B19 | B19 |
| G | B17 | B17 | B17 | B17 | B17 | B18 | B18 | B18 | B18 | B18 | G | B19 | B19 | B19 | B19 | B19 |
| H | B17 | B17 | B17 | B17 | B17 | B18 | B18 | B18 | B18 | B18 | H | B19 | B19 | B19 | B19 | B19 |
| R | 8 | C | 9 | | | | | | P | 121 | R | 8 | C | 10 | | |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 10 | R | 1 | C | 11 | | | | | | P | 11 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 26 | R | 2 | C | 11 | | | | | | P | 27 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 42 | R | 3 | C | 11 | | | | | | P | 43 | R |

-continued

BB2

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 58 | R | 4 | C | 11 | | | | | | P | 59 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 74 | R | 5 | C | 11 | | | | | | P | 75 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 90 | R | 6 | C | 11 | | | | | | P | 91 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 106 | R | 7 | C | 11 | | | | | | P | 107 | R |

| B | 20 | | | | | B | 21 | | | | B | 22 | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| B20 | B20 | B20 | B20 | B20 | A | B21 | B21 | B21 | B21 | B21 | B22 | B22 | B22 | B22 | B22 | A |
| B20 | B20 | B20 | B20 | B20 | B | B21 | B21 | B21 | B21 | B21 | B22 | B22 | B22 | B22 | B22 | B |
| B20 | B20 | B20 | B20 | B20 | C | B21 | B21 | B21 | B21 | B21 | B22 | B22 | B22 | B22 | B22 | C |
| B20 | B20 | B20 | B20 | B20 | D | B21 | B21 | B21 | B21 | B21 | B22 | B22 | B22 | B22 | B22 | D |
| B20 | B20 | B20 | B20 | B20 | E | B21 | B21 | B21 | B21 | B21 | B22 | B22 | B22 | B22 | B22 | E |
| B20 | B20 | B20 | B20 | B20 | F | B21 | B21 | B21 | B21 | B21 | B22 | B22 | B22 | B22 | B22 | F |
| B20 | B20 | B20 | B20 | B20 | G | B21 | B21 | B21 | B21 | B21 | B22 | B22 | B22 | B22 | B22 | G |
| B20 | B20 | B20 | B20 | B20 | H | B21 | B21 | B21 | B21 | B21 | B22 | B22 | B22 | B22 | B22 | H |
| | | | P | 122 | R | 8 | C | 11 | | | | | | P | 123 | R |

-continued

BB2

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 1 | C | 12 | | | | | | P | 12 | R | 1 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 2 | C | 12 | | | | | | P | 28 | R | 2 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 3 | C | 12 | | | | | | P | 44 | R | 3 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 4 | C | 12 | | | | | | P | 60 | R | 4 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 5 | C | 12 | | | | | | P | 76 | R | 5 | C | 13 | | | | |

-continued

BB2

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 6 | C | 12 | | | | | | P | 92 | R | 6 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 7 | C | 12 | | | | | | P | 108 | R | 7 | C | 13 | | | | |

| B | 23 | | | | B | 24 | | | | | B | 25 | | | | B | 26 |
|---|---|---|---|---|---|---|---|---|---|---|---|---|---|---|---|---|---|
| 2 | 3 | 4 | 5 | 6 | 7 | 8 | 9 | 10 | 11 | | 2 | 3 | 4 | 5 | 6 | 7 | 8 |
| B23 | B23 | B23 | B23 | B23 | B24 | B24 | B24 | B24 | B24 | A | B25 | B25 | B25 | B25 | B25 | B26 | B26 |
| B23 | B23 | B23 | B23 | B23 | B24 | B24 | B24 | B24 | B24 | B | B25 | B25 | B25 | B25 | B25 | B26 | B26 |
| B23 | B23 | B23 | B23 | B23 | B24 | B24 | B24 | B24 | B24 | C | B25 | B25 | B25 | B25 | B25 | B26 | B26 |
| B23 | B23 | B23 | B23 | B23 | B24 | B24 | B24 | B24 | B24 | D | B25 | B25 | B25 | B25 | B25 | B26 | B26 |
| B23 | B23 | B23 | B23 | B23 | B24 | B24 | B24 | B24 | B24 | E | B25 | B25 | B25 | B25 | B25 | B26 | B26 |
| B23 | B23 | B23 | B23 | B23 | B24 | B24 | B24 | B24 | B24 | F | B25 | B25 | B25 | B25 | B25 | B26 | B26 |
| B23 | B23 | B23 | B23 | B23 | B24 | B24 | B24 | B24 | B24 | G | B25 | B25 | B25 | B25 | B25 | B26 | B26 |
| B23 | B23 | B23 | B23 | B23 | B24 | B24 | B24 | B24 | B24 | H | B25 | B25 | B25 | B25 | B25 | B26 | B26 |
| 8 | C | 12 | | | | | | P | 124 | R | 6 | C | 13 | | | | |

| | | | | B | 27 | | | | B | 8 | | | | | B | 29 |
|---|---|---|---|---|---|---|---|---|---|---|---|---|---|---|---|---|
| 9 | 10 | 11 | | 2 | 3 | 4 | 5 | 6 | 7 | 8 | 9 | 10 | 11 | | 2 | 3 |
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 13 | R | 1 | C | 14 | | | | | | P | 14 | R | 1 | C |

| | | | | B | 27 | | | | B | 28 | | | | | B | 29 |
|---|---|---|---|---|---|---|---|---|---|---|---|---|---|---|---|---|
| 9 | 10 | 11 | | 2 | 3 | 4 | 5 | 6 | 7 | 8 | 9 | 10 | 11 | | 2 | 3 |
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 29 | R | 2 | C | 14 | | | | | | P | 30 | R | 2 | C |

-continued

BB2

| 9 | 10 | 11 | | B 2 | 27 3 | 4 | 5 | 6 | B 7 | 28 8 | 9 | 10 | 11 | | B 2 | 29 3 |
|---|---|---|---|---|---|---|---|---|---|---|---|---|---|---|---|---|
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 45 | R | 3 | C | 14 | | | | | | P | 46 | R | 3 | C |

| 9 | 10 | 11 | | B 2 | 27 3 | 4 | 5 | 6 | B 7 | 28 8 | 9 | 10 | 11 | | B 2 | 29 3 |
|---|---|---|---|---|---|---|---|---|---|---|---|---|---|---|---|---|
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 61 | R | 4 | C | 14 | | | | | | P | 62 | R | 4 | C |

| 9 | 10 | 11 | | B 2 | 27 3 | 4 | 5 | 6 | B 7 | 28 8 | 9 | 10 | 11 | | B 2 | 29 3 |
|---|---|---|---|---|---|---|---|---|---|---|---|---|---|---|---|---|
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 77 | R | 5 | C | 14 | | | | | | P | 78 | R | 5 | C |

| 9 | 10 | 11 | | B 2 | 27 3 | 4 | 5 | 6 | B 7 | 28 8 | 9 | 10 | 11 | | B 2 | 29 3 |
|---|---|---|---|---|---|---|---|---|---|---|---|---|---|---|---|---|
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 93 | R | 6 | C | 14 | | | | | | P | 94 | R | 6 | C |

| 9 | 10 | 11 | | B 2 | 27 3 | 4 | 5 | 6 | B 7 | 28 8 | 9 | 10 | 11 | | B 2 | 29 3 |
|---|---|---|---|---|---|---|---|---|---|---|---|---|---|---|---|---|
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 109 | R | 7 | C | 14 | | | | | | P | 110 | R | 7 | C |

-continued

BB2

| | | | | B | 27 | | | | B | 28 | | | | | B | 29 |
|---|---|---|---|---|---|---|---|---|---|---|---|---|---|---|---|---|
| 9 | 10 | 11 | | 2 | 3 | 4 | 5 | 6 | 7 | 8 | 9 | 10 | 11 | | 2 | 3 |
| B26 | B26 | B26 | A | B27 | B27 | B27 | B27 | B27 | B28 | B28 | B28 | B28 | B28 | A | B29 | B29 |
| B26 | B26 | B26 | B | B27 | B27 | B27 | B27 | B27 | B28 | B28 | B28 | B28 | B28 | B | B29 | B29 |
| B26 | B26 | B26 | C | B27 | B27 | B27 | B27 | B27 | B28 | B28 | B28 | B28 | B28 | C | B29 | B29 |
| B26 | B26 | B26 | D | B27 | B27 | B27 | B27 | B27 | B28 | B28 | B28 | B28 | B28 | D | B29 | B29 |
| B26 | B26 | B26 | E | B27 | B27 | B27 | B27 | B27 | B28 | B28 | B28 | B28 | B28 | E | B29 | B29 |
| B26 | B26 | B26 | F | B27 | B27 | B27 | B27 | B27 | B28 | B28 | B28 | B28 | B28 | F | B29 | B29 |
| B26 | B26 | B26 | G | B27 | B27 | B27 | B27 | B27 | B28 | B28 | B28 | B28 | B28 | G | B29 | B29 |
| B26 | B26 | B26 | H | B27 | B27 | B27 | B27 | B27 | B28 | B28 | B28 | B28 | B28 | H | B29 | B29 |
| | P | 125 | R | 8 | C | 14 | | | | | | P | 126 | R | 8 | C |

| | | | B | 30 | | | | | B | 31 | | | | B | 32 | | | |
|---|---|---|---|---|---|---|---|---|---|---|---|---|---|---|---|---|---|---|
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 15 | R | 1 | C | 16 | | | | | | P | 16 |

| | | | B | 30 | | | | | B | 31 | | | | B | 32 | | | |
|---|---|---|---|---|---|---|---|---|---|---|---|---|---|---|---|---|---|---|
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 31 | R | 2 | C | 16 | | | | | | P | 32 |

| | | | B | 30 | | | | | B | 31 | | | | B | 32 | | | |
|---|---|---|---|---|---|---|---|---|---|---|---|---|---|---|---|---|---|---|
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 47 | R | 3 | C | 16 | | | | | | P | 48 |

| | | | B | 30 | | | | | B | 31 | | | | B | 32 | | | |
|---|---|---|---|---|---|---|---|---|---|---|---|---|---|---|---|---|---|---|
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 63 | R | 4 | C | 16 | | | | | | P | 64 |

-continued

| BB2 | | | | | | | | | | | | | | | | | | |
|---|---|---|---|---|---|---|---|---|---|---|---|---|---|---|---|---|---|---|
| | | | B | 30 | | | | | B | 31 | | | | B | 32 | | | |
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 79 | R | 5 | C | 16 | | | | | | P | 80 |
| | | | B | 30 | | | | | B | 31 | | | | B | 32 | | | |
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 95 | R | 6 | C | 16 | | | | | | P | 96 |
| | | | B | 30 | | | | | B | 31 | | | | B | 32 | | | |
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 111 | R | 7 | C | 16 | | | | | | P | 112 |
| | | | B | 30 | | | | | B | 31 | | | | B | 32 | | | |
| 4 | 5 | 6 | 7 | 8 | 9 | 10 | 11 | | 2 | 3 | 4 | 5 | 6 | 7 | 8 | 9 | 10 | 11 |
| B29 | B29 | B29 | B30 | B30 | B30 | B30 | B30 | A | B31 | B31 | B31 | B31 | B31 | B32 | B32 | B32 | B32 | B32 |
| B29 | B29 | B29 | B30 | B30 | B30 | B30 | B30 | B | B31 | B31 | B31 | B31 | B31 | B32 | B32 | B32 | B32 | B32 |
| B29 | B29 | B29 | B30 | B30 | B30 | B30 | B30 | C | B31 | B31 | B31 | B31 | B31 | B32 | B32 | B32 | B32 | B32 |
| B29 | B29 | B29 | B30 | B30 | B30 | B30 | B30 | D | B31 | B31 | B31 | B31 | B31 | B32 | B32 | B32 | B32 | B32 |
| B29 | B29 | B29 | B30 | B30 | B30 | B30 | B30 | E | B31 | B31 | B31 | B31 | B31 | B32 | B32 | B32 | B32 | B32 |
| B29 | B29 | B29 | B30 | B30 | B30 | B30 | B30 | F | B31 | B31 | B31 | B31 | B31 | B32 | B32 | B32 | B32 | B32 |
| B29 | B29 | B29 | B30 | B30 | B30 | B30 | B30 | G | B31 | B31 | B31 | B31 | B31 | B32 | B32 | B32 | B32 | B32 |
| B29 | B29 | B29 | B30 | B30 | B30 | B30 | B30 | H | B31 | B31 | B31 | B31 | B31 | B32 | B32 | B32 | B32 | B32 |
| 15 | | | | | | P | 127 | R | 8 | C | 16 | | | | | | P | 128 |

| BB3 | | | | | | | | | | | | | | | | | |
|---|---|---|---|---|---|---|---|---|---|---|---|---|---|---|---|---|---|
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 1 | C | 1 | | | | | | P | 1 | R | 1 | C | 2 | | | |

-continued

| BB3 | | | | | | | | | | | | | | | | | |
|---|---|---|---|---|---|---|---|---|---|---|---|---|---|---|---|---|---|
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 2 | C | 1 | | | | | | P | 17 | R | 2 | C | 2 | | | |
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 3 | C | 1 | | | | | | P | 33 | R | 3 | C | 2 | | | |
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 4 | C | 1 | | | | | | P | 49 | R | 4 | C | 2 | | | |
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 5 | C | 1 | | | | | | P | 65 | R | 5 | C | 2 | | | |
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 6 | C | 1 | | | | | | P | 81 | R | 6 | C | 2 | | | |
| | C1-40 | | | | | C1-40 | | | | | | C1-40 | | | | | C1-4 |
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 7 | C | 1 | | | | | | P | 97 | R | 7 | C | 2 | | | |

-continued

BB3

| | C1-40 | | | | | C1-40 | | | | | | C1-40 | | | | | C1-4 |
|---|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 | 7 |
| A | C1 | C9 | C17 | C25 | C33 | C1 | C9 | C17 | C25 | C33 | A | C1 | C9 | C17 | C25 | C33 | C1 |
| B | C2 | C10 | C18 | C26 | C34 | C2 | C10 | C18 | C26 | C34 | B | C2 | C10 | C18 | C26 | C34 | C2 |
| C | C3 | C11 | C19 | C27 | C35 | C3 | C11 | C19 | C27 | C35 | C | C3 | C11 | C19 | C27 | C35 | C3 |
| D | C4 | C12 | C20 | C28 | C36 | C4 | C12 | C20 | C28 | C36 | D | C4 | C12 | C20 | C28 | C36 | C4 |
| E | C5 | C13 | C21 | C29 | C37 | C5 | C13 | C21 | C29 | C37 | E | C5 | C13 | C21 | C29 | C37 | C5 |
| F | C6 | C14 | C22 | C30 | C38 | C6 | C14 | C22 | C30 | C38 | F | C6 | C14 | C22 | C30 | C38 | C6 |
| G | C7 | C15 | C23 | C31 | C39 | C7 | C15 | C23 | C31 | C39 | G | C7 | C15 | C23 | C31 | C39 | C7 |
| H | C8 | C16 | C24 | C32 | C40 | C8 | C16 | C24 | C32 | C40 | H | C8 | C16 | C24 | C32 | C40 | C8 |
| R | 8 | C | 1 | | | | | | P | 113 | R | 8 | C | 2 | | | |

| | | | | | C1-40 | | | | | C1-40 | | | | | | C1-4 |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| C9 | C17 | C25 | C33 | A | C1 | C9 | C17 | C25 | C33 | C1 | C9 | C17 | C25 | C33 | A | C1 |
| C10 | C18 | C26 | C34 | B | C2 | C10 | C18 | C26 | C34 | C2 | C10 | C18 | C26 | C34 | B | C2 |
| C11 | C19 | C27 | C35 | C | C3 | C11 | C19 | C27 | C35 | C3 | C11 | C19 | C27 | C35 | C | C3 |
| C12 | C20 | C28 | C36 | D | C4 | C12 | C20 | C28 | C36 | C4 | C12 | C20 | C28 | C36 | D | C4 |
| C13 | C21 | C29 | C37 | E | C5 | C13 | C21 | C29 | C37 | C5 | C13 | C21 | C29 | C37 | E | C5 |
| C14 | C22 | C30 | C38 | F | C6 | C14 | C22 | C30 | C38 | C6 | C22 | C22 | C30 | C38 | F | C6 |
| C15 | C23 | C31 | C39 | G | C7 | C15 | C23 | C31 | C39 | C7 | C15 | C23 | C31 | C39 | G | C7 |
| C16 | C24 | C32 | C40 | H | C8 | C16 | C24 | C32 | C40 | C8 | C16 | C24 | C32 | C40 | H | C8 |
| | | P | 2 | R | 1 | C | 3 | | | | | | P | 3 | R | 1 |

| | | | | | C1-40 | | | | | C1-40 | | | | | | C1-4 |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| C9 | C17 | C25 | C33 | A | C1 | C9 | C17 | C25 | C33 | C1 | C9 | C17 | C25 | C33 | A | C1 |
| C10 | C18 | C26 | C34 | B | C2 | C10 | C18 | C26 | C34 | C2 | C10 | C18 | C26 | C34 | B | C2 |
| C11 | C19 | C27 | C35 | C | C3 | C11 | C19 | C27 | C35 | C3 | C11 | C19 | C27 | C35 | C | C3 |
| C12 | C20 | C28 | C36 | D | C4 | C12 | C20 | C28 | C36 | C4 | C12 | C20 | C28 | C36 | D | C4 |
| C13 | C21 | C29 | C37 | E | C5 | C13 | C21 | C29 | C37 | C5 | C13 | C21 | C29 | C37 | E | C5 |
| C14 | C22 | C30 | C38 | F | C6 | C14 | C22 | C30 | C38 | C6 | C22 | C22 | C30 | C38 | F | C6 |
| C15 | C23 | C31 | C39 | G | C7 | C15 | C23 | C31 | C39 | C7 | C15 | C23 | C31 | C39 | G | C7 |
| C16 | C24 | C32 | C40 | H | C8 | C16 | C24 | C32 | C40 | C8 | C16 | C24 | C32 | C40 | H | C8 |
| | | P | 18 | R | 2 | C | 3 | | | | | | P | 19 | R | 2 |

| | | | | | C1-40 | | | | | C1-40 | | | | | | C1-4 |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| C9 | C17 | C25 | C33 | A | C1 | C9 | C17 | C25 | C33 | C1 | C9 | C17 | C25 | C33 | A | C1 |
| C10 | C18 | C26 | C34 | B | C2 | C10 | C18 | C26 | C34 | C2 | C10 | C18 | C26 | C34 | B | C2 |
| C11 | C19 | C27 | C35 | C | C3 | C11 | C19 | C27 | C35 | C3 | C11 | C19 | C27 | C35 | C | C3 |
| C12 | C20 | C28 | C36 | D | C4 | C12 | C20 | C28 | C36 | C4 | C12 | C20 | C28 | C36 | D | C4 |
| C13 | C21 | C29 | C37 | E | C5 | C13 | C21 | C29 | C37 | C5 | C13 | C21 | C29 | C37 | E | C5 |
| C14 | C22 | C30 | C38 | F | C6 | C14 | C22 | C30 | C38 | C6 | C22 | C22 | C30 | C38 | F | C6 |
| C15 | C23 | C31 | C39 | G | C7 | C15 | C23 | C31 | C39 | C7 | C15 | C23 | C31 | C39 | G | C7 |
| C16 | C24 | C32 | C40 | H | C8 | C16 | C24 | C32 | C40 | C8 | C16 | C24 | C32 | C40 | H | C8 |
| | | P | 34 | R | 3 | C | 3 | | | | | | P | 35 | R | 3 |

| | | | | | C1-40 | | | | | C1-40 | | | | | | C1-4 |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| C9 | C17 | C25 | C33 | A | C1 | C9 | C17 | C25 | C33 | C1 | C9 | C17 | C25 | C33 | A | C1 |
| C10 | C18 | C26 | C34 | B | C2 | C10 | C18 | C26 | C34 | C2 | C10 | C18 | C26 | C34 | B | C2 |
| C11 | C19 | C27 | C35 | C | C3 | C11 | C19 | C27 | C35 | C3 | C11 | C19 | C27 | C35 | C | C3 |
| C12 | C20 | C28 | C36 | D | C4 | C12 | C20 | C28 | C36 | C4 | C12 | C20 | C28 | C36 | D | C4 |
| C13 | C21 | C29 | C37 | E | C5 | C13 | C21 | C29 | C37 | C5 | C13 | C21 | C29 | C37 | E | C5 |
| C14 | C22 | C30 | C38 | F | C6 | C14 | C22 | C30 | C38 | C6 | C22 | C22 | C30 | C38 | F | C6 |
| C15 | C23 | C31 | C39 | G | C7 | C15 | C23 | C31 | C39 | C7 | C15 | C23 | C31 | C39 | G | C7 |
| C16 | C24 | C32 | C40 | H | C8 | C16 | C24 | C32 | C40 | C8 | C16 | C24 | C32 | C40 | H | C8 |
| | | P | 50 | R | 4 | C | 3 | | | | | | P | 51 | R | 4 |

| | | | | | C1-40 | | | | | C1-40 | | | | | | C1-4 |
|---|---|---|---|---|---|---|---|---|---|---|---|---|---|---|---|---|
| 8 | 9 | 10 | 11 | | 2 | 3 | 4 | 5 | 6 | 7 | 8 | 9 | 10 | 11 | | 2 |
| C9 | C17 | C25 | C33 | A | C1 | C9 | C17 | C25 | C33 | C1 | C9 | C17 | C25 | C33 | A | C1 |
| C10 | C18 | C26 | C34 | B | C2 | C10 | C18 | C26 | C34 | C2 | C10 | C18 | C26 | C34 | B | C2 |
| C11 | C19 | C27 | C35 | C | C3 | C11 | C19 | C27 | C35 | C3 | C11 | C19 | C27 | C35 | C | C3 |
| C12 | C20 | C28 | C36 | D | C4 | C12 | C20 | C28 | C36 | C4 | C12 | C20 | C28 | C36 | D | C4 |
| C13 | C21 | C29 | C37 | E | C5 | C13 | C21 | C29 | C37 | C5 | C13 | C21 | C29 | C37 | E | C5 |
| C14 | C22 | C30 | C38 | F | C6 | C14 | C22 | C30 | C38 | C6 | C22 | C22 | C30 | C38 | F | C6 |
| C15 | C23 | C31 | C39 | G | C7 | C15 | C23 | C31 | C39 | C7 | C15 | C23 | C31 | C39 | G | C7 |
| C16 | C24 | C32 | C40 | H | C8 | C16 | C24 | C32 | C40 | C8 | C16 | C24 | C32 | C40 | H | C8 |
| | | P | 66 | R | 5 | C | 3 | | | | | | P | 67 | R | 5 |

-continued

| BB3 | | | | | | | | | | | | | | | | | |
|---|---|---|---|---|---|---|---|---|---|---|---|---|---|---|---|---|---|
| | | | | | C1-40 | | | | | C1-40 | | | | | C1-4 | | |
| 8 | 9 | 10 | 11 | | 2 | 3 | 4 | 5 | 6 | 7 | 8 | 9 | 10 | 11 | | 2 | |
| C9 | C17 | C25 | C33 | A | C1 | C9 | C17 | C25 | C33 | C1 | C9 | C17 | C25 | C33 | A | C1 | |
| C10 | C18 | C26 | C34 | B | C2 | C10 | C18 | C26 | C34 | C2 | C10 | C18 | C26 | C34 | B | C2 | |
| C11 | C19 | C27 | C35 | C | C3 | C11 | C19 | C27 | C35 | C3 | C11 | C19 | C27 | C35 | C | C3 | |
| C12 | C20 | C28 | C36 | D | C4 | C12 | C20 | C28 | C36 | C4 | C12 | C20 | C28 | C36 | D | C4 | |
| C13 | C21 | C29 | C37 | E | C5 | C13 | C21 | C29 | C37 | C5 | C13 | C21 | C29 | C37 | E | C5 | |
| C14 | C22 | C30 | C38 | F | C6 | C14 | C22 | C30 | C38 | C6 | C22 | C22 | C30 | C38 | F | C6 | |
| C15 | C23 | C31 | C39 | G | C7 | C15 | C23 | C31 | C39 | C7 | C15 | C23 | C31 | C39 | G | C7 | |
| C16 | C24 | C32 | C40 | H | C8 | C16 | C24 | C32 | C40 | C8 | C16 | C24 | C32 | C40 | H | C8 | |
| | | P | 82 | R | 6 | C | 3 | | | | | | P | 83 | R | 6 | |
| | | | | | C1-40 | | | | | C1-40 | | | | | C1-4 | | |
| 8 | 9 | 10 | 11 | | 2 | 3 | 4 | 5 | 6 | 7 | 8 | 9 | 10 | 11 | | 2 | |
| C9 | C17 | C25 | C33 | A | C1 | C9 | C17 | C25 | C33 | C1 | C9 | C17 | C25 | C33 | A | C1 | |
| C10 | C18 | C26 | C34 | B | C2 | C10 | C18 | C26 | C34 | C2 | C10 | C18 | C26 | C34 | B | C2 | |
| C11 | C19 | C27 | C35 | C | C3 | C11 | C19 | C27 | C35 | C3 | C11 | C19 | C27 | C35 | C | C3 | |
| C12 | C20 | C28 | C36 | D | C4 | C12 | C20 | C28 | C36 | C4 | C12 | C20 | C28 | C36 | D | C4 | |
| C13 | C21 | C29 | C37 | E | C5 | C13 | C21 | C29 | C37 | C5 | C13 | C21 | C29 | C37 | E | C5 | |
| C14 | C22 | C30 | C38 | F | C6 | C14 | C22 | C30 | C38 | C6 | C22 | C22 | C30 | C38 | F | C6 | |
| C15 | C23 | C31 | C39 | G | C7 | C15 | C23 | C31 | C39 | C7 | C15 | C23 | C31 | C39 | G | C7 | |
| C16 | C24 | C32 | C40 | H | C8 | C16 | C24 | C32 | C40 | C8 | C16 | C24 | C32 | C40 | H | C8 | |
| | | P | 98 | R | 7 | C | 3 | | | | | | P | 99 | R | 7 | |
| | | | | | C1-40 | | | | | C1-40 | | | | | C1-4 | | |
| 8 | 9 | 10 | 11 | | 2 | 3 | 4 | 5 | 6 | 7 | 8 | 9 | 10 | 11 | | 2 | |
| C9 | C17 | C25 | C33 | A | C1 | C9 | C17 | C25 | C33 | C1 | C9 | C17 | C25 | C33 | A | C1 | |
| C10 | C18 | C26 | C34 | B | C2 | C10 | C18 | C26 | C34 | C2 | C10 | C18 | C26 | C34 | B | C2 | |
| C11 | C19 | C27 | C35 | C | C3 | C11 | C19 | C27 | C35 | C3 | C11 | C19 | C27 | C35 | C | C3 | |
| C12 | C20 | C28 | C36 | D | C4 | C12 | C20 | C28 | C36 | C4 | C12 | C20 | C28 | C36 | D | C4 | |
| C13 | C21 | C29 | C37 | E | C5 | C13 | C21 | C29 | C37 | C5 | C13 | C21 | C29 | C37 | E | C5 | |
| C14 | C22 | C30 | C38 | F | C6 | C14 | C22 | C30 | C38 | C6 | C22 | C22 | C30 | C38 | F | C6 | |
| C15 | C23 | C31 | C39 | G | C7 | C15 | C23 | C31 | C39 | C7 | C15 | C23 | C31 | C39 | G | C7 | |
| C16 | C24 | C32 | C40 | H | C8 | C16 | C24 | C32 | C40 | C8 | C16 | C24 | C32 | C40 | H | C8 | |
| | | P | 114 | R | 8 | C | 3 | | | | | | P | 115 | R | 8 | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 4 | R | 1 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 20 | R | 2 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 36 | R | 3 | C | 5 | | | | | |

-continued

BB3

| | | | | | | | | | | | | | | | | | |
|---|---|---|---|---|---|---|---|---|---|---|---|---|---|---|---|---|---|
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 52 | R | 4 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 68 | R | 5 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 84 | R | 6 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 100 | R | 7 | C | 5 | | | | | |
| | | | | C1-40 | | | | | | C1-40 | | | | | C1-40 | | |
| 3 | 4 | 5 | 6 | 7 | 8 | 9 | 10 | 11 | | 2 | 3 | 4 | 5 | 6 | 7 | 8 | 9 |
| C9 | C17 | C25 | C33 | C1 | C9 | C17 | C25 | C33 | A | C1 | C9 | C17 | C25 | C33 | C1 | C9 | C17 |
| C10 | C18 | C26 | C34 | C2 | C10 | C18 | C26 | C34 | B | C2 | C10 | C18 | C26 | C34 | C2 | C10 | C18 |
| C11 | C19 | C27 | C35 | C3 | C11 | C19 | C27 | C35 | C | C3 | C11 | C19 | C27 | C35 | C3 | C11 | C19 |
| C12 | C20 | C28 | C36 | C4 | C12 | C20 | C28 | C36 | D | C4 | C12 | C20 | C28 | C36 | C4 | C12 | C20 |
| C13 | C21 | C29 | C37 | C5 | C13 | C21 | C29 | C37 | E | C5 | C13 | C21 | C29 | C37 | C5 | C13 | C21 |
| C14 | C22 | C30 | C38 | C6 | C14 | C22 | C30 | C38 | F | C6 | C14 | C22 | C30 | C38 | C6 | C22 | C22 |
| C15 | C23 | C31 | C39 | C7 | C15 | C23 | C31 | C39 | G | C7 | C15 | C23 | C31 | C39 | C7 | C15 | C23 |
| C16 | C24 | C32 | C40 | C8 | C16 | C24 | C32 | C40 | H | C8 | C16 | C24 | C32 | C40 | C8 | C16 | C24 |
| C | 4 | | | | | | P | 116 | R | 8 | C | 5 | | | | | |

| | | | | | | | | | | | | | | | | |
|---|---|---|---|---|---|---|---|---|---|---|---|---|---|---|---|---|
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 5 | R | 1 | C | 6 | | | | | | P | 6 | R | 1 | C | 7 |

-continued

BB3

| | | | C1-40 | | | | | C1-40 | | | | | | C1-40 | | |
|---|---|---|---|---|---|---|---|---|---|---|---|---|---|---|---|---|
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 21 | R | 2 | C | 6 | | | | | | P | 22 | R | 2 | C | 7 |
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 37 | R | 3 | C | 6 | | | | | | P | 38 | R | 3 | C | 7 |
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 53 | R | 4 | C | 6 | | | | | | P | 54 | R | 4 | C | 7 |
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 69 | R | 5 | C | 6 | | | | | | P | 70 | R | 5 | C | 7 |
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 85 | R | 6 | C | 6 | | | | | | P | 86 | R | 6 | C | 7 |
| | | | C1-40 | | | | | C1-40 | | | | | | C1-40 | | |
| 10 | 11 | | 2 | 3 | 4 | 5 | 6 | 7 | 8 | 9 | 10 | 11 | | 2 | 3 | 4 |
| C25 | C33 | A | C1 | C9 | C17 | C25 | C33 | C1 | C9 | C17 | C25 | C33 | A | C1 | C9 | C17 |
| C26 | C34 | B | C2 | C10 | C18 | C26 | C34 | C2 | C10 | C18 | C26 | C34 | B | C2 | C10 | C18 |
| C27 | C35 | C | C3 | C11 | C19 | C27 | C35 | C3 | C11 | C19 | C27 | C35 | C | C3 | C11 | C19 |
| C28 | C36 | D | C4 | C12 | C20 | C28 | C36 | C4 | C12 | C20 | C28 | C36 | D | C4 | C12 | C20 |
| C29 | C37 | E | C5 | C13 | C21 | C29 | C37 | C5 | C13 | C21 | C29 | C37 | E | C5 | C13 | C21 |
| C30 | C38 | F | C6 | C14 | C22 | C30 | C38 | C6 | C22 | C22 | C30 | C38 | F | C6 | C14 | C22 |
| C31 | C39 | G | C7 | C15 | C23 | C31 | C39 | C7 | C15 | C23 | C31 | C39 | G | C7 | C15 | C23 |
| C32 | C40 | H | C8 | C16 | C24 | C32 | C40 | C8 | C16 | C24 | C32 | C40 | H | C8 | C16 | C24 |
| P | 101 | R | 7 | C | 6 | | | | | | P | 102 | R | 7 | C | 7 |

-continued

| BB3 | | | | | | | | | | | | | | | | | |
|---|---|---|---|---|---|---|---|---|---|---|---|---|---|---|---|---|---|
| | | | C1-40 | | | | | C1-40 | | | | | | C1-40 | | | |
| 10 | 11 | | 2 | 3 | 4 | 5 | 6 | 7 | 8 | 9 | 10 | 11 | | 2 | 3 | 4 | |
| C25 | C33 | A | C1 | C9 | C17 | C25 | C33 | C1 | C9 | C17 | C25 | C33 | A | C1 | C9 | C17 | |
| C26 | C34 | B | C2 | C10 | C18 | C26 | C34 | C2 | C10 | C18 | C26 | C34 | B | C2 | C10 | C18 | |
| C27 | C35 | C | C3 | C11 | C19 | C27 | C35 | C3 | C11 | C19 | C27 | C35 | C | C3 | C11 | C19 | |
| C28 | C36 | D | C4 | C12 | C20 | C28 | C36 | C4 | C12 | C20 | C28 | C36 | D | C4 | C12 | C20 | |
| C29 | C37 | E | C5 | C13 | C21 | C29 | C37 | C5 | C13 | C21 | C29 | C37 | E | C5 | C13 | C21 | |
| C30 | C38 | F | C6 | C14 | C22 | C30 | C38 | C6 | C22 | C22 | C30 | C38 | F | C6 | C14 | C22 | |
| C31 | C39 | G | C7 | C15 | C23 | C31 | C39 | C7 | C15 | C23 | C31 | C39 | G | C7 | C15 | C23 | |
| C32 | C40 | H | C8 | C16 | C24 | C32 | C40 | C8 | C16 | C24 | C32 | C40 | H | C8 | C16 | C24 | |
| P | 117 | R | 8 | C | 6 | | | | | | P | 118 | R | 8 | C | 7 | |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 7 | R | 1 | C | 8 | | | | | | P | 8 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 23 | R | 2 | C | 8 | | | | | | P | 24 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 39 | R | 3 | C | 8 | | | | | | P | 40 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 55 | R | 4 | C | 8 | | | | | | P | 56 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 71 | R | 5 | C | 8 | | | | | | P | 72 |

-continued

BB3

| | | | | | | | | | | | | | | | | | |
|---|---|---|---|---|---|---|---|---|---|---|---|---|---|---|---|---|---|
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 87 | R | 6 | C | 8 | | | | | | P | 88 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 103 | R | 7 | C | 8 | | | | | | P | 104 |
| | | C1-40 | | | | | | C1-40 | | | | | C1-40 | | | | |
| 5 | 6 | 7 | 8 | 9 | 10 | 11 | | 2 | 3 | 4 | 5 | 6 | 7 | 8 | 9 | 10 | 11 |
| C25 | C33 | C1 | C9 | C17 | C25 | C33 | A | C1 | C9 | C17 | C25 | C33 | C1 | C9 | C17 | C25 | C33 |
| C26 | C34 | C2 | C10 | C18 | C26 | C34 | B | C2 | C10 | C18 | C26 | C34 | C2 | C10 | C18 | C26 | C34 |
| C27 | C35 | C3 | C11 | C19 | C27 | C35 | C | C3 | C11 | C19 | C27 | C35 | C3 | C11 | C19 | C27 | C35 |
| C28 | C36 | C4 | C12 | C20 | C28 | C36 | D | C4 | C12 | C20 | C28 | C36 | C4 | C12 | C20 | C28 | C36 |
| C29 | C37 | C5 | C13 | C21 | C29 | C37 | E | C5 | C13 | C21 | C29 | C37 | C5 | C13 | C21 | C29 | C37 |
| C30 | C38 | C6 | C22 | C22 | C30 | C38 | F | C6 | C14 | C22 | C30 | C38 | C6 | C22 | C22 | C30 | C38 |
| C31 | C39 | C7 | C15 | C23 | C31 | C39 | G | C7 | C15 | C23 | C31 | C39 | C7 | C15 | C23 | C31 | C39 |
| C32 | C40 | C8 | C16 | C24 | C32 | C40 | H | C8 | C16 | C24 | C32 | C40 | C8 | C16 | C24 | C32 | C40 |
| | | | | | P | 119 | R | 8 | C | 8 | | | | | | P | 120 |
| | C1-40 | | | | | C1-40 | | | | | | C1-40 | | | | | |
| | 2 | 3 | 4 | 5 | 6 | 7 | 8 | 9 | 10 | 11 | | 2 | 3 | 4 | 5 | 6 | |
| A | C1 | C9 | C17 | C25 | C33 | C1 | C9 | C17 | C25 | C33 | A | C1 | C9 | C17 | C25 | C33 | |
| B | C2 | C10 | C18 | C26 | C34 | C2 | C10 | C18 | C26 | C34 | B | C2 | C10 | C18 | C26 | C34 | |
| C | C3 | C11 | C19 | C27 | C35 | C3 | C11 | C19 | C27 | C35 | C | C3 | C11 | C19 | C27 | C35 | |
| D | C4 | C12 | C20 | C28 | C36 | C4 | C12 | C20 | C28 | C36 | D | C4 | C12 | C20 | C28 | C36 | |
| E | C5 | C13 | C21 | C29 | C37 | C5 | C13 | C21 | C29 | C37 | E | C5 | C13 | C21 | C29 | C37 | |
| F | C6 | C14 | C22 | C30 | C38 | C6 | C14 | C22 | C30 | C38 | F | C6 | C14 | C22 | C30 | C38 | |
| G | C7 | C15 | C23 | C31 | C39 | C7 | C15 | C23 | C31 | C39 | G | C7 | C15 | C23 | C31 | C39 | |
| H | C8 | C16 | C24 | C32 | C40 | C8 | C16 | C24 | C32 | C40 | H | C8 | C16 | C24 | C32 | C40 | |
| R | 1 | C | 9 | | | | | | P | 9 | R | 1 | C | 10 | | | |
| | C1-40 | | | | | C1-40 | | | | | | C1-40 | | | | | |
| | 2 | 3 | 4 | 5 | 6 | 7 | 8 | 9 | 10 | 11 | | 2 | 3 | 4 | 5 | 6 | |
| A | C1 | C9 | C17 | C25 | C33 | C1 | C9 | C17 | C25 | C33 | A | C1 | C9 | C17 | C25 | C33 | |
| B | C2 | C10 | C18 | C26 | C34 | C2 | C10 | C18 | C26 | C34 | B | C2 | C10 | C18 | C26 | C34 | |
| C | C3 | C11 | C19 | C27 | C35 | C3 | C11 | C19 | C27 | C35 | C | C3 | C11 | C19 | C27 | C35 | |
| D | C4 | C12 | C20 | C28 | C36 | C4 | C12 | C20 | C28 | C36 | D | C4 | C12 | C20 | C28 | C36 | |
| E | C5 | C13 | C21 | C29 | C37 | C5 | C13 | C21 | C29 | C37 | E | C5 | C13 | C21 | C29 | C37 | |
| F | C6 | C14 | C22 | C30 | C38 | C6 | C14 | C22 | C30 | C38 | F | C6 | C14 | C22 | C30 | C38 | |
| G | C7 | C15 | C23 | C31 | C39 | C7 | C15 | C23 | C31 | C39 | G | C7 | C15 | C23 | C31 | C39 | |
| H | C8 | C16 | C24 | C32 | C40 | C8 | C16 | C24 | C32 | C40 | H | C8 | C16 | C24 | C32 | C40 | |
| R | 2 | C | 9 | | | | | | P | 25 | R | 2 | C | 10 | | | |
| | C1-40 | | | | | C1-40 | | | | | | C1-40 | | | | | |
| | 2 | 3 | 4 | 5 | 6 | 7 | 8 | 9 | 10 | 11 | | 2 | 3 | 4 | 5 | 6 | |
| A | C1 | C9 | C17 | C25 | C33 | C1 | C9 | C17 | C25 | C33 | A | C1 | C9 | C17 | C25 | C33 | |
| B | C2 | C10 | C18 | C26 | C34 | C2 | C10 | C18 | C26 | C34 | B | C2 | C10 | C18 | C26 | C34 | |
| C | C3 | C11 | C19 | C27 | C35 | C3 | C11 | C19 | C27 | C35 | C | C3 | C11 | C19 | C27 | C35 | |
| D | C4 | C12 | C20 | C28 | C36 | C4 | C12 | C20 | C28 | C36 | D | C4 | C12 | C20 | C28 | C36 | |
| E | C5 | C13 | C21 | C29 | C37 | C5 | C13 | C21 | C29 | C37 | E | C5 | C13 | C21 | C29 | C37 | |
| F | C6 | C14 | C22 | C30 | C38 | C6 | C14 | C22 | C30 | C38 | F | C6 | C14 | C22 | C30 | C38 | |
| G | C7 | C15 | C23 | C31 | C39 | C7 | C15 | C23 | C31 | C39 | G | C7 | C15 | C23 | C31 | C39 | |
| H | C8 | C16 | C24 | C32 | C40 | C8 | C16 | C24 | C32 | C40 | H | C8 | C16 | C24 | C32 | C40 | |
| R | 3 | C | 9 | | | | | | P | 41 | R | 3 | C | 10 | | | |

-continued

BB3

| | C1-40 | | | | | C1-40 | | | | | | C1-40 | | | | |
|---|---|---|---|---|---|---|---|---|---|---|---|---|---|---|---|---|
| | 2 | 3 | 4 | 5 | 6 | 7 | 8 | 9 | 10 | 11 | | 2 | 3 | 4 | 5 | 6 |
| A | C1 | C9 | C17 | C25 | C33 | C1 | C9 | C17 | C25 | C33 | A | C1 | C9 | C17 | C25 | C33 |
| B | C2 | C10 | C18 | C26 | C34 | C2 | C10 | C18 | C26 | C34 | B | C2 | C10 | C18 | C26 | C34 |
| C | C3 | C11 | C19 | C27 | C35 | C3 | C11 | C19 | C27 | C35 | C | C3 | C11 | C19 | C27 | C35 |
| D | C4 | C12 | C20 | C28 | C36 | C4 | C12 | C20 | C28 | C36 | D | C4 | C12 | C20 | C28 | C36 |
| E | C5 | C13 | C21 | C29 | C37 | C5 | C13 | C21 | C29 | C37 | E | C5 | C13 | C21 | C29 | C37 |
| F | C6 | C14 | C22 | C30 | C38 | C6 | C14 | C22 | C30 | C38 | F | C6 | C14 | C22 | C30 | C38 |
| G | C7 | C15 | C23 | C31 | C39 | C7 | C15 | C23 | C31 | C39 | G | C7 | C15 | C23 | C31 | C39 |
| H | C8 | C16 | C24 | C32 | C40 | C8 | C16 | C24 | C32 | C40 | H | C8 | C16 | C24 | C32 | C40 |
| R | 4 | C | 9 | | | | | | P | 57 | R | 4 | C | 10 | | |
| | C1-40 | | | | | C1-40 | | | | | | C1-40 | | | | |
| | 2 | 3 | 4 | 5 | 6 | 7 | 8 | 9 | 10 | 11 | | 2 | 3 | 4 | 5 | 6 |
| A | C1 | C9 | C17 | C25 | C33 | C1 | C9 | C17 | C25 | C33 | A | C1 | C9 | C17 | C25 | C33 |
| B | C2 | C10 | C18 | C26 | C34 | C2 | C10 | C18 | C26 | C34 | B | C2 | C10 | C18 | C26 | C34 |
| C | C3 | C11 | C19 | C27 | C35 | C3 | C11 | C19 | C27 | C35 | C | C3 | C11 | C19 | C27 | C35 |
| D | C4 | C12 | C20 | C28 | C36 | C4 | C12 | C20 | C28 | C36 | D | C4 | C12 | C20 | C28 | C36 |
| E | C5 | C13 | C21 | C29 | C37 | C5 | C13 | C21 | C29 | C37 | E | C5 | C13 | C21 | C29 | C37 |
| F | C6 | C14 | C22 | C30 | C38 | C6 | C14 | C22 | C30 | C38 | F | C6 | C14 | C22 | C30 | C38 |
| G | C7 | C15 | C23 | C31 | C39 | C7 | C15 | C23 | C31 | C39 | G | C7 | C15 | C23 | C31 | C39 |
| H | C8 | C16 | C24 | C32 | C40 | C8 | C16 | C24 | C32 | C40 | H | C8 | C16 | C24 | C32 | C40 |
| R | 5 | C | 9 | | | | | | P | 73 | R | 5 | C | 10 | | |
| | C1-40 | | | | | C1-40 | | | | | | C1-40 | | | | |
| | 2 | 3 | 4 | 5 | 6 | 7 | 8 | 9 | 10 | 11 | | 2 | 3 | 4 | 5 | 6 |
| A | C1 | C9 | C17 | C25 | C33 | C1 | C9 | C17 | C25 | C33 | A | C1 | C9 | C17 | C25 | C33 |
| B | C2 | C10 | C18 | C26 | C34 | C2 | C10 | C18 | C26 | C34 | B | C2 | C10 | C18 | C26 | C34 |
| C | C3 | C11 | C19 | C27 | C35 | C3 | C11 | C19 | C27 | C35 | C | C3 | C11 | C19 | C27 | C35 |
| D | C4 | C12 | C20 | C28 | C36 | C4 | C12 | C20 | C28 | C36 | D | C4 | C12 | C20 | C28 | C36 |
| E | C5 | C13 | C21 | C29 | C37 | C5 | C13 | C21 | C29 | C37 | E | C5 | C13 | C21 | C29 | C37 |
| F | C6 | C14 | C22 | C30 | C38 | C6 | C14 | C22 | C30 | C38 | F | C6 | C14 | C22 | C30 | C38 |
| G | C7 | C15 | C23 | C31 | C39 | C7 | C15 | C23 | C31 | C39 | G | C7 | C15 | C23 | C31 | C39 |
| H | C8 | C16 | C24 | C32 | C40 | C8 | C16 | C24 | C32 | C40 | H | C8 | C16 | C24 | C32 | C40 |
| R | 6 | C | 9 | | | | | | P | 89 | R | 6 | C | 10 | | |
| | C1-40 | | | | | C1-40 | | | | | | C1-40 | | | | |
| | 2 | 3 | 4 | 5 | 6 | 7 | 8 | 9 | 10 | 11 | | 2 | 3 | 4 | 5 | 6 |
| A | C1 | C9 | C17 | C25 | C33 | C1 | C9 | C17 | C25 | C33 | A | C1 | C9 | C17 | C25 | C33 |
| B | C2 | C10 | C18 | C26 | C34 | C2 | C10 | C18 | C26 | C34 | B | C2 | C10 | C18 | C26 | C34 |
| C | C3 | C11 | C19 | C27 | C35 | C3 | C11 | C19 | C27 | C35 | C | C3 | C11 | C19 | C27 | C35 |
| D | C4 | C12 | C20 | C28 | C36 | C4 | C12 | C20 | C28 | C36 | D | C4 | C12 | C20 | C28 | C36 |
| E | C5 | C13 | C21 | C29 | C37 | C5 | C13 | C21 | C29 | C37 | E | C5 | C13 | C21 | C29 | C37 |
| F | C6 | C14 | C22 | C30 | C38 | C6 | C14 | C22 | C30 | C38 | F | C6 | C14 | C22 | C30 | C38 |
| G | C7 | C15 | C23 | C31 | C39 | C7 | C15 | C23 | C31 | C39 | G | C7 | C15 | C23 | C31 | C39 |
| H | C8 | C16 | C24 | C32 | C40 | C8 | C16 | C24 | C32 | C40 | H | C8 | C16 | C24 | C32 | C40 |
| R | 7 | C | 9 | | | | | | P | 105 | R | 7 | C | 10 | | |
| | C1-40 | | | | | C1-40 | | | | | | C1-40 | | | | |
| | 2 | 3 | 4 | 5 | 6 | 7 | 8 | 9 | 10 | 11 | | 2 | 3 | 4 | 5 | 6 |
| A | C1 | C9 | C17 | C25 | C33 | C1 | C9 | C17 | C25 | C33 | A | C1 | C9 | C17 | C25 | C33 |
| B | C2 | C10 | C18 | C26 | C34 | C2 | C10 | C18 | C26 | C34 | B | C2 | C10 | C18 | C26 | C34 |
| C | C3 | C11 | C19 | C27 | C35 | C3 | C11 | C19 | C27 | C35 | C | C3 | C11 | C19 | C27 | C35 |
| D | C4 | C12 | C20 | C28 | C36 | C4 | C12 | C20 | C28 | C36 | D | C4 | C12 | C20 | C28 | C36 |
| E | C5 | C13 | C21 | C29 | C37 | C5 | C13 | C21 | C29 | C37 | E | C5 | C13 | C21 | C29 | C37 |
| F | C6 | C14 | C22 | C30 | C38 | C6 | C14 | C22 | C30 | C38 | F | C6 | C14 | C22 | C30 | C38 |
| G | C7 | C15 | C23 | C31 | C39 | C7 | C15 | C23 | C31 | C39 | G | C7 | C15 | C23 | C31 | C39 |
| H | C8 | C16 | C24 | C32 | C40 | C8 | C16 | C24 | C32 | C40 | H | C8 | C16 | C24 | C32 | C40 |
| R | 8 | C | 9 | | | | | | P | 121 | R | 8 | C | 10 | | |

| C1-40 | | | | | | C1-40 | | | | | C1-40 | | | | | |
|---|---|---|---|---|---|---|---|---|---|---|---|---|---|---|---|---|
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 10 | R | 1 | C | 11 | | | | | | P | 11 | R |

-continued

| BB3 | | | | | | | | | | | | | | | | |
|---|---|---|---|---|---|---|---|---|---|---|---|---|---|---|---|---|
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 26 | R | 2 | C | 11 | | | | | | P | 27 | R |
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 42 | R | 3 | C | 11 | | | | | | P | 43 | R |
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 58 | R | 4 | C | 11 | | | | | | P | 59 | R |
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 74 | R | 5 | C | 11 | | | | | | P | 75 | R |
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 90 | R | 6 | C | 11 | | | | | | P | 91 | R |
| C1-40 | | | | | | C1-40 | | | | | C1-40 | | | | | |
| 7 | 8 | 9 | 10 | 11 | | 2 | 3 | 4 | 5 | 6 | 7 | 8 | 9 | 10 | 11 | |
| C1 | C9 | C17 | C25 | C33 | A | C1 | C9 | C17 | C25 | C33 | C1 | C9 | C17 | C25 | C33 | A |
| C2 | C10 | C18 | C26 | C34 | B | C2 | C10 | C18 | C26 | C34 | C2 | C10 | C18 | C26 | C34 | B |
| C3 | C11 | C19 | C27 | C35 | C | C3 | C11 | C19 | C27 | C35 | C3 | C11 | C19 | C27 | C35 | C |
| C4 | C12 | C20 | C28 | C36 | D | C4 | C12 | C20 | C28 | C36 | C4 | C12 | C20 | C28 | C36 | D |
| C5 | C13 | C21 | C29 | C37 | E | C5 | C13 | C21 | C29 | C37 | C5 | C13 | C21 | C29 | C37 | E |
| C6 | C14 | C22 | C30 | C38 | F | C6 | C14 | C22 | C30 | C38 | C6 | C14 | C22 | C30 | C38 | F |
| C7 | C15 | C23 | C31 | C39 | G | C7 | C15 | C23 | C31 | C39 | C7 | C15 | C23 | C31 | C39 | G |
| C8 | C16 | C24 | C32 | C40 | H | C8 | C16 | C24 | C32 | C40 | C8 | C16 | C24 | C32 | C40 | H |
| | | | P | 106 | R | 7 | C | 11 | | | | | | P | 107 | R |

-continued

BB3

| | | | | | | | | | | | | | | | | | |
|---|---|---|---|---|---|---|---|---|---|---|---|---|---|---|---|---|---|
| C1-40 | | | | | | C1-40 | | | | | C1-40 | | | | | | |
| 7 | 8 | 9 | 10 | 11 | | 2 | 3 | 4 | 5 | 6 | 7 | 8 | 9 | 10 | 11 | | |
| C1 | C9 | C17 | C25 | C33 | A | C1 | C9 | C17 | C25 | C33 | C1 | C9 | C17 | C25 | C33 | A | |
| C2 | C10 | C18 | C26 | C34 | B | C2 | C10 | C18 | C26 | C34 | C2 | C10 | C18 | C26 | C34 | B | |
| C3 | C11 | C19 | C27 | C35 | C | C3 | C11 | C19 | C27 | C35 | C3 | C11 | C19 | C27 | C35 | C | |
| C4 | C12 | C20 | C28 | C36 | D | C4 | C12 | C20 | C28 | C36 | C4 | C12 | C20 | C28 | C36 | D | |
| C5 | C13 | C21 | C29 | C37 | E | C5 | C13 | C21 | C29 | C37 | C5 | C13 | C21 | C29 | C37 | E | |
| C6 | C14 | C22 | C30 | C38 | F | C6 | C14 | C22 | C30 | C38 | C6 | C14 | C22 | C30 | C38 | F | |
| C7 | C15 | C23 | C31 | C39 | G | C7 | C15 | C23 | C31 | C39 | C7 | C15 | C23 | C31 | C39 | G | |
| C8 | C16 | C24 | C32 | C40 | H | C8 | C16 | C24 | C32 | C40 | C8 | C16 | C24 | C32 | C40 | H | |
| | | | P | 122 | R | 8 | C | 11 | | | | | | P | 123 | R | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 1 | C | 12 | | | | | | P | 12 | R | 1 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 2 | C | 12 | | | | | | P | 28 | R | 2 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 3 | C | 12 | | | | | | P | 44 | R | 3 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 4 | C | 12 | | | | | | P | 60 | R | 4 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 5 | C | 12 | | | | | | P | 76 | R | 5 | C | 13 | | | | |

-continued

| BB3 | | | | | | | | | | | | | | | | | |
|---|---|---|---|---|---|---|---|---|---|---|---|---|---|---|---|---|---|
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 6 | C | 12 | | | | | | P | 92 | R | 6 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 7 | C | 12 | | | | | | P | 108 | R | 7 | C | 13 | | | | |
| C1-40 | | | | | C1-40 | | | | | | C1-40 | | | | | C1-4 | |
| 2 | 3 | 4 | 5 | 6 | 7 | 8 | 9 | 10 | 11 | | 2 | 3 | 4 | 5 | 6 | 7 | 8 |
| C1 | C9 | C17 | C25 | C33 | C1 | C9 | C17 | C25 | C33 | A | C1 | C9 | C17 | C25 | C33 | C1 | C9 |
| C2 | C10 | C18 | C26 | C34 | C2 | C10 | C18 | C26 | C34 | B | C2 | C10 | C18 | C26 | C34 | C2 | C10 |
| C3 | C11 | C19 | C27 | C35 | C3 | C11 | C19 | C27 | C35 | C | C3 | C11 | C19 | C27 | C35 | C3 | C11 |
| C4 | C12 | C20 | C28 | C36 | C4 | C12 | C20 | C28 | C36 | D | C4 | C12 | C20 | C28 | C36 | C4 | C12 |
| C5 | C13 | C21 | C29 | C37 | C5 | C13 | C21 | C29 | C37 | E | C5 | C13 | C21 | C29 | C37 | C5 | C13 |
| C6 | C14 | C22 | C30 | C38 | C6 | C14 | C22 | C30 | C38 | F | C6 | C14 | C22 | C30 | C38 | C6 | C14 |
| C7 | C15 | C23 | C31 | C39 | C7 | C15 | C23 | C31 | C39 | G | C7 | C15 | C23 | C31 | C39 | C7 | C15 |
| C8 | C16 | C24 | C32 | C40 | C8 | C16 | C24 | C32 | C40 | H | C8 | C16 | C24 | C32 | C40 | C8 | C16 |
| 8 | C | 12 | | | | | | P | 124 | R | 8 | C | 13 | | | | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 13 | R | 1 | C | 14 | | | | | | P | 14 | R | 1 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 29 | R | 2 | C | 14 | | | | | | P | 30 | R | 2 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 45 | R | 3 | C | 14 | | | | | | P | 46 | R | 3 | C | |

-continued

| | | | | | | | | | | | | | | | | | |
|---|---|---|---|---|---|---|---|---|---|---|---|---|---|---|---|---|---|
| BB3 | | | | | | | | | | | | | | | | | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 61 | R | 4 | C | 14 | | | | | | P | 62 | R | 4 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 77 | R | 5 | C | 14 | | | | | | P | 78 | R | 5 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 93 | R | 6 | C | 14 | | | | | | P | 94 | R | 6 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 109 | R | 7 | C | 14 | | | | | | P | 110 | R | 7 | C | |
| | | | | C1-40 | | | | | C1-40 | | | | | | C1-40 | | |
| 9 | 10 | 11 | | 2 | 3 | 4 | 5 | 6 | 7 | 8 | 9 | 10 | 11 | | 2 | 3 | |
| C17 | C25 | C33 | A | C1 | C9 | C17 | C25 | C33 | C1 | C9 | C17 | C25 | C33 | A | C1 | C9 | |
| C18 | C26 | C34 | B | C2 | C10 | C18 | C26 | C34 | C2 | C10 | C18 | C26 | C34 | B | C2 | C10 | |
| C19 | C27 | C35 | C | C3 | C11 | C19 | C27 | C35 | C3 | C11 | C19 | C27 | C35 | C | C3 | C11 | |
| C20 | C28 | C36 | D | C4 | C12 | C20 | C28 | C36 | C4 | C12 | C20 | C28 | C36 | D | C4 | C12 | |
| C21 | C29 | C37 | E | C5 | C13 | C21 | C29 | C37 | C5 | C13 | C21 | C29 | C37 | E | C5 | C13 | |
| C22 | C30 | C38 | F | C6 | C14 | C22 | C30 | C38 | C6 | C14 | C22 | C30 | C38 | F | C6 | C14 | |
| C23 | C31 | C39 | G | C7 | C15 | C23 | C31 | C39 | C7 | C15 | C23 | C31 | C39 | G | C7 | C15 | |
| C24 | C32 | C40 | H | C8 | C16 | C24 | C32 | C40 | C8 | C16 | C24 | C32 | C40 | H | C8 | C16 | |
| | P | 125 | R | 8 | C | 14 | | | | | | P | 126 | R | 8 | C | |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 15 | R | 1 | C | 16 | | | | | | P |

-continued

| BB3 | | | | | | | | | | | | | | | | | |
|---|---|---|---|---|---|---|---|---|---|---|---|---|---|---|---|---|---|
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 31 | R | 2 | C | 16 | | | | | | P |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 47 | R | 3 | C | 16 | | | | | | P |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 63 | R | 4 | C | 16 | | | | | | P |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 79 | R | 5 | C | 16 | | | | | | P |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 95 | R | 6 | C | 16 | | | | | | P |
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 111 | R | 7 | C | 16 | | | | | | P |

-continued

| BB3 | | | | | | | | | | | | | | | | | |
|---|---|---|---|---|---|---|---|---|---|---|---|---|---|---|---|---|---|
| | | | C1-40 | | | | | | C1-40 | | | | | C1-40 | | | |
| 4 | 5 | 6 | 7 | 8 | 9 | 10 | 11 | | 2 | 3 | 4 | 5 | 6 | 7 | 8 | 9 | 10 |
| C17 | C25 | C33 | C1 | C9 | C17 | C25 | C33 | A | C1 | C9 | C17 | C25 | C33 | C1 | C9 | C17 | C25 |
| C18 | C26 | C34 | C2 | C10 | C18 | C26 | C34 | B | C2 | C10 | C18 | C26 | C34 | C2 | C10 | C18 | C26 |
| C19 | C27 | C35 | C3 | C11 | C19 | C27 | C35 | C | C3 | C11 | C19 | C27 | C35 | C3 | C11 | C19 | C27 |
| C20 | C28 | C36 | C4 | C12 | C20 | C28 | C36 | D | C4 | C12 | C20 | C28 | C36 | C4 | C12 | C20 | C28 |
| C21 | C29 | C37 | C5 | C13 | C21 | C29 | C37 | E | C5 | C13 | C21 | C29 | C37 | C5 | C13 | C21 | C29 |
| C22 | C30 | C38 | C6 | C14 | C22 | C30 | C38 | F | C6 | C14 | C22 | C30 | C38 | C6 | C14 | C22 | C30 |
| C23 | C31 | C39 | C7 | C15 | C23 | C31 | C39 | G | C7 | C15 | C23 | C31 | C39 | C7 | C15 | C23 | C31 |
| C24 | C32 | C40 | C8 | C16 | C24 | C32 | C40 | H | C8 | C16 | C24 | C32 | C40 | C8 | C16 | C24 | C32 |
| 15 | | | | | | P | 127 | R | 8 | C | 16 | | | | | | P |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 16 | | | | | | | | | | | | | | | | | |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 32 | | | | | | | | | | | | | | | | | |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 48 | | | | | | | | | | | | | | | | | |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 64 | | | | | | | | | | | | | | | | | |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 80 | | | | | | | | | | | | | | | | | |
| 11 | | | | | | | | | | | | | | | | | |
| C33 | | | | | | | | | | | | | | | | | |
| C34 | | | | | | | | | | | | | | | | | |
| C35 | | | | | | | | | | | | | | | | | |
| C36 | | | | | | | | | | | | | | | | | |
| C37 | | | | | | | | | | | | | | | | | |
| C38 | | | | | | | | | | | | | | | | | |
| C39 | | | | | | | | | | | | | | | | | |
| C40 | | | | | | | | | | | | | | | | | |
| 96 | | | | | | | | | | | | | | | | | |

-continued

| BB3 |
| --- |
| 11 |
| C33 |
| C34 |
| C35 |
| C36 |
| C37 |
| C38 |
| C39 |
| C40 |
| 112 |
| 11 |
| C33 |
| C34 |
| C35 |
| C36 |
| C37 |
| C38 |
| C39 |
| C40 |
| 128 |

What is claimed is:

1. A method of making a logically-ordered, spatially-addressable array of compounds having a same common linear, branched or cyclic molecular core structure comprising at least three atoms of carbon, nitrogen, oxygen, phosphorus or sulfur and at least two structural diversity elements, wherein the molecular cores have attachment points for the structural diversity elements, an ability to present the structural diversity elements in controlled varying arrangements, and an ability to be constructed in a rapid concerted fashion, said array comprising at least a first sub-array and a second sub-array, wherein the compounds composing the first sub-array each have at least one common structural diversity element and the compounds composing the second sub-array each have at least one common structural diversity element, said method comprising the steps of:

(a) providing a plurality of reaction vessels organized into the first and second sub-arrays;

(b) adding reactants to each of the reaction vessels in a manner such that when reacted, the reactants form the compounds of the array, and such that the compounds composing each sub-array differ from one another by one change in a structural diversity element; and (c) reacting the contents of each reaction vessel under appropriate conditions to form the compounds of the sub-arrays in the logically-ordered array.

2. A method of making a spatially-addressable combinatorial array of at least 500 compounds in solution in multiple cycles, said method comprising the steps of:

(a) apportioning into a plurality of reaction vessels that are identifiable by their spatial addresses (i) a first plurality of reactants, each reactant comprising a same first reactive group and a different first structural diversity element such that the reactants composing the first plurality differ from one another, with one first reactant per reaction vessel; and (ii) a second reactant comprising a second reactive group and a second structural diversity element, with one second reactant per reaction vessel; and (b) concurrently reacting said first and second reactants in each of the plurality of reaction vessels under solution phase conditions wherein the first and second reactive groups react with one another by an addition reaction to form a compound; and (c) repeating steps (a) and (b), thus forming the combinatorial array of at least 500 different compounds in solution;

wherein each reaction vessel contains substantially only one compound, wherein each compound composing the combinatorial array comprises a same common linear, branched, or cyclic molecular core comprising at least three atoms of carbon, nitrogen, oxygen, phosphorus or sulfur having the first and second structural diversity elements attached thereto, and further wherein the compounds composing the array differ from one another by at least one change in a structural diversity element.

3. The method of claim 2 further including the step of formatting the contents of the reaction vessels into a spatially-addressable array.

4. The method of claim 1, 2 or 3, wherein each base module compound in the array is unique.

5. The method of claim 1, wherein the combinatorial array comprises at least 1000 compounds.

6. The method of claim 2, wherein the combinatorial array comprises at least 1000 compounds.

7. A method for making a spatially-addressable combinatorial array of compounds in solution, the compounds having a common molecular core structure and at least two structural diversity elements, wherein the array comprises at least 500 different compounds, the method comprising:

(a) selecting reagents suitable for preparing the compounds of the array;

(b) providing at least 500 spatially-addressable reaction vessels;

(c) apportioning the reagents into the reaction vessels; and (d) concurrently reacting the reagents in the reaction vessels in one of more cycles under solution phase conditions such that all the compounds of the array are formed in solution;

wherein each reaction vessel contains substantially only one compound, wherein each compound composing the combinatorial array comprises a same common linear, branched, or cyclic molecular core comprising at least three atoms of carbon, nitrogen, oxygen, phosphorus or sulfur, said core having at least two structural diversity elements attached thereto, and further wherein the compounds composing the array differ from one another by one at least one change in a structural diversity element.

8. The method of claim 7, further including, after step b) or step c), the step of formatting the contents of the reaction vessels into a spatially-addressable array.

9. The method of claim 7 wherein for each cycle the reagents in at least 80 different reaction vessels are concurrently reacted.

10. A method of making a spatially-addressable array of at least 500 different compounds, each of which is in solution, said compounds having a same common linear, branched, or cyclic molecular core comprising at least three atoms of carbon, nitrogen, oxygen, phosphorus or sulfur and at least two structural diversity elements attached thereto, said array comprising at least a first sub-array and a second sub-array, wherein the compounds composing the first sub-array each have at least one common structural diversity element, and the compounds composing the second sub-array each have at least one common structural diversity element, said method comprising the steps of:

(a) providing at least 500 wells organized into at least first and second sub-arrays;

(b) adding reactants to each of the wells in a manner such that, when reacted, the reactants form the compounds of the sub-arrays in the array, and such that the compounds composing each sub-array differ from one another by one change in a structural diversity element; and (c) concurrently reacting the contents of the wells under appropriate solution-phase conditions in one or more cycles to form all compounds of the sub-arrays in the array.

* * * * *

UNITED STATES PATENT AND TRADEMARK OFFICE

CERTIFICATE OF CORRECTION

PATENT NO. : 6,878,557 B1
DATED : April 12, 2005
INVENTOR(S) : Robert Zambias et al.

It is certified that error appears in the above-identified patent and that said Letters Patent is hereby corrected as shown below:

Title page,
Item [56], References Cited, U.S. PATENT DOCUMENTS, insert
-- 5,510,240 04/1996 Lam et al. --.
OTHER PUBLICATIONS, insert
-- Pirrung *et al., J. Am. Chem. Soc.*, vol. 117, pages 1240-1245 --; and
-- Pirrung *et al.* (Advance ACS Abstract, Vol. 8, No. 1, January 1, 1995). --.

Column 129,
Lines 25-49, replace claim 1 with claim 1 as follows:

1. A method of making a spatially-addressable array of at least 500 different compounds, each of which is in solution, said compounds having a same common linear, branched, or cyclic molecular core comprising at least three atoms of carbon, nitrogen, oxygen, phosphorus, or sulfur and at lest two structural diversity elements attached thereto, said array comprising at least a first sub-array and a second sub-array, wherein the compounds composing the first sub-array each have at least one common structural diversity element, and the compounds composing the second sub-array each have at least one common structural diversity element, said method comprising the steps of:

(a) providing at least 500 reaction vessels organized into at least first and second sub-arrays;

(b) adding reactants to each of the reaction vessels in a manner such that, when reacted, the reactants form the compounds of the sub-arrays in the array, wherein each reaction vessel contains substantially only one compound and such that the compounds composing each sub-array differ from one another by one change in a structural diversity element; and

UNITED STATES PATENT AND TRADEMARK OFFICE
CERTIFICATE OF CORRECTION

PATENT NO. : 6,878,557 B1
DATED : April 12, 2005
INVENTOR(S) : Robert Zambias et al.

It is certified that error appears in the above-identified patent and that said Letters Patent is hereby corrected as shown below:

Column 129, (cont'd), (c) concurrently reacting the contents of the reaction vessels under appropriate solution-phase conditions in one or more cycles to form all compounds of the sub-arrays in the array.

Signed and Sealed this

Fourth Day of April, 2006

JON W. DUDAS

*Director of the United States Patent and Trademark Office*

UNITED STATES PATENT AND TRADEMARK OFFICE

CERTIFICATE OF CORRECTION

PATENT NO. : 6,878,557 B1
APPLICATION NO. : 09/009846
DATED : April 12, 2005
INVENTOR(S) : Robert Zambias et al.

It is certified that error appears in the above-identified patent and that said Letters Patent is hereby corrected as shown below:

On the title page(s), (56) References Cited, U.S. Patent Documents, insert --5,510,240 04/1996 Lam et al.--.

On the title page(s), (56) References Cited, Other Publications, insert --Pirrung *et al., J. Am. Chem. Soc.*, vol. 117, pages 1240-1245--.

On the title page(s), (56) References Cited, Other Publications, insert --Pirrung *et al.* (Advance ACS Abstract, Vol. 8, No.1, January 1, 1995).--

At Col. 129, lines 25-49, replace claim 1 with claim 1 as follows:

--1. A method of making a spatially-addressable array of at least 500 different compounds, each of which is in solution, said compounds having a same common linear, branched, or cyclic molecular core comprising at least three atoms of carbon, nitrogen, oxygen, phosphorus, or sulfur and at least two structural diversity elements attached thereto, said array comprising at least a first sub-array and a second sub-array, wherein the compounds composing the first sub-array each have at least one common structural diversity element, and the compounds composing the second sub-array each have at least one common structural diversity element, said method comprising the steps of:

(a) providing at least 500 reaction vessels organized into at least first and second sub-arrays;

(b) adding reactants to each of the reaction vessels in a manner such that, when reacted, the reactants form the compounds of the sub-arrays in the array, wherein each reaction vessel contains substantially only one compound and such that the compounds composing each sub-array differ from one another by one change in a structural diversity element; and

UNITED STATES PATENT AND TRADEMARK OFFICE

CERTIFICATE OF CORRECTION

PATENT NO. : 6,878,557 B1
APPLICATION NO. : 09/009846
DATED : April 12, 2005
INVENTOR(S) : Robert Zambias et al.

It is certified that error appears in the above-identified patent and that said Letters Patent is hereby corrected as shown below:

(c) concurrently reacting the contents of the reaction vessels under appropriate solution-phase conditions in one or more cycles to form all compounds of the sub-arrays in the array.--

Signed and Sealed this

Sixth Day of March, 2007

JON W. DUDAS
*Director of the United States Patent and Trademark Office*

UNITED STATES PATENT AND TRADEMARK OFFICE

CERTIFICATE OF CORRECTION

PATENT NO. : 6,878,557 B1 
APPLICATION NO. : 09/009846
DATED : April 12, 2005
INVENTOR(S) : Robert Zambias et al.

It is certified that error appears in the above-identified patent and that said Letters Patent is hereby corrected as shown below:

At Col. 130, lines 38-40, replace claim 3 with claim 3 as follows:

3. The method of claim 2, further including, after step a) or step b), the step of formatting the contents of the reaction vessels into a spatially-addressable array.

At Col. 130, lines 41-42, replace claim 4 with claim 4 as follows:

4. The method of claim 1 or 2, wherein each compound in the array is unique.

Signed and Sealed this

Third Day of April, 2007

JON W. DUDAS

*Director of the United States Patent and Trademark Office*